United States Patent
Margolskee et al.

(10) Patent No.: US 7,803,982 B2
(45) Date of Patent: Sep. 28, 2010

(54) T1R3 TRANSGENIC ANIMALS, CELLS AND RELATED METHODS

(75) Inventors: Robert Margolskee, Upper Montclair, NJ (US); Minqing Rong, Foster City, CA (US); Sami Damak, Epalinges (CH)

(73) Assignee: The Mount Sinai School of Medicine of New York University, New York, NY (US)

( * ) Notice: Subject to any disclaimer, the term of this patent is extended or adjusted under 35 U.S.C. 154(b) by 0 days.

(21) Appl. No.: 10/892,632

(22) Filed: Jul. 15, 2004

(65) Prior Publication Data

US 2005/0177886 A1 Aug. 11, 2005

Related U.S. Application Data

(63) Continuation-in-part of application No. 10/475,620, filed as application No. PCT/US02/12656 on Apr. 22, 2002, now abandoned.

(60) Provisional application No. 60/285,209, filed on Apr. 20, 2001.

(51) Int. Cl.
- *A01K 67/027* (2006.01)
- *A01K 67/00* (2006.01)
- *G01N 33/00* (2006.01)
- *C12Q 3/00* (2006.01)
- *A01N 1/00* (2006.01)
- *C12N 5/07* (2010.01)

(52) U.S. Cl. .................. 800/18; 800/3; 800/8; 800/14; 800/21; 435/1.1; 435/1.2; 435/3; 435/354

(58) Field of Classification Search ........................ None
See application file for complete search history.

(56) References Cited

U.S. PATENT DOCUMENTS

| | | | |
|---|---|---|---|
| 3,725,453 A | 4/1973 | Lapidus et al. | |
| 4,115,538 A | 9/1978 | Satoh et al. | |
| 4,376,110 A | 3/1983 | David et al. | |
| 4,544,559 A | 10/1985 | Gil et al. | |
| 4,826,824 A | 5/1989 | Schiffman | |
| 4,873,191 A | 10/1989 | Wagner et al. | |
| 4,886,646 A | 12/1989 | Carter et al. | |
| 4,921,939 A | 5/1990 | Nofre et al. | |
| 4,946,778 A | 8/1990 | Ladner et al. | |
| 4,994,442 A | 2/1991 | Gil et al. | |
| 5,010,175 A | 4/1991 | Rutter et al. | |
| 5,013,716 A * | 5/1991 | Cherukuri et al. ............. | 514/23 |
| 5,034,506 A | 7/1991 | Summerton et al. | |
| 5,096,676 A | 3/1992 | McPherson et al. | |
| 5,130,105 A | 7/1992 | Carter et al. | |
| 5,168,062 A | 12/1992 | Stinski | |
| 5,221,410 A | 6/1993 | Kushner et al. | |
| 5,288,514 A | 2/1994 | Ellman | |
| 5,385,839 A | 1/1995 | Stinski | |
| 5,389,537 A | 2/1995 | Raines et al. | |
| 5,400,741 A | 3/1995 | DeTitta et al. | |
| 5,464,764 A * | 11/1995 | Capecchi et al. ............... | 435/6 |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes et al. | |
| 5,569,588 A | 10/1996 | Ashby et al. | |
| 5,580,771 A | 12/1996 | Beavo et al. | |
| 5,585,089 A | 12/1996 | Queen et al. | |
| 5,593,853 A | 1/1997 | Chen et al. | |
| 5,602,019 A | 2/1997 | Beavo et al. | |
| 5,637,684 A | 6/1997 | Cook et al. | |
| 5,652,131 A | 7/1997 | Beavo et al. | |
| 5,688,662 A | 11/1997 | Margolskee | |
| 5,702,936 A | 12/1997 | Beavo et al. | |
| 5,776,752 A | 7/1998 | Beavo et al. | |
| 5,777,195 A | 7/1998 | Fienberg et al. | |
| 5,780,607 A | 7/1998 | Goodnow, Jr. et al. | |
| 5,783,682 A | 7/1998 | Cook et al. | |
| 5,789,553 A | 8/1998 | Beavo et al. | |
| 5,792,844 A | 8/1998 | Sanghvi et al. | |
| 5,811,234 A | 9/1998 | Roninson et al. | |
| 5,814,500 A | 9/1998 | Dietz | |
| 5,817,759 A | 10/1998 | Margolskee | |
| 5,853,792 A | 12/1998 | Zolotov et al. | |
| 5,884,230 A | 3/1999 | Srinivasan et al. | |
| 6,004,808 A | 12/1999 | Negulescu et al. | |
| 6,008,000 A | 12/1999 | Margolskee | |
| 6,015,677 A | 1/2000 | Beavo et al. | |
| 6,037,119 A | 3/2000 | Beavo et al. | |

(Continued)

FOREIGN PATENT DOCUMENTS

EP           0 278 659 B1      5/1995

(Continued)

OTHER PUBLICATIONS

Zhao et al., 2003, Cell 115:255-266.*

(Continued)

*Primary Examiner*—Robert M Kelly
*Assistant Examiner*—Kelaginamane T. Hiriyanna
(74) *Attorney, Agent, or Firm*—Nixon Peabody LLP

(57) ABSTRACT

The present invention relates to the discovery, identification and characterization of a receptor protein, referred to herein as T1R3, which is expressed in taste receptor cells and associated with the perception of bitter and sweet taste. The invention encompasses transgenic animals and cells that do not express functional T1R3 protein, particularly knock-out animals and cells, and transgenic animals and cells that express a non-native T1R3 protein. Experimental model systems based on these animals and cells can be used to study T1R3-mediated taste transduction and responses of the components of the T1R3 signal transduction pathway to various tastants, furthering our understanding of the molecular biology and biochemistry of taste. Such model systems would also be useful for screening for novel tastants and taste modulators, such as enhancers of desirable flavors, and blockers of undesirable flavors.

2 Claims, 24 Drawing Sheets

U.S. PATENT DOCUMENTS

| | | | |
|---|---|---|---|
| 6,383,778 | B1 | 5/2002 | Zuker et al. |
| 6,558,910 | B2 | 5/2003 | Zuker et al. |
| 6,562,574 | B2 | 5/2003 | Altshuler et al. |
| 6,583,111 | B1 | 6/2003 | DiMarchi et al. |
| 6,608,176 | B2 | 8/2003 | Chaudhari et al. |
| 6,623,939 | B1 | 9/2003 | Zuker et al. |
| 6,675,105 | B2 | 1/2004 | Hogarth et al. |
| 2002/0086300 | A1 | 7/2002 | Adler et al. |
| 2002/0094551 | A1 | 7/2002 | Adler |
| 2002/0115205 | A1 | 8/2002 | Foord et al. |
| 2002/0119526 | A1 | 8/2002 | Zuker et al. |
| 2002/0128433 | A1 | 9/2002 | Yao et al. |
| 2002/0132273 | A1 | 9/2002 | Stryer et al. |
| 2002/0143151 | A1 | 10/2002 | Yao et al. |
| 2002/0160424 | A1 | 10/2002 | Adler et al. |
| 2002/0164645 | A1 | 11/2002 | Zuker et al. |
| 2002/0168635 | A1 | 11/2002 | Zuker et al. |
| 2002/0177576 | A1 | 11/2002 | McGregor et al. |
| 2003/0008344 | A1 | 1/2003 | Adler et al. |
| 2003/0013119 | A1 | 1/2003 | Margolskee |
| 2003/0022278 | A1 | 1/2003 | Zuker et al. |
| 2003/0022288 | A1 | 1/2003 | Zuker et al. |
| 2003/0036630 | A1 | 2/2003 | Zuker et al. |
| 2003/0040045 | A1 | 2/2003 | Zuker et al. |
| 2003/0045472 | A1 | 3/2003 | Axel et al. |
| 2003/0054448 | A1 | 3/2003 | Adler et al. |
| 2003/0148448 | A1 | 8/2003 | Liao et al. |
| 2003/0157568 | A1 | 8/2003 | Zuker et al. |
| 2003/0166103 | A1 | 9/2003 | Huang et al. |
| 2003/0166137 | A1 | 9/2003 | Zuker et al. |
| 2003/0216545 | A1 | 11/2003 | Spytek et al. |
| 2003/0219834 | A1 | 11/2003 | Julius et al. |
| 2003/0220479 | A1 | 11/2003 | Li et al. |
| 2003/0232407 | A1 | 12/2003 | Zoller et al. |
| 2004/0014038 | A1 | 1/2004 | Casman et al. |
| 2004/0018976 | A1 | 1/2004 | Feder et al. |
| 2004/0023294 | A1 | 2/2004 | Arizu et al. |
| 2004/0063148 | A1 | 4/2004 | Margolskee et al. |
| 2004/0229239 | A1* | 11/2004 | Adler et al. .................. 435/6 |

FOREIGN PATENT DOCUMENTS

| | | |
|---|---|---|
| EP | 0 372 707 B1 | 3/1996 |
| EP | 1 146 124 A2 | 10/2001 |
| JP | 2000-300206 A | 10/2000 |
| JP | 2001-269149 A | 10/2001 |
| WO | WO 88/05077 A1 | 7/1988 |
| WO | WO 89/02898 A1 | 4/1989 |
| WO | WO 89/09256 A1 | 10/1989 |
| WO | WO 90/05780 A1 | 5/1990 |
| WO | WO 90/05790 A1 | 5/1990 |
| WO | WO 90/08832 A1 | 8/1990 |
| WO | WO 91/09955 A1 | 7/1991 |
| WO | WO 91/19735 A1 | 12/1991 |
| WO | WO 92/00091 A1 | 1/1992 |
| WO | WO 92/05244 A1 | 4/1992 |
| WO | WO 92/05263 A1 | 4/1992 |
| WO | WO 92/20808 A1 | 11/1992 |
| WO | WO 93/10677 A1 | 6/1993 |
| WO | WO 93/20242 A1 | 10/1993 |
| WO | WO 93/21337 A1 | 10/1993 |
| WO | WO 94/12650 A2 | 6/1994 |
| WO | WO 94/21807 A2 | 9/1994 |
| WO | WO 95/28494 A1 | 10/1995 |
| WO | WO 97/04666 A1 | 2/1997 |
| WO | WO 00/06592 A1 | 2/2000 |
| WO | WO 00/06593 A1 | 2/2000 |
| WO | WO 00/27861 A1 | 5/2000 |
| WO | WO 00/38536 A1 | 7/2000 |
| WO | WO 01/18050 A3 | 3/2001 |
| WO | WO 01/64882 A3 | 9/2001 |
| WO | WO 01/66563 A2 | 9/2001 |
| WO | WO 01/77676 A1 | 10/2001 |
| WO | WO 01/83749 A2 | 11/2001 |
| WO | WO 01/90359 A2 | 11/2001 |
| WO | WO 01/98323 A2 | 12/2001 |
| WO | WO 01/98526 A2 | 12/2001 |
| WO | WO 02/18581 A2 | 3/2002 |
| WO | WO 02/22649 A2 | 3/2002 |
| WO | WO 02/26825 A2 | 4/2002 |
| WO | WO 02/29061 A2 | 4/2002 |
| WO | WO 02/30981 A1 | 4/2002 |
| WO | WO 02/36622 A2 | 5/2002 |
| WO | WO 02/46230 A2 | 6/2002 |
| WO | WO 02/054069 A1 | 7/2002 |
| WO | WO 02/061087 A2 | 8/2002 |
| WO | WO 02/063004 A2 | 8/2002 |
| WO | WO 02/064631 A2 | 8/2002 |
| WO | WO 02/086078 A2 | 10/2002 |
| WO | WO 02/086079 A2 | 10/2002 |
| WO | WO 02/101045 A2 | 12/2002 |
| WO | WO 03/000859 A2 | 1/2003 |
| WO | WO 03/001876 A2 | 1/2003 |
| WO | WO 03/004992 A2 | 1/2003 |
| WO | WO 03/006482 A2 | 1/2003 |
| WO | WO 03/023009 A2 | 3/2003 |
| WO | WO 03/025137 A2 | 3/2003 |
| WO | WO 03/102030 A1 | 12/2003 |
| WO | WO 2004/011617 A2 | 2/2004 |
| WO | WO 2004/018631 A2 | 3/2004 |

OTHER PUBLICATIONS

Nelson et al., 2001, Cell 106:381-390.*
Schiffman et al (Proceedings of the National Academy of Sciences of the United Sates of America, 1983, vol. 80, No. 19, pp. 6136-6140).*
Li et al., 2001, Mammalian Genome 12: 13-16.*
Abe et al., "Multiple Genes for G Protein-coupled Receptors and Their Expression in Lingual Epithelia," *FEBS Lett.* 316(3):253-256 (1993).
Adler et al., "A Novel Family of Mammalian Taste Receptors," *Cell* 100(6):693-702 (2000).
Aimutis, W.R., "Bioactive Properties of Milk Proteins with Particular Focus on Anticariogenesis," *J. Nutr.* 134(4):989S-995S (2004).
Akabas et al., "A Bitter Substance Induces a Rise in Intracellular Calcium in a Subpopulation of Rat Taste Cells," *Science* 242:1047-1050 (1988).
Altenhofen et al., "Control of Ligand Specificity in Cyclic Nucleotide-gated Channels from Rod Photoreceptors and Olfactory Epithelium," *Proc. Nat'l Acad. Sci. USA* 88:9868-9872 (1991).
Altona & Sundaralingam, "Conformational Analysis of the Sugar Ring in Nucleosides and Nucleotides. A New Description Using the Concept of Pseudorotation," *J. Am. Chem. Soc.* 94(23):8205-8212 (1972).
Altschul et al., "Basic Local Alignment Search Tool," *J. Mol. Biol.* 215(3):403-410 (1990).
Amer & Kreighbaum, "Cyclic Nucleotide Phosphodiesterases: Properties, Activators, Inhibitors, Structure-activity Relationships, and Possible Role in Drug Development," *J. Pharm. Sci.* 64(1):1-37 (1975).
American Type Culture Collection No. CCL-251.
Angers et al., "Detection of $\beta_2$-Adrenergic Receptor Dimerization in Living Cells Using Bioluminescence Resonance Energy Transfer (BRET)," *Proc. Nat'l Acad. Sci. USA* 97(7):3684-3689 (2000).
Ariyasu et al., "Taste Receptor T1 R3 is an Essential Molecule for the Cellular Recognition of the Disaccharide Trehalose," In Vitro *Cell Dev. Biol. Anim.* 39(1-2):80-88 (2003).
Assadi-Porter et al., "Correlation of the Sweetness of Variants of the Protein Brazzein with Patterns of Hydrogen Bonds Detected by NMR Spectroscopy," *J. Biol. Chem.* 278(33):31331-31339 (2003).
Assadi-Porter et al., "Efficient Production of Recombinant Brazzein, a Small, Heat-stable, Sweet-tasting Protein of Plant Origin," *Arch. Biochem. Biophys.* 376(2):252-258 (2000).

Assadi-Porter et al., "Sweetness Determinant Sites of Brazzein, A Small, Heat-stable, Sweet-tasting Protein," *Arch. Biochem. Biophys.* 376(2):259-265 (2000).

Avenet & Lindemann, "Perspectives of Taste Reception," *J. Membr. Biol.* 112(1):1-8 (1989).

Avenet et al., "Transduction in Taste Receptor Cells Requires cAMP-dependent Protein Kinase," *Nature* 331:351-354 (1988).

Axelsson et al., "The Influence of Dietary Nucleotides on Erythrocyte Membrane Fatty Acids and Plasma Lipids in Preterm Infants," *Acta Paediatr.* 86(5):539-544 (1997).

Bachmanov et al., "Positional Cloning of the Mouse Saccharin Preference (*Sac*) Locus," *Chem. Senses* 26:925-933 (2001).

Bachmanov et al., "Sucrose Consumption in Mice: Major Influence of Two Genetic Loci Affecting Peripheral Sensory Responses," *Mammal. Genome* 8:545-548 (1977).

Bai et al., "Dimerization of the Extracellular Calcium-sensing Receptor (CaR) on the Cell Surface of CaR-transfected HEK293 Cells," *J. Biol. Chem.* 273(36):23605-23610 (1998).

Bai et al., "Intermolecular Interactions Between Dimeric Calcium-sensing Receptor Monomers Are Important for Its Normal Function," *Proc. Nat'l Acad. Sci. USA* 96:2834-2839 (1999).

Bakre et al., "Expression and Regulation of the cGMP-binding, cGMP-specific Phosphodiesterase (PDE5) in Human Colonic Epithelial Cells: Role in the Induction of Cellular Refractoriness to the Heat-Stable Enterotoxin Peptide," *J. Cell Biochem.* 77(1):159-167 (2000).

Baldwin, J.M., "Structure and Function of Receptors Coupled to G Proteins," *Curr. Opin. Cell Biol.* 6(2):180-190(1994).

Baum, "Solid-phase Synthesis of Benzodiazepines," *Chem. Engineer. News* 71:33-34 (1993).

Beaucage & Caruthers, "Deoxynucleoside Phosphoramidites—A New Class of Key Intermediates for Deoxypolynucleotide Synthesis," *Tetrahedron Lett.* 22(20):1859-1862 (1981).

Beavo, J.A., "Multiple Isozymes of Cyclic Nucleotide Phosphodiesterase," *Adv. Second Mess. Phosphoprotein Res.* 22:1-38 (1988).

Benoist & Chambon, "In Vivo Sequence Requirements of the SV40 Early Promoter Region," *Nature* 290(5801):304-310 (1981).

Bernhardt et al., "Changes in $IP_3$ and Cytosolic $Ca^{2+}$ in Response to Sugars and Non-sugar Sweeteners in Transduction of Sweet Taste in the Rat," *J. Physiol.* 490(2):325-336 (1996).

Berridge & Irvine, "Inositol Trisphosphate, A Novel Second Messenger in Cellular Signal Transduction," *Nature* 312:315-321 (1984).

Bertrand et al., "Metabotropic Glutamate Receptor Binding Domain: Homology Modeling Study vs. Crystal Structure," http://www.accelrys.com/webzine/01/q2/appnotes/mglur.html (last accessed Mar. 18, 2004).

Bertrand et al., "Metabotropic Glutamate Receptor Binding Domain: A Homology Modeling Study," http://www.ibcp.fr/GGMM/Nimes/011.html (last accessed Mar. 18, 2004).

Bird et al., "Single-chain Antigen-binding Proteins," *Science* 242(4877):423-426 (1988).

Birnbaumer, "G Proteins in Signal Transduction," *Ann. Rev. Pharmacol. Toxicol.* 30:675-705 (1990).

Birnbaumer et al., "Receptor-effector Coupling by G Proteins," *Biochim. Biophys. Acta* 1031:163-224 (1990).

Blizard et al., "Quantitative Trait Loci Associated with Short-term Intake of Sucrose, Saccharin and Quinine Solutions in Laboratory Mice," *Chem. Senses* 24:373-385 (1999).

Blundell et al., "Knowledge-based Prediction of Protein Structures and the Design of Novel Molecules," *Nature* 326:347-352 (1987).

Bold et al., "Biomolecular Advances in Gastrointestinal Hormones," *Arch. Surg.* 128:1268-1273 (1993).

Booth & Nixon, "Reconstitution of Holotransketolase Is by a Thiamin-diphosphate-magnesium Complex," *Eur. J. Biochem.* 218:261-265 (1993).

Boughter, Jr. et al., "Differential Expression of α-Gustducin in Taste Bud Populations of the Rat and Hamster," *J. Neurosci.* 17(8):2852-2858 (1997).

Bourne et al., "The GTPase Superfamily: A Conserved Switch for Diverse Cell Functions," *Nature* 348:125-132 (1990).

Bourne et al., "The GTPase Superfamily: Conserved Structure and Molecular Mechanism," *Nature* 349(6305) 117-127 (1991).

Bower et al., "Prediction of Protein Side-chain Rotamers from a Backbone-dependent Rotamer Library: A New Homology Modeling Tool," *J. Mol. Biol.* 267(5):1268-1282 (1997).

Bowie et al., "A Method to Identify Protein Sequences That Fold into a Known Three-dimensional Structure," *Science* 253:164-170 (1991).

Brand et al., "Inhibition by Amiloride of Chorda Tympani Responses Evoked by Monovalent Salts," *Brain Res.* 334(2):207-214 (1985).

Brinster et al., "Regulation of Metallothionein-Thymidine Kinase Fusion Plasmids Injected into Mouse Eggs," *Nature* 296(5852):39-42 (1982).

Bronstein et al., "Chemiluminescent Reporter Gene Assays: Sensitive Detection of the GUS and SEAP Gene Products," *BioTechniques* 17(1):172-177 (1994).

Brubaker & Drucker, "Structure-function of the Glucagon Receptor Family of G Protein-coupled Receptors: The Glucagon, GIP, GLP-1, and GLP-2 Receptors," *Receptors Channels* 8:179-188 (2002).

Bruch & Kalinoski, "Interaction of GTP-binding Regulatory Proteins with Chemosensory Receptors," *J. Biol. Chem.* 262(5):2401-2404 (1987).

Bufe et al., "The Human TAS2R16 Receptor Mediates Bitter Taste in Response to β-Glucopyranosides," *Nat. Genet.* 32:397-401 (2002).

Cagan & Morris, "Biochemical Studies of Taste Sensation: Binding to Taste Tissue of $^3$H-labeled Monellin, a Sweet-tasting Protein," *Proc. Nat'l Acad. Sci. USA* 76(4):1692-1696 (1979).

Caldwell et al., "Solution Structure of the Thermostable Sweet-tasting Protein Brazzein," *Nat. Struct. Biol.* 5(6):427-431 (1998).

Campbell & Bermak, "Phosphonate Ester Synthesis Using a Modified Mitsunobu Condensation," *J. Org. Chem.* 59:658-660 (1994).

Cane et al., "Harnessing the Biosynthetic Code: Combinations, Permutations, and Mutations," *Science* 282(5386):63-68 (1998).

Cao et al., "Aberrant Regulation of Human Intestinal Proglucagon Gene Expression in the NCI-H716 Cell Line," *Endocrinology* 144(5):2025-2033 (2003).

Capecchi, "Altering the Genome by Homologous Recombination," *Science* 244(4910):1288-1292 (1989).

Capeless & Whitney, "The Genetic Basis of Preference for Sweet Substances Among Inbred Strains of Mice: Preference Ratio Phenotypes and the Alleles of the *Sac* and *dpa* Loci," *Chem. Senses* 20:291-298 (1995).

Capeless et al., "Chromosome Mapping of *Soa*, a Gene Influencing Gustatory Sensitivity to Sucrose Octaacetate in Mice," *Behav. Genet.* 22(6):655-663 (1992).

Capretta, P.J., "Saccharin and Saccharin-glucose Ingestion in Two Inbred Strains of *Mus musculus*," *Psychon. Sci.* 21(3):133-135 (1970).

Carson, "*RIBBONS* 2.0," *J. Appl. Cryst.* 24:958-961 (1991).

Chandrashekar et al., "T2Rs Function as Bitter Taste Receptors," *Cell* 100(6):703-711 (2000).

Chaudhari & Roper, "Molecular and Physiological Evidence for Glutamate (*Umami*) Taste Transduction via a G Protein-coupled Receptor," *Ann. NY Acad. Sci.* 855:398-406 (1998).

Chaudhari et al., "A Metabotropic Glutamate Receptor Variant Functions as a Taste Receptor," *Nat. Neurosci.* 3(2):113-119 (2000).

Chaudhari et al., "The Taste of Monosodium Glutamate: Membrane Receptors in Taste Buds," *J. Neurosci.* 16(12):3817-3826 (1996).

Chayen, "A Novel Technique to Control the Rate of Vapour Diffusion, Giving Larger Protein Crystals," *J. Appl. Cryst.* 30:198-202 (1997).

Chen et al., "'Analogous' Organic Synthesis of Small-compound Libraries: Validation of Combinatorial Chemistry in Small-molecule Synthesis," *J. Amer. Chem. Soc.* 116:2661-2662 (1994).

Cheung et al., "Specific Activation of $G_S$ by Synthetic Peptides Corresponding to an Intracellular Loop of the β-Adrenergic Receptor," *FEBS Lett.* 279(2):277-280 (1991).

Cho et al., "An Unnatural Biopolymer," *Science* 261:1303-1305 (1993).

Cole et al., "The EBV-Hybridoma Technique and Its Application to Human Lung Cancer," *in* Monoclonal Antibodies and Cancer Therapy 77-96 (Ralph A. Reisfeld & Stewart Sell eds., 1985).

Colson et al., "Static and Dynamic Roles of Extracellular Loops in G-protein-coupled Receptors: A Mechanism for Sequential Binding of Thyrotropin-releasing Hormone to Its Receptor," *Biophys. J.* 74:1087-1100 (1998).

Conklin & Bourne, "Structural Elements of Gα Subunits That Interact with Gβγ, Receptors, and Effectors," *Cell* 73(4):631-641 (1993).

Cory & Bentley, "MATCHMOL, an Interactive Computer Graphics Procedure for Superposition of Molecular Models," *J. Mol. Graphics* 2(2):39-42 (1984).

Cote et al., "Generation of Human Monoclonal Antibodies Reactive with Cellular Antigens," *Proc. Nat'l Acad. Sci. USA* 80:2026-2030 (1983).

Thomas E. Creighton, Proteins: Structures and Molecular Principles (1983) (Table of Contents Only).

Cremer & Pople, "A General Definition of Ring Puckering Coordinates," *J. Am. Chem. Soc.* 97(6):1354-1358 (1975).

Cuff & Barton, "Application of Multiple Sequence Alignment Profiles to Improve Protein Secondary Structure Prediction," *Proteins* 40(3):502-511 (2000).

Cummings et al., "Sweet Taste Transduction in Hamster: Sweeteners and Cyclic Nucleotides Depolarize Taste Cells by Reducing a K+ Current," *J. Neurophysiol.* 75(3):1256-1263(1996).

Brown, "Hybridization Analysis of DNA Blot with a Radiolabeled DNA Probe," in 2 Current Protocols in Molecular Biology 2.10.2-2.10.3 (Frederick M. Ausubel et al. eds., 1989).

1-4 Current Protocols in Molecular Biology (Fred M. Ausubel et al. eds., 1994) (Table of Contents only).

Cuvillier et al., "Suppression of Ceramide-mediated Programmed Cell Death by Sphingosine-l-phosphate," *Nature* 381:800-803 (1996).

D'Arcy et al., "A Novel Approach to Crystallising Proteins Under Oil," *J. Cryst. Growth* 168:175-180 (1996).

Damak et al., "Detection of Sweet and Umami Taste in the Absence of Taste Receptor T1r3," *Science* 301:850-853 (2003).

Danilova et al., "Responses of Single Taste Fibers and Whole Chorda Tympani and Glossopharyngeal Nerve in the Domestic Pig, *Sus scrofa*," *Chem. Senses* 24:301-316 (1999).

Danilova et al., "Sense of Taste in a New World Monkey, the Common Marmoset: Recordings from the Chorda Tympani and Glossopharyngeal Nerves," *J. Neurophysiol.* 88:579-594 (2002).

Davidson et al., "Structure and Function in Rhodopsin: Replacement by Alanine of Cysteine Residues 110 and 187, Components of a Conserved Disulfide Bond in Rhodopsin, Affects the Light-activated Metarhodopsin II State," *Proc. Nat'l Acad. Sci. USA* 91:4029-4033 (1994).

De Boer et al., "The *tac* Promoter: A Functional Hybrid Derived from the *trp* and *lac* Promoters," *Proc. Nat'l Acad. Sci. USA* 80:21-25 (1983).

Devereux et al., "A Comprehensive Set of Sequence Analysis Programs for the VAX," *Nucl. Acids Res.* 12(1):387-395 (1984).

Dhallan et al., "Primary Structure and Functional Expression of a Cyclic Nucleotide-activated Channel from Olfactory Neurons," *Nature* 347:184-187 (1990).

Dixon et al., "Cloning of the Gene and cDNA for Mammalian β-Adrenergic Receptor and Homology with Rhodopsin," *Nature* 321:75-79 (1986).

Dixon et al., "Genetic Analysis of the Molecular Basis for β-Adrenergic Receptor Subtype Specificity," *Proteins* 6(3):267-274 (1989).

Drucker, "Biological Actions and Therapeutic Potential of the Glucagon-like Peptides," *Gastroenterol.* 122:531-544 (2002).

DuBois et al., "Dihydrochalcone Sweeteners. Synthesis and Sensory Evaluation of a Homoserine-dihydrochalcone Conjugate with Low Aftertaste, Sucrose-like Organoleptic Properties," *J. Agric. Food Chem.* 29(6):1269-1276 (1981).

DuBois et al., "Diterpenoid Sweeteners. Synthesis and Sensory Evaluation of Stevioside Analogues with Improved Organoleptic Properties," *J. Med. Chem.* 28(1):93-98 (1985).

Ebert et al., "Transgenic Production of a Variant of Human Tissue-type Plasminogen Activator in Goat Milk: Generation of Transgenic Goats and Analysis of Expression," *Biotechnol.* 9(9):835-838 (1991).

Ehses et al., "Glucose-dependent Insulinotropic Polypeptide Promotes β-(INS-1) Cell Survival Via Cyclic Adenosine Monophosphate-mediated Caspase-3 Inhibition and Regulation of p38 Mitogen-activated Protein Kinase," *Endocrinol.* 144(10):4433-4445 (2003).

Eisenberg et al., "VERIFY3D: Assessment of Protein Models with Three-dimensional Profiles," *Methods Enzymol.* 277:396-404 (1997).

Ermak & McCammon, "Brownian Dynamics with Hydrodynamic Interactions," *J. Chem. Phys.* 69(4):1352-1360 (1978).

Fan et al., "Mutational Analysis of the Cysteines in the Extracellular Domain of the Human $Ca^{2+}$ Receptor: Effects on Cell Surface Expression, Dimerization and Signal Transduction," *FEBS Lett.* 436(3):353-356 (1998).

Farbman et al., "Labeling of Sweet Taste Binding Sites Using a Colloidal Gold-labeled Sweet Protein, Thaumatin," *Scan. Microsc.* 1(1):351-357 (1987).

Faurobert et al., "Tryptophan W207 in Transducin Tα Is the Fluorescence Sensor of the G Protein Activation Switch and Is Involved in the Effector Binding," *EMBO J.* 12(11):4191-4198(1993).

Feingold et al., "An Olfactory Receptor Gene Is Located in the Extended Human β-Globin Gene Cluster and Is Expressed in Erythroid Cells," *Genomics* 61(1):15-23 (1999).

Felley-Bosco et al., "Constitutive Expression of Inducible Nitric Oxide Synthase in Human Bronchial Epithelial Cells Induces c-*fos* and Stimulates the cGMP Pathway," *Am. J. Resp. Cell Mol. Biol.* 11:159-164 (1994).

Fetrow & Bryant, "New Programs for Protein Tertiary Structure Prediction," *Biotechnol.* 11(4):479-484 (1993).

Fiser et al., "Modeling of Loops in Protein Structures [In Process Citation]," *Protein Sci.* 9:1753-1773 (2000).

Fong, T.M., "Mechanistic Hypotheses for the Activation of G-protein-coupled Receptors," *Cell. Signal.* 8(3):217-224 (1996).

Frank & Blizard, "Chorda Tympani Responses in Two Inbred Strains of Mice with Different Taste Preferences," *Physiol. Behav.* 67(2):287-297 (1999).

Fuller, J.L., "Single-locus Control of Saccharin Preference in Mice," *J. Hered.* 65:33-36 (1974).

Fung & Nash, "Characterization of Transducin from Bovine Retinal Rod Outer Segments," *J. Biol. Chem.* 258(17):10503-10510 (1983).

Fung et al., "Flow of Information in the Light-triggered Cyclic Nucleotide Cascade of Vision," *Proc. Nat'l Acad. Sci. USA* 78(1):152-156 (1981).

Furka et al., "General Method for Rapid Synthesis of Multicomponent Peptide Mixtures," *Int. J. Pept. Prot. Res.* 37:487-493 (1991).

Furness et al., "Nutrient Tasting and Signaling Mechanisms in the Gut II. The Intestine as a Sensory Organ: Neural, Endocrine, and Immune Responses," *Am. J. Physiol.* 277(5 Pt 1):G922-G928 (1999).

Oligonucleotide Synthesis: A Practical Approach (M. J. Gait ed., 1984) (Table of Contents Only).

Genbank Accession No. AC026283 (Jul. 7, 2000).

Genbank Accession No. AF368024 (May 23, 2001).

Genbank Accession No. AL139287 (Jan. 16, 2007).

Genbank Accession No. D18346 (Sep. 21, 2006).

Gibbs et al., "Structure/Function Relationships of Ras and Guanosine Triphosphatase-activating Protein," 6 G Proteins and Signal Transduction 77-85 (1990).

Gilbertson, T.A., "The Physiology of Vertebrate Taste Reception," *Curr. Opin. Neurobiol.* 3(4):532-539 (1993).

Gilbertson et al., "Proton Currents Through Amiloride-sensitive Na Channels in Hamster Taste Cells," *J. Gen. Physiol.* 100(5):803-824 (1992).

Gilbertson et al., "The Molecular Physiology of Taste Transduction," *Curr. Opin. Neurobiol.* 10:519-527 (2000).

Gillespie, "Phosphodiesterases in Visual Transduction by Rods and Cones," in Cyclic Nucleotide Phosphodiesterases: Structure, Regulation and Drug Action 163-184 (Joe Beavo & Miles D. Houslay eds., 1990).

Gingeras et al., "Simultaneous Genotyping and Species Identification Using Hybridization Pattern Recognition Analysis of Generic *Mycobacterium* DNA Arrays," *Genome Res.* 8:435-448 (1998).

Glendinning, J.I., "Is the Bitter Rejection Response Always Adaptive?," *Physiol. Behav.* 56(6):1217-1227 (1994).

Glendinning et al., "Contribution of Different Bitter-sensitive Taste Cells to Feeding Inhibition in a Caterpillar (*Manduca sexta*)," *Behav. Neurosci.* 113(4):840-854 (1999).

1 DNA Cloning: A Practical Approach (David M. Glover ed., 1985) (Table of Contents Only).

Goldsmith et al., "Antibodies Directed Against Synthetic Peptides Distinguish Between GTP-binding Proteins in Neutrophil and Brain," *J. Biol. Chem.* 262(30):14683-14688 (1987).

Goodford, P.J., "A Computational Procedure for Determining Energetically Favorable Binding Sites on Biologically Important Macromolecules," *J. Med. Chem.* 28(7):849-857 (1985).

Goodsell & Olson, "Automated Docking of Substrates to Proteins by Simulated Annealing," *Proteins* 8(3):195-202 (1990).

Gordon, J.W., "Transgenic Animals,"*Intl. Rev. Cytol.* 115:171-229 (1989).

Graber et al., "Expression and Purification of Functional G Protein α Subunits Using a Baculovirus Expression System," *J. Biol. Chem.* 267(2):1271-1278 (1992).

Graziano et al., "Purification of Recombinant $G_{S\alpha}$," *Methods Enzymol.* 195:192-202 (1991).

Greenberg et al., "Enzymatic Regulation of the Concentration of Cyclic GMP in Mouse Brain," *Neuropharmacol.* 17:737-745 (1978).

Greenberg et al., "Stimulation,of Neuronal Acetylcholine Receptors Induces Rapid Gene Transcription," *Science* 234:80-83 (1986).

Greer, J., "Comparative Modeling of Homologous Proteins," *Methods Enzymol.* 202:239-252 (1991).

Gschwend et al., "Molecular Docking Towards Drug Discovery," *J. Mol. Recognit.* 9(2):175-186 (1996).

Guan et al., "Enhancement of Membrane Insertion and Function in a Type IIIb Membrane Protein Following Introduction of a Cleavable Signal Peptide," *J. Biol. Chem.* 267(31):21995-21998 (1992).

Günthard et al., "Comparative Performance of High-density Oligonucleotide Sequencing and Dideoxynucleotide Sequencing of HIV Type 1 *pol* from Clinical Samples," *AIDS Res. Hum. Retroviruses* 14(10):869-876 (1998).

Hacia et al., "Two Color Hybridization Analysis Using High Density Oligonucleotide Arrays and Energy Transfer Dyes," *Nucl. Acids Res.* 26(16):3865-3866 (1998).

Hagihara et al., "Vinylogous Polypeptides: An Alternative Peptide Backbone, " *J. Am. Chem. Soc.* 114:6568-6570 (1992).

Halliday et al., "Limited Trypsin Proteolysis of Photoreceptor GTP-binding Protein," *J. Biol. Chem.* 259(1):516-525 (1984).

Hamm et al., "Site of G Protein Binding to Rhodopsin Mapped with Synthetic Peptides from the α Subunit," *Science* 241(4867):832-835 (1988).

Hanks & Quinn, "Protein Kinase Catalytic Domain Sequence Database: Identification of Conserved Features of Primary Structure and Classification of Family Members," *Methods Enzymol.* 200:38-62 (1991).

Hanks et al., "The Protein Kinase Family: Conserved Features and Deduced Phylogeny of the Catalytic Domains," *Science* 241:42-52 (1988).

Hansen & Beavo, "Differential Recognition of Calmodulin-Enzyme Complexes by a Conformation-specific Anti-calmodulin Monoclonal Antibody," *J. Biol. Chem.* 261(31):14636-14645 (1986).

Hansen & Beavo, "Purification of Two Calcium/Calmodulin-dependent Forms of Cyclic Nucleotide Phosphodiesterase by Using Conformation-specific Monoclonal Antibody Chromatography," *Proc. Nat'l Acad. Sci. USA* 79:2788-2792 (1982).

Harder et al., "Assessing Gustatory Detection Capabilities Using Preference Procedures," *Chem. Senses* 14(4):547-564 (1989).

Havlickova et al., "The Intracellular Loops of the GB2 Subunit Are Crucial for G-protein Coupling of the Heteromeric γ-Aminobutyrate B Receptor," *Mol. Pharmacol.* 62(2):343-350 (2002).

He et al., "Partial Rescue of Taste Responses of α-Gustducin Null Mice by Transgenic Expression of α-Transducin," *Chem. Senses* 27:719-727 (2002).

Heck et al., "Salt Taste Transduction Occurs Through an Amiloride-sensitive Sodium Transport Pathway," *Science* 223:403-405 (1984).

Hellekant et al., "Primate Sense of Taste: Behavioral and Single Chorda Tympani and Glossopharyngeal Nerve Fiber Recordings in the Rhesus Monkey, *Macaca mulatta*," *J. Neurophysiol.* 77(2):978-993 (1997).

Hermans & Challiss, "Structural, Signalling and Regulatory Properties of the Group I Metabotropic Glutamate Receptors: Prototypic Family C G-protein-coupled Receptors," *Biochem. J.* 359:465-484 (2001).

Herness, M.S., "Cellular Mechanisms of Taste Transduction," *Ann. Rev. Physiol.* 61:873-900 (1999).

Higgins et al., "Using CLUSTAL for Multiple Sequence Alignments," *Methods Enzymol.* 266:383-402 (1996).

HIji, Y, "Selective Elimination of Taste Responses to Sugars by Proteolytic Enzymes," *Nature* 256:427-429 (1975).

Hirschmann et al., "Nonpeptidal Peptidomimetics with β-D-Glucose Scaffolding. A Partial Somatostatin Agonist Bearing a Close Structural Relationship to a Potent, Selective Substance P Antagonist," *J. Am. Chem. Soc.* 114:9217-9218 (1992).

Höfer & Drenckhahn, "Identification of the Taste Cell G-protein, α-Gustducin, in Brush Cells of the Rat Pancreatic Duct System," *Histochem. Cell Biol.* 110(3):303-309 (1998).

Höfer et al., "Taste Receptor-like Cells in the Rat Gut Identified by Expression of α-Gustducin," *Proc. Nat'l Acad. Sci. USA* 93:6631-6634 (1996).

Manipulating the Mouse Embryo: A Laboratory Manual (Brigid Hogan et al. eds., 2d ed. 1994) (Table of Contents only).

Holst et al., "High Constitutive Signaling of the Ghrelin Receptor—Identification of a Potent Inverse Agonist," *Mol. Endocrinol.* 17(11):2201-2210 (2003).

Hoon et al., "Functional Expression of the Taste Specific G-protein, α-Gustducin," *Biochem. J.* 309:629-636 (1995).

Hoon et al., "Putative Mammalian Taste Receptors: A Class of Taste-specific GPCRs with Distinct Topographic Selectivity," *Cell* 96:541-551 (1999).

Horne et al., "Bitter Taste of Saccharin and Acesulfame-K," *Chem. Senses* 27:31-38 (2002).

Horton et al., "Gene Splicing by Overlap Extension," *Methods Enzymol.* 217:270-279 (1993).

Hosoda et al., "Purification and Characterization of Rat des-Gln[14]-ghrelin, a Second Endogenous Ligand for the Growth Hormone Secretagogue Receptor," *J. Biol. Chem.* 275(29):21995-22000 (2000).

Houghton et al., "Generation and Use of Synthetic Peptide Combinatorial Libraries for Basic Research and Drug Discovery," *Nature* 354:84-86 (1991).

Huang et al., "Gγ 13 Colocalizes with Gustducin in Taste Receptor Cells and Mediates $IP_3$ Responses to Bitter Denatonium," *Nat. Neurosci.* 2(12):1055-1062 (1999).

Huang et al., "Identification of Allosteric Antagonists of Receptor-guanine Nucleotide-binding Protein Interactions," *Mol. Pharmacol.* 37(2):304-310 (1990).

Huston et al., "Protein Engineering of Antibody Binding Sites: Recovery of Specific Activity in an Anti-digoxin Single-chain Fv Analogue Produced in *Escherichia coli*," *Proc. Nat'l Acad. Sci. USA* 85:5879-5883 (1988).

Hwa et al., "Structure and Function in Rhodopsin: Further Elucidation of the Role of the Intradiscal Cysteines, Cys-110, -185, and -187, in Rhodopsin Folding and Function," *Proc. Nat'l Acad. Sci. USA* 96:1932-1935 (1999).

Imoto et al., "A Novel Peptide Isolated from the Leaves of *Gymnema sylvestre*-I. Characterization and Its Suppressive Effect on the Neural Reponses to Sweet Taste Stimuli in the Rat," *Comp. Biochem. Physiol.* 100A(2):309-314 (1991).

Inoue et al., "Whole Nerve Chorda Tympani Responses to Sweeteners in C57BL/6ByJ and 129P3/J Mice," *Chem. Senses* 26:915-923 (2001).

Jannière et al., "Stable Gene Amplification in the Chromosome of *Bacillus subtilis*," *Gene* 40(1):47-55 (1985).

Jiang et al., "Molecular Mechanisms of Sweet Receptor Function," *Chem. Senses* 30(Suppl 1):i17-i18 (2005).

Jingami et al., "Structure of the Metabotropic Glutamate Receptor," *Curr. Opin. Neurobiol.* 13(3):271-278 (2003).

Johnson et al., "Knowledge-based Protein Modeling," *Crit. Rev. Biochem. Mol. Biol.* 29(1):1-68 (1994).

Jones & Reed, "$G_{olf}$—An Olfactory Neuron Specific-G Protein Involved in Odorant Signal Transduction," *Science* 244:790-795 (1989).

Jones et al., "Improved Methods for Building Protein Models in Electron Density Maps and the Location of Errors in These Models," *Acta Crystallogr. A* 47(pt 2):110-119 (1991).

Juilfs et al., "A Subset of Olfactory Neurons That Selectively Express cGMP-stimulated Phosphodiesterase (PDE2) and Guanylyl Cyclase-D Define a Unique Olfactory Signal Transduction Pathway," *Proc. Nat'l Acad. Sci. USA* 94:3388-3395 (1997).

Kakkar et al., "Calmodulin-dependent Cyclic Nucleotide Phosphodiesterase (PDE1)," *Cell Mol. Life Sci.* 55(8-9):1164-1186 (1999).

Kaplitt et al., "Expression of a Functional Foreign Gene in Adult Mammalian Brain Following in Vivo Transfer via a Herpes Simplex Virus Type 1 Defective Viral Vector," *Mol. Cell. Neurosci.* 2(4):320-330 (1991).

Karnik & Khorana, "Assembly of Functional Rhodopsin Requires a Disulfide Bond Between Cysteine Residues 110 and 187," *J. Biol. Chem.* 265(29):17520-17524 (1990).

Karnik et al., "Cysteine Residues 110 and 187 Are Essential for the Formation of Correct Structure in Bovine Rhodopsin," *Proc. Nat'l Acad. Sci. USA* 85:8459-8463 (1988).

Kawai et al., "Leptin as a Modulator of Sweet Taste Sensitivities in Mice," *Proc. Nat'l Acad. Sci. USA* 97:11044-11049 (2000).

Kieffer & Habener, "The Glucagon-like Peptides," *Endocrine Rev.* 20(6):876-913 (1999).

Kim & Smithies, "Recombinant Fragment Assay for Gene Targetting Based on the Polymerase Chain Reaction," *Nucl. Acids. Res.* 16(18):8887-8903 (1988).

Kim et al., "Changes in Ghrelin and Ghrelin Receptor Expression According to Feeding Status," *Neuroreport* 14(10):1317-1320 (2003).

Kincaid et al., "Differential Localization of Calmodulin-dependent Enzymes in Rat Brain: Evidence for Selective Expression of Cyclic Nucleotide Phosphodiesterase in Specific Neurons," *Proc. Nat'l Acad. Sci. USA* 84:1118-1122 (1987).

Kinnamon, S.C., "Taste Transduction: A Diversity of Mechanisms," *Trends. Neurosci.* 11(11):491-496 (1988).

Kinnamon & Cummings, "Chemosensory Transduction Mechanisms in Taste," *Annu. Rev. Physiol.* 54:715-731 (1992).

Kinnamon & Margolskee, "Mechanisms of Taste Transduction," *Curr. Opin. Neurobiol.* 6(4):506-513 (1996).

Kinnamon & Roper, "Membrane Properties of Isolated Mudpuppy Taste Cells," *J. Gen. Physiol.* 91:351-371 (1988).

Kinnamon et al., "Apical Localization of K+ Channels in Taste Cells Provides the Basis for Sour Taste Transduction," *Proc. Nat'l Acad. Sci. USA* 85:7023-7027 (1988).

Kishi et al., "Changes in Cell Morphology and Cell-to-cell Adhesion Induced by Extracellular $Ca^{2+}$ in Cultured Taste Bud Cells," *Biosci. Biotechnol. Biochem.* 66(2):484-487 (2002).

Kishi et al., "Primary Culture of Rat Taste Bud Cells That Retain Molecular Markers for Taste Buds and Permit Functional Expression of Foreign Genes," *Neurosci.* 106(1):217-225 (2001).

Kitagawa et al., "Molecular Genetic Identification of a Candidate Receptor Gene for Sweet Taste," *Biochem. Biophys. Res. Commun.* 283:236-242 (2001).

Köhler & Milstein, "Continuous Cultures of Fused Cells Secreting Antibody of Predefined Specificity," *Nature* 256:495-497 (1975).

Kohmura et al., "Assignment of the Disulfide Bonds in the Sweet Protein Brazzein," *Biopolymers* 38(4):553-556 (1996).

Kojima & Kangawa, "Ghrelin, an Orexigenic Signaling Molecule from the Gastrointestinal Tract," *Curr. Opin. Pharmacol.* 2:665-668 (2002).

Kojima et al., "Ghrelin is a Growth-hormone-releasing Acylated Peptide from Stomach," *Nature* 402:656-660 (1999).

Kolesnikov & Margolskee, "A Cyclic-nucleotide-suppressible Conductance Activated by Transducin in Taste Cells," *Nature* 376(6535):85-88 (1995).

Kolinski & Skolnick, "Assembly of Protein Structure from Sparse Experimental Data: An Efficient Monte Carlo Model," *Proteins* 32(4):475-494 (1998).

Komuro & Rakic, "In Vitro Analysis of Signal Mechanisms Involved in Neuronal Migration," in 4 The Neuron in Tissue Culture 57-69 (L.W. Haynes ed., 1999).

Komuro & Rakic, "Orchestration of Neuronal Migration by Activity of Ion Channels, Neurotransmitter Receptors, and Intracellular $Ca^{2+}$ Fluctuations," *J. Neurobiol.* 37(1):110-130 (1998).

König et al., "Three Cytoplasmic Loops of Rhodopsin Interact with Transducin," *Proc. Nat'l Acad. Sci. USA* 86:6878-6882 (1989).

Kozal et al., "Extensive Polymorphisms Observed in HIV-1 Clade B Protease Gene Using High-density Oligonucleotide Arrays," *Nat. Med.* 2(7):753-759 (1996).

Kozbor & Roder, "The Production of Monoclonal Antibodies from Human Lymphocytes," *Immunol. Today* 4(3):72-79 (1983).

Krarup & Groop, "Physiology and Pathophysiology of GIP: A Review," *Scand. J. Clin. Lab. Invest.* 51:571-579 (1991).

Krieg & Melton, "In Vitro RNA Synthesis with SP6 RNA Polymerase," *Methods Enzymol.* 155:397-415 (1987).

Michael Kriegler, Gene Transfer and Expression (1990) (Table of Contents only).

Krimpenfort et al., "Generation of Transgenic Dairy Cattle Using 'In Vitro' Embryo Production," *Biotechnol.* 9(9):844-847 (1991).

Kuang et al., "Molecular Similarities in the Ligand Binding Pockets of an Odorant Receptor and the Metabotropic Glutamate Receptors," *J. Biol. Chem.* 278(43):42551-42559 (2003).

Kunishima et al., "Structural Basis of Glutamate Recognition by a Dimeric Metabotropic Glutamate Receptor," *Nature* 407:971-977 (2000).

Kuntz et al., "A Geometric Approach to Macromolecule-Ligand Interactions," *J. Mol. Biol.* 161(2):269-288 (1982).

Kurihara & Koyama, "High Activity of Adenyl Cyclase in Olfactory and Gustatory Organs," *Biochem. Biophys. Res. Commun.* 48(1):30-34 (1972).

Kusakabe et al., "Comprehensive Study on G Protein α-Subunits in Taste Bud Cells, with Special Reference to the Occurrence of Gαi2 as a Major Gα Species," *Chem. Senses* 25:525-531 (2000).

Laemmli, U.K., "Cleavage of Structural Proteins During the Assembly of the Head of Bacteriophage T4," *Nature* 227:680-685 (1970).

Lakso et al., "Targeted Oncogene Activation by Site-specific Recombination in Transgenic Mice," *Proc. Nat'l Acad. Sci. USA* 89:6232-6236 (1992).

Lam et al., "A New Type of Synthetic Peptide Library for Identifying Ligand-binding Activity," *Nature* 354:82-84 (1991).

LaPorte et al., "Cross-linking of Iodine-125-labeled, Calcium-dependent Regulatory Protein to the $Ca^{2+}$-sensitive Phosphodiesterase Purified from Bovine Heart," *Biochem.* 18(13):2820-2825 (1979).

La Salle et al., "An Adenovirus Vector for Gene Transfer into Neurons and Glia in the Brain," *Science* 259(5097):988-990 (1993).

Lattman, E., "Use of the Rotation and Translation Functions," *Methods Enzymol.* 115:55-77 (1985).

Lavitrano et al., "Sperm Cells as Vectors for Introducing Foreign DNA into Eggs: Genetic Transformation of Mice," *Cell* 57:717-723 (1989).

Lebkowski et al., "Adeno-associated Virus: A Vector System for Efficient Introduction and Integration of DNA into a Variety of Mammalian Cell Types," *Mol. Cell. Biol.* 8(10):3988-3996 (1988).

Lemckert et al., "Gene Targeting in C57BL/6 ES Cells. Successful Germ Line Transmission Using Recipient BALB/c Blastocysts Developmentally Matured in Vitro," *Nucl. Acids Res.* 25(4):917-918 (1997).

Lerea et al., "Identification of Specific Transducin α Subunits in Retinal Rod and Cone Photoreceptors," *Science* 234(4772):77-80 (1986).

Li et al., "High-resolution Genetic Mapping of the Saccharin Preference Locus (Sac) and the Putative Sweet Taste Receptor (T1R1) Gene (Gpr70) to Mouse Distal Chromosome 4," *Mamm. Genome* 12(1):13-16 (2001).

Li et al., "Human Receptors for Sweet and Umami Taste," *Proc. Nat'l. Acad. Sci. USA* 99(7):4692-4696 (2002).

Liang et al., "Parallel Synthesis and Screening of a Solid Phase Carbohydrate Library," *Science* 274:1520-1522 (1996).

Lindemann, B., "Chemoreception: Tasting the Sweet and the Bitter," *Curr. Biol.* 6(10):1234-1237 (1996).

Lindemann, B., "Receptors and Transduction in Taste," *Nature* 413:219-225 (2001).

Lindemann, B., "Receptor Seeks Ligand: On the Way to Cloning the Molecular Receptors for Sweet and Bitter Taste," *Nat. Med.* 5(4):381-382 (1999).

Lindemann, B., "Taste Reception," *Physiolog. Rev.* 76(3):719-766 (1996).

Linder & Gilman, "Purification of Recombinant $G_{i\alpha}$ and $G_{o\alpha}$ Proteins from *Escherichia coli*," *Methods Enzymol.* 195:202-215 (1991).

Liu & Northup, "The Helical Domain of a G Protein α Subunit is a Regulator of Its Effector," *Proc. Nat'l Acad. Sci. USA* 95:12878-12883 (1998).

Liu et al., "Mechanism of Allosteric Regulation of the Rod cGMP Phosphodiesterase Activity by the Helical Domain of Transducin α Subunit," *J. Biol. Chem.* 273(51):34284-34292 (1998).

Lo, C.W., "Transformation by Iontophoretic Microinjection of DNA: Multiple Integrations Without Tandem Insertions," *Mol. Cell. Biol.* 3(10):1803-1814 (1983).

Lochrie et al., "Sequence of the α Subunit of Photoreceptor G Protein: Homologies Between Transducin, ras, and Elongation Factors," *Science* 228:96-99 (1985).

Lockhart et al., "Expression Monitoring by Hybridization to High-density Oligonucleotide Arrays," *Nat. Biotechnol.* 14:1675-1680 (1996).

Lorber & Shoichet, "Flexible Ligand Docking Using Conformational Ensembles," *Protein Sci.* 7:938-950 (1998).

Lum & Henkin, "Sugar Binding to Purified Fractions from Bovine Taste Buds and Epithelial Tissue," *Biochim. Biophys. Acta* 421:380-394 (1976).

Lush, I.E., "The Genetics of Tasting in Mice. III. Quinine," *Genet. Res. Comb.* 44:151-160 (1984).

Lush, I.E., "The Genetics of Tasting in Mice. IV. The Acetates of Raffinose, Galactose and β-Lactose," *Genet. Res. Comb.* 47:117-123 (1986).

Lush & Holland, "The Genetics of Tasting in Mice. V. Glycine and Cycloheximide," *Genet. Res. Comb.* 52:207-212 (1988).

Lush, I.E., "The Genetics of Tasting in Mice. VI. Saccharin, Acesulfame, Dulcin and Sucrose," *Genet. Res. Comb.* 53:95-99 (1989).

Lush et al., "The Genetics of Tasting in Mice. VII. Glycine Revisited, and the Chromosomal Location of *Sac* and *Soa*," *Genet. Res. Comb.* 66:167-174 (1995).

Lüthy et al., "Assessment of Protein Models with Three-dimensional Profiles," *Nature* 356:83-85 (1992).

Malherbe et al., "Mutational Analysis and Molecular Modeling of the Allosteric Binding Site of a Novel, Selective, Noncompetitive Antagonist of the Metabotropic Glutamate 1 Receptor," *J. Biol. Chem.* 278(10):8340-8347 (2003).

Manganiello et al., "Cyclic GMP-stimulated Cyclic Nucleotide Phosphodiesterases," *in* Cyclic Nucleotide Phosphodiesterases: Structure, Regulation and Drug Action 61-85 (Joe Beavo & Miles D. Houslay eds., 1990).

Mansour et al., "Disruption of the Proto-oncogene *int*-2 in Mouse Embryo-derived Stem Cells: A General Strategy for Targeting Mutations to Non-selectable Genes," *Nature* 336:348-352 (1988).

Margolskee, R.F., "Molecular Mechanisms of Bitter and Sweet Taste Transduction," *J. Biol. Chem.* 277(1):1-4 (2002).

Margolskee et al., Abstract 572, "$\alpha_{gust}$: A Novel G Protein from Rat Taste Cells," *FASEB J.* 6(1):A99 (1992).

Matson et al., "Biopolymer Synthesis on Polypropylene Supports: Oligonucleotide Arrays," *Anal. Biochem.* 224:110-116 (1995).

Matsunami et al., "A Family of Candidate Taste Receptors in Human and Mouse," *Nature* 404:601-604 (2000).

Max et al., "*Tas1r3*, Encoding a New Candidate Taste Receptor, Is Allelic to the Sweet Responsiveness Locus *Sac*," *Nat. Genet.* 28:58-63 (2001).

Maxam & Gilbert, "A New Method for Sequencing DNA," *Proc. Nat'l Acad. Sci. USA* 74(2):560-564 (1977).

Mazzoni et al., "Structural Analysis of Rod GTP-binding Protein, $G_t$," *J. Biol. Chem.* 266(21):14072-14081 (1991).

McGregor & Gravina, Abstract 57, "Studies on Compounds That Block Bitter Taste," *Chem. Senses* 26(8):1048 (2001).

McLaughlin et al., "α Gustducin: A Taste Cell Specific G Protein Subunit Closely Related to the α Transducins," *in* 6 Chemical Signals in Vertebrates 9-14 (Richard L. Doty & Dietland Müller-Schwarze eds., 1992).

McLaughlin et al., Abstract 438.9, "Cloning of Gustatory Specific G Proteins from Rat," *Ann. Mtg. Society Neurosci.* 17(1):1104 (1991).

McLaughlin et al., Abstract 184, "Gustducin: A Tasteful G Protein," *Chem. Senses* 17(5):667 (1992).

McLaughlin et al., "Gustducin and Transducin: A Tale of Two G Proteins," *Ciba Found. Symp.* 179:186-196; discussion 196-200 (1993).

McLaughlin et al., "Gustducin is a Taste-cell-specific G Protein Closely Related to the Transducins," *Nature* 357:563-569 (1992).

McLaughlin et al., "Molecular Cloning of G Proteins and Phosphodiesterases from Rat Taste Cells," *Physiol. Behav.* 56(6):1157-1164 (1994).

McVey et al., "Monitoring Receptor Oligomerization Using Time-resolved Fluorescence Resonance Energy Transfer and Bioluminescence Resonance Energy Transfer," *J. Biol. Chem.* 276(17):14092-14099 (2001).

Medynski et al., "Amino Acid Sequence of the α Subunit of Transducin Deduced from the cDNA Sequence," *Proc. Nat'l Acad. Sci. USA* 82(13):4311-4315 (1985).

Meng et al., "Automated Docking with Grid-based Energy Evaluation," *J. Comp. Chem.* 13(4):505-524 (1992).

Mezei, "Efficient Monte Carlo Sampling for Long Molecular Chains Using Local Moves, Tested on a Solvated Lipid Bilayer," *J. Chem. Phys.* 118(8):3874-3879 (2003).

Mezei, "Optimal Position of Solute for Simulations," *J. Comp. Chem.* 18:812-815 (1997).

Miller & Rosman, "Improved Retroviral Vectors for Gene Transfer and Expression," *BioTechniques* 7(9):980-982, 984, 989-990 (1989).

Ming & Hellekant, "Brazzein, a New High-potency Thermostable Sweet Protein from *Pentadiplandra brazzeana* B," *FEBS Lett.* 355(1):106-108 (1994).

Ming et al., "Blocking Taste Receptor Activation of Gustducin Inhibits Gustatory Responses to Bitter Compounds," *Proc. Nat'l. Acad. Sci. USA* 96:9903-9908 (1999).

Ming et al., "Characterization and Solubilization of Bitter-responsive Receptors That Couple to Gustducin," *Proc. Nat'l Acad. Sci USA*, 95:8933-8938 (1998).

Miranker & Karplus, "Functionality Maps of Binding Sites: A Multiple Copy Simultaneous Search Method," *Proteins* 11:29-34 (1991).

Mirny & Shakhnovich, "Protein Structure Prediction by Threading. Why It Works and Why It Does Not," *J. Mol. Biol.* 283(2):507-526 (1998).

Misaka et al., "Taste Buds Have A Cyclic Nucleotide-activated Channel, CNGgust," *J. Biol. Chem.* 272(36):22623-22629 (1997).

Misteli & Spector, "Applications of the Green Fluorescent Protein in Cell Biology and Biotechnology," *Nat. Biotechnol.* 15:961-964 (1997).

Montmayeur et al., "A Candidate Taste Receptor Gene Near a Sweet Taste Locus," *Nat. Neurosci.* 4(5):492-498 (2001).

Morris et al., "Stereochemical Quality of Protein Structure Coordinates," *Proteins* 12(4):345-364 (1992).

Morrison et al., "Chimeric Human Antibody Molecules: Mouse Antigen-binding Domains with Human Constant Region Domains," *Proc. Nat'l Acad. Sci. USA* 81:6851-6855 (1984).

Mumby et al., "G-protein α-Subunit Expression, Myristoylation, and Membrane Association in COS Cells," *Proc. Nat'l Acad. Sci. USA* 87:728-732 (1990).

Naim et al., "Adenylate Cyclase Responses to Sucrose Stimulation in Membranes of Pig Circumvallate Taste Papillae," *Comp. Biochem. Physiol. B* 100(3):455-458 (1991).

Naim et al., "Some Taste Substances are Direct Activators of G-proteins," *Biochem. J.* 297:451-454 (1994).

Nakashima & Ninomiya; "Increase in Inositol 1,4,5-Trisphosphate Levels of the Fungiform Papilla in Response to Saccharin and Bitter Substances in Mice," *Cell Physiol. Biochem.* 8:224-230 (1998).

Nathans, J., "Rhodopsin: Structure, Function, and Genetics," *Biochem.* 31(21):4923-4931 (1992).

Needham-VanDevanter et al., "Characterization of an Adduct Between CC-1065 and a Defined Oligodeoxynucleotide Duplex," *Nucl. Acids Res.* 12(15):6159-6168 (1984).

Neer et al., "Analysis of G-protein α and βγ Subunits by in Vitro Translation," *Methods Enzymol.* 237:226-239 (1994).

Nef & Nef, "Olfaction: Transient Expression of a Putative Odorant Receptor in the Avian Notochord," *Proc. Nat'l Acad. Sci. USA* 94:4766-4771 (1997).

Nelson et al., "An Amino-acid Taste Receptor," *Nature* 416:199-202 (2002).

Neuberger et al., "Recombinant Antibodies Possessing Novel Effector Functions," *Nature* 312:604-608 (1984).

Nicholls et al., "Protein Folding and Association: Insights from the Interfacial and Thermodynamic Properties of Hydrocarbons," *Proteins* 11(4):281-296 (1991).

Nielsen et al., "Sequence-selective Recognition of DNA by Strand Displacement with a Thymine-substituted Polyamide," *Science* 254(5037):1497-1500 (1991).

Ninomiya & Imoto, "Gurmarin inhibition of Sweet Taste Responses in Mice," *Am J. Physiol.* 268: R1019-R1025 (1995).

Ninomiya et al., "Differential Taste Responses of Mouse Chorda Tympani and Glossopharyngeal Nerves to Sugars and Amino Acids," *Neurosci. Lett.* 163:197-200 (1993).

Ninomiya et al., "Enhanced Gustatory Neural Responses to Sugars in the Diabetic db/db Mouse," *Am. J. Physiol.* 269:R930-R937 (1995).

Ninomiya et al., "Taste Receptor Mechanisms Influenced by a Gene on Chromosome 4 in Mice," *in* 3 Chemical Senses 267-278 (Charles J. Wysocki & Morley R. Kare eds., 1991).

Ninomiya et al., "Gustatory Neural Responses in Three Different Strains of Mice," *Brain Res.* 302(2):305-314 (1984).

Ninomiya et al., "Lack of Gurmarin Sensitivity of Sweet Taste Receptors Innervated by the Glossopharyngeal Nerve in C57BL Mice," *Am. J. Physiol.* 272(3 Pt 2):R1002-R1006 (1997).

Ninomiya et al., "Responses to Umami Substances in Taste Bud Cells Innervated by the Chorda Tympani and Glossopharyngeal Nerves," *J. Nutr.* 130:950S-953S (2000).

Ninomiya et al., "Sweet Taste Responses of Mouse Chorda Tympani Neurons: Existence of Gurmarin-sensitive and -Insensitive Receptor Components," *J. Neurophysiol.* 81:3087-3091 (1999).

Nishibata & Itai, "Automatic Creation of Drug Candidate Structures Based on Receptor Structure. Starting Point for Artificial Lead Generation," *Tetrahedron* 47(43):8985-8990 (1991).

Northrup et al., "Electrostatic Effects in the Brownian Dynamics of Association and Orientation of Heme Proteins," *J. Phys. Chem.* 91(23):5991-5998 (1987).

Northup et al., "The Guanine Nucleotide Activating Site of the Regulatory Component of Adenylate Cyclase," *J. Biol. Chem.* 257(19):11416-11423 (1982).

Nucleic Acid Hybridisation: A Practical Approach (B.D. Hames & S.J. Higgins eds., 1985) (Table of Contents only).

Offermanns & Simon, "G$\alpha_{15}$ and G$\alpha_{16}$ Couple a Wide Variety of Receptors to Phospholipase C," *J. Biol. Chem.* 270(25):15175-15180 (1995).

Ogura & Kinnamon, "IP$_3$-independent Release of Ca$^{2+}$ from Intracellular Stores: A Novel Mechanism for Transduction of Bitter Stimuli," *J. Neurophysiol.* 82(5):2657-2666 (1999).

Olson & Goodsell, "Automated Docking and the Search for HIV Protease Inhibitors," *SAR QSAR Environ. Res.* 8(3):273-285 (1998).

Orr-Weaver et al., "Yeast Transformation: A Model System for the Study of Recombination," *Proc. Nat'l Acad. Sci. USA* 78(10):6354-6358 (1981).

Ortiz et al., "Ab Initio Folding of Proteins Using Restraints Derived from Evolutionary Information," *Proteins* Suppl 3:177-185 (1999).

Ota & Nishikawa, "Feasibility in the Inverse Protein Folding Protocol," *Protein Sci.* 8:1001-1009(1999).

Paddison et al., "Stable Suppression of Gene Expression by RNAi in Mammalian Cells," *Proc. Nat'l Acad. Sci. USA* 99:1443-1448 (2002).

Pagano et al., "The Non-competitive Antagonists 2-Methyl-6-(phenylethynyl)pyridine and 7-Hydroxyiminocyclopropan[*b*]chromen-1α-carboxylic Acid Ethyl Ester Interect with Overlapping Binding Pockets in the Transmembrane Region of Group I Metabotropic Glutamate Receptors," *J. Biol. Chem.* 275(43):33750-33758 (2000).

Papayannopoulou et al., "Activation of Developmentally Mutated Human Globin Genes by Cell Fusion," *Science* 242:1056-1058 (1988).

Parmentier et al., "Conservation of the Ligand Recognition Site of Metabotropic Glutamate Receptors During Evolution," *Neuropharmacol.* 39(7):1119-1131 (2000).

Pav et al., "Microtube Batch Protein Crystallization: Applications to Human Immunodeficiency Virus Type 2 (HIV-2) Protease and Human Renin," *Proteins* 20(1):98-102 (1994).

Pearson & Regnier, "High-performance Anion-exchange Chromatography of Oligonucleotides," *J. Chrom.* 255:137-149 (1983).

Pelz et al., "Genetic Influences on Saccharin Preference of Mice," *Physiol. Behav.* 10:263-265 (1973).

Peterson, G.L., "A Simplification of the Protein Assay Method of Lowry et al. Which is More Generally Applicable," *Anal. Biochem.* 83(2):346-356 (1977).

Pitcher et al., "G Protein-coupled Receptor Kinases," *Annu. Rev. Biochem.* 67:653-692 (1998).

Price, S., "Phosphodiesterase in Tongue Epithelium: Activation by Bitter Taste Stimuli," *Nature* 241:54-55 (1973).

Rahmatullah & Robishaw, "Direct Interaction of the α and γ Subunits of the G Proteins," *J. Biol. Chem.* 269(5):3574-3580 (1994).

Raibaud et al., "A Technique for Integrating Any DNA Fragment into the Chromosome of *Escherichia coli*," *Gene* 29(1-2):231-241 (1984).

Rarick et al., "A Site on Rod G Protein α Subunit That Mediates Effector Activation," *Science* 256:1031-1033 (1992).

Ray, K., "Structure-function Relationships of the Family 3 G-protein-coupled Receptors," *Int. Arch. Biosci.* 2001:1027-1035 (2001).

Redington, "MOLFIT: A Computer Program for Molecular Superimposition," *Comput. Chem.* 16(3):217-222 (1992).

Reeck et al., "'Homology' in Proteins and Nucleic Acids: A Terminology Muddle and a Way Out of It," *Cell* 50(5):667 (1987).

Reimer et al., "A Human Cellular Model for Studying the Regulation of Glucagon-like Peptide-1 Secretion," *Endocrinol.* 142(10):4522-4528 (2001).

Rindi et al., "Development of Neuroendocrine Tumors in the Gastrointestinal Tract of Transgenic Mice," *Am. J. Pathol.* 136(6):1349-1363 (1990).

Ronnett & Moon, "G Proteins and Olfactory Signal Transduction," *Annu. Rev. Physiol.* 64:189-222 (2002).

Roper, S.D., "The Cell Biology of Vertebrate Taste Receptors," *Ann. Rev. Neurosci.* 12:329-353 (1989).

Rosenzvveig et al., "Possible Novel Mechanism for Bitter Taste Mediated Through cGMP," *J. Neurophysiol.* 81:1661-1665 (1999).

Rosická et al., "Ghrelin—A New Endogenous Growth Hormone Secretagogue," *Physiol. Res.* 51:435-441 (2002).

Rössler et al., "Identification of a Phospholipase C β Subtype in Rat Taste Cells," *Eur. J. Cell Biol.* 77:253-261 (1998).

Ruiz et al., "Maintenance of Rat Taste Buds in Primary Culture," *Chem. Senses* 26:861-873 (2001).

Ruiz-Avila et al., "An in Vitro Assay Useful to Determine the Potency of Several Bitter Compounds," *Chem. Senses* 25:361-368 (2000).

Ruiz-Avila et al., "Coupling of Bitter Receptor to Phosphodiesterase Through Transducin in Taste Receptor Cells," *Nature* 376:80-85 (1995).

Rybalkin et al., "Calmodulin-stimulated Cyclic Nucleotide Phosphodiesterase (PDE1C) Is Induced in Human Arterial Smooth Muscle Cells of the Synthetic, Proliferative Phenotype," *J. Clin. Invest.* 100(10):2611-2621 (1997).

Saiki et al., "Primer-directed Enzymatic Amplification of DNA with a Thermostable DNA Polymerase," *Science* 239:487-491 (1988).

Sainz et al., "Identification of a Novel Member of the T1R Family of Putative Taste Receptors," *J. Neurochem.* 77:896-903 (2001).

Sako et al., "Gustatory Information of Umami Substances in Three Major Taste Nerves," *Physiol. Behav.* 71:193-198 (2000).

Šali & Blundell, "Comparative Protein Modelling by Satisfaction of Spatial Restraints," *J. Mol. Biol.* 234(3):779-815 (1993).

Joseph Sambrook et al., 1-3 Molecular Cloning: A Laboratory Manual (2d ed. 1989) (Table of Contents only).

Samulski et al., "A Recombinant Plasmid from Which an Infectious Adeno-associated Virus Genome Can Be Excised in Vitro and Its Use to Study Viral Replication," *J. Virol.* 61(10):3096-3101 (1987).

Samulski et al., "Helper-free Stocks of Recombinant Adeno-associated Viruses: Normal Integration Does Not Require Viral Gene Expression," *J. Virol.* 63(9):3822-3828 (1989).
Sánchez & Šali, "Advances in Comparative Protein-structure Modelling," *Curr. Opin. Struct. Biol.* 7(2):206-214 (1997).
Sánchez & Šali, "Evaluation of Comparative Protein Structure Modeling by Modeller-3," *Proteins Suppl* 1:50-58 (1997).
Sánchez & Šali, "Large-scale Protein Structure Modeling of the *Saccharomyces cerevisiae* Genome," *Proc. Nat'l Acad. Sci. USA* 95:13597-13602 (1998).
Sanger et al., "DNA Sequencing with Chain-terminating Inhibitors," *Proc. Nat'l Acad. Sci. USA* 74(12):5463-5467 (1977).
Sato & Beidler, "Dependence of Gustatory Neural Response on Depolarizing and Hyperpolarizing Receptor Potentials of Taste Cells in the Rat," *Comp. Biochem. Physiol. A* 75(2):131-137 (1983).
Sato et al., "Amino Acid Mutagenesis of the Ligand Binding Site and the Dimer Interface of the Metabotropic Glutamate Receptor 1," *J. Biol. Chem.* 278(6):4314-4321 (2003).
Schaeren-Wiemers & Gerfin-Moser, "A Single Protocol to Detect Transcripts of Various Types and Expression Levels in Neural Tissue and Cultured Cells: In Situ Hybridization Using Digoxigenin-labelled cRNA Probes," *Histochem.* 100:431-440 (1993).
Scherer & Davis, "Replacement of Chromosome Segments with Altered DNA Sequences Constructed in Vitro," *Proc. Nat'l Acad. Sci. USA* 76(10):4951-4955 (1979).
Scheven et al., "In Vitro Osteoclast Generation from Different Bone Marrow Fractions, Including a Highly Enriched Haematopoietic Stem Cell Population," *Nature* 321:79-81 (1986).
Schiffman et al., "Amiloride Reduces the Taste Intensity of $Na^+$ and $Li^+$ Salts and Sweeteners," *Proc. Nat'l Acad. Sci. USA* 80:6136-6140 (1983).
Schiffman et al., "Bitterness of Sweeteners as a Function of Concentration," *Brain Res. Bull.* 36(5):505-513 (1995).
Schiffman & Cahn, "Multiple Receptor Sites Mediate Sweetness: Evidence from Cross Adaptation," *Pharmacol. Biochem. Behav.* 15(3):377-388 (1981).
Schmidt et al., "Specificity of G Protein $\beta$ and $\gamma$ Subunit Interactions," *J. Biol. Chem.* 267(20):13807-13810 (1992).
Schnare et al., "Comprehensive Comparison of Structural Characteristics in Eukaryotic Cytoplasmic Large Subunit (23 S-like) Ribosomal RNA," *J. Mol. Biol.* 256(4):701-719 (1996).
Scott & Smith, "Searching for Peptide Ligands with an Epitope Library," *Science* 249(4967):386-390 (1990).
Seibert et al., "Contribution of Opening and Bending Dynamics to Specific Recognition of DNA Damage," *J. Mol. Biol.* 330(4):687-703 (2003).
Seibert et al., "Role of DNA Flexibility in Sequence-dependent Activity of Uracil DNA Glycosylase," *Biochem.* 41(36):10976-10984 (2002).
Sharma & Wang, "Purification and Characterization of Bovine Lung Calmodulin-dependent Cyclic Nucleotide Phosphodiesterase," *J. Biol. Chem.* 261(30):14160-14166 (1986).
Shepherd, G.M., "Sensory Transduction: Entering the Mainstream of Membrane Signaling," *Cell* 67(5):845-851 (1991).
Shimazaki et al., "Photoaffinity Labeling of Thaumatin-binding Protein in Monkey *Circumvallate papillae,*" *Biochim. Biophys. Acta* 884:291-298 (1986).
Shingai & Beidler, "Response Characteristics of Three Taste Nerves in Mice," *Brain Res.* 335:245-249 (1985).
Simon et al., "Diversity of G Proteins in Signal Transduction," *Science* 252:802-808 (1991).
Skolnick et al., "Derivation of Protein-specific Pair Potentials Based on Weak Sequence Fragment Similarity," *Proteins* 38(1):3-16 (2000).
Smith & Margolis, "Taste Processing: Whetting Our Appetites," *Curr. Biol.* 9:R453-R455 (1999).
Smoluchowski, M., "Versuch einer Mathematischen Theorie der Koagulationskinetik Kolloider Lösungen," *Z. Phys. Chem.* 92:129-168 (1917).
Snyder et al., "Isolation, Expression and Analysis of Splice Variants of a Human $CA^{2+}$/Calmodulin-stimulated Phosphodiesterase (PDE1A)," *Cell. Signal.* 11(7):535-544 (1999).

Songyang et al., "SH2 Domains Recognize Specific Phosphopeptide Sequences," *Cell* 72:767-778 (1993).
Sonnenburg et al., "Identification, Quantitation, and Cellular Localization of PDE1 Calmodulin-stimulated Cyclic Nucleotide Phosphodiesterases," *Methods* 14(1):3-19 (1998).
Spickofsky et al., "Biochemical Analysis of the Transducin-Phosphodiesterase Interaction," *Nat. Struct. Biol.* 1(11):771-781 (1994).
Spielman et al., "A Rapid Method of Collecting Taste Tissue from Rats and Mice," *Chem. Senses* 14(6):841-846 (1989).
Spielman et al., Abstract 262, "G. Proteins and P.I. Turnover in Bitter Taste Signal Transduction in Mice," *Chem. Senses* 17(5):701-702 (1992).
Spielman et al., "Generation of Inositol Phosphates in Bitter Taste Transduction," *Physiol. Behav.* 56(6):1149-1155 (1994).
Spielman, "Gustducin and Its Role in Taste," *J. Dent. Res.* 77(4):539-544 (1998).
Spielman et al., "Rapid Kinetics of Second Messenger Production in Bitter Taste," *Am. J. Physiol.* 270:C926-C931 (1996).
Stewart et al., "New Perspectives in Gustatory Physiology: Transduction, Development, and Plasticity," *Am. J. Physiol.* 272(1 Pt. 1):C1-C26 (1997).
Stone et al., "Virus-mediated Transfer of Foreign DNA into Taste Receptor Cells," *Chem. Senses* 27:779-787 (2002).
Strader et al., "A Single Amino Acid Substitution in the $\beta$-Adrenergic Receptor Promotes Partial Agonist Activity from Antagonists," *J. Biol. Chem.* 264(28):16470-16477 (1989).
Strader et al., "Identification of Two Serine Residues Involved in Agonist Activation of the $\beta$-Adrenergic Receptor," *J. Biol. Chem.* 264(23):13572-13578 (1989).
Stratford-Perricaudet et al., "Widespread Long-term Gene Transfer to Mouse Skeletal Muscles and Heart," *J. Clin. Invest.* 90:626-630 (1992).
Strathmann et al., "Diversity of the G-protein Family: Sequences from Five Additional $\alpha$ Subunits in the Mouse," *Proc. Nat'l Acad. Sci. USA* 86:7407-7409 (1989).
Strathmann & Simon, "G Protein Diversity: A Distinct Class of $\alpha$ Subunits Is Present in Vertebrates and Invertebrates," *Proc. Nat'l Acad. Sci. USA* 87:9113-9117 (1990).
Striem et al., "Sweet Tastants Stimulate Adenylate Cyclase Coupled to GTP-binding Protein in Rat Tongue Membranes," *Biochem. J.* 260:121-126 (1989).
Stryer & Bourne, "G Proteins: A Family of Signal Transducers," *Annu. Rev. Cell Biol.* 2:391-419 (1986).
Sturm et al., "Appetite, Food Intake, and Plasma Concentrations of Cholecystokinin, Ghrelin, and Other Gastrointestinal Hormones in Undernourished Older Women and Well-nourished Young and Older Women," *J. Clin. Endocrinol. Metab.* 88(8):3747-3755 (2003).
Sugawara et al., "Profile of Nucleotides and Nucleosides of Human Milk," *J. Nutr. Sci. Vitaminol.* 41(4):409-418 (1995).
Szklarz & Halpert, "Use of Homology Modeling in Conjunction with Site-directed Mutagenesis for Analysis of Structure-function Relationships of Mammalian Cytochromes P450," *Life Sci.* 61(26):2507-2520 (1997).
Takami et al., "Human Taste Cells Express the G Protein $\alpha$-Gustducin and Neuron-specific Enolase," *Mol. Brain Res.* 22(1-4):193-203 (1994).
Takeda et al., "Construction of Chimaeric Processed Immunoglobulin Genes Containing Mouse Variable and Human Constant Region Sequences," *Nature* 314:452-454 (1985).
Tam, J.P. "Synthetic Peptide Vaccine Design: Synthesis and Properties of a High-Multiple Antigenic Peptide System," *Proc. Nat'l Acad. Sci. USA* 85:5409-5413 (1988).
Tanabe et al., "Primary Structure of the $\alpha$-Subunit of Transducin and Its Relationship to *ras* Proteins," *Nature* 315(6016):242-245 (1985).
Temussi, P.A., "Why Are Sweet Proteins Sweet? Interaction of Brazzein, Monellin and Thaumatin with the T1R2-T1R3 Receptor," *FEBS Lett.* 526(1-3):1-4 (2002).
Terrillon et al., "Oxytocin and Vasopressin V1a and V2 Receptors Form Constitutive Homo- and Heterodimers During Biosynthesis," *Mol. Endocrinol.* 17(4):677-691 (2003).

Thomas et al., "Identification of Synaptophysin as a Hexameric Channel Protein of the Synaptic Vesicle Membrane," *Science* 242(4881):1050-1053 (1988).

Thompson et al., "CLUSTAL W: Improving the Sensitivity of Progressive Multiple Sequence Alignment Through Sequence Weighting, Position-specific Gap Penalties and Weight Matrix Choice," *Nucl. Acids Res.* 22(22):4673-4680 (1994).

Thompson et al., "Germ Line Transmission and Expression of a Corrected HPRT Gene Produced by Gene Targeting in Embryonic Stem Cells," *Cell* 56:313-321 (1989).

Tonosaki & Funakoshi, "Cyclic Nucleotides May Mediate Taste Transduction," *Nature* 331:354-356 (1988).

Tonosaki & Funakoshi, "Cross-adapted Sugar Responses in the Mouse Taste Cell," *Comp. Biochem. Physiol. A* 92(2):181-183 (1989).

Tsuchiya et al., "Structural Views of the Ligand-binding Cores of a Metabotropic Glutamate Receptor Complexed with an Antagonist and Both Glutamate and $Gd^{3+}$," *Proc. Nat'l Acad. Sci. USA* 99(5):2660-2665 (2002).

Tsunenari et al., "Activation by Bitter Substances of a Cationic Channel in Membrane Patches Excised from the Bullfrog Taste Receptor Cell," *J. Physiol.* 519:397-404 (1999).

Turton et al., "A Role for Glucagon-like Peptide-1 in the Central Regulation of Feeding," *Nature* 379:69-72 (1996).

Uchida & Sato, "Changes in Outward $K^+$ Currents in Response to Two Types of Sweeteners in Sweet Taste Transduction of Gerbil Taste Cells," *Chem. Senses* 22(2):163-169 (1997).

Uchida & Sato, "Intracellular Calcium Increase in Gerbil Taste Cell by Amino Acid Sweeteners," *Chem. Senses* 22(1):83-91 (1997).

Van Der Putten et al., "Efficient Insertion of Genes into the Mouse Germ Line via Retroviral Vectors," *Proc. Nat'l Acad. Sci. USA* 82:6148-6152 (1985).

Vaughan et al., "Human Antibodies with Sub-nanomolar Affinities Isolated from a Large Non-immunized Phage Display Library," *Nat. Biotechnol.* 14:309-314 (1996).

Villa-Komaroff et al., "A Bacterial Clone Synthesizing Proinsulin," *Proc. Nat'l Acad. Sci. USA* 75(8):3727-3731 (1978).

Wagner et al., "Nucleotide Sequence of the Thymidine Kinase Gene of Herpes Simplex Virus Type 1," *Proc. Nat'l. Acad. Sci. USA* 78(3):1441-1445 (1981).

Walensky et al., "Two Novel Odorant Receptor Families Expressed in Spermatids Undergo 5'-Splicing," *J. Biol. Chem.* 273(16):9378-9387 (1998).

Walters, D.E., "Homology-based Model of the Extracellular Domain of the Taste Receptor T1R3," *Pure Appl. Chem.* 74(7):1117-1123 (2002).

Wang et al., "Calmodulin-stimulated Cyclic Nucleotide Phosphodiesterases," *in* Cyclic Nucleotide Phosphodiesterases: Structure, Regulation and Drug Action 19-59 (Joe Beavo & Miles D. Houslay eds., 1990).

Ward et al., "Binding Activities of a Repertoire of Single Immunoglobulin Variable Domains Secreted from *Escherichia coli*," *Nature* 341:544-546 (1989).

James D. Watson et al., 1 Molecular Biology of the Gene 606 (4$^{th}$ ed. 2001).

Weishaar et al., "A New Generation of Phosphodiesterase Inhibitors: Multiple Molecular Forms of Phosphodiesterase and the Potential for Drug Selectivity," *J. Med. Chem.* 28(5):537-545 (1985).

Wilkie et al., "Characterization of G-protein α Subunits in the $G_q$ Class: Expression in Murine Tissues and in Stromal and Hematopoietic Cell Lines," *Proc. Nat'l Acad. Sci. USA* 88:10049-10053 (1991).

Winslow et al., "Conformations of the $\alpha_{39}$, $\alpha_{41}$, and β γ Components of Brain Guanine Nucleotide-binding Proteins," *J. Biol. Chem.* 261(16):7571-7579 (1986).

Wishart et al., "Constrained Multiple Sequence Alignment Using XALIGN," *Comput. Appl. Biosci.* 10(6):687-688 (1994).

Wong et al., "Biochemical and Transgenic Analysis of Gustducin's Role in Bitter and Sweet Transduction," *Cold Spring Harbor Symp. Quant. Biol.* 61(2):173-184 (1996).

Wong et al., "Transduction of Bitter and Sweet Taste by Gustducin," *Nature* 381:796-800 (1996).

Immobilized Cells and Enzymes: A Practical Approach (Jonathan Woodward ed., 1985) (Table of Contents only).

Wu et al., "Expression of Bitter Taste Receptors of the T2R Family in the Gastrointestinal Tract and Enteroendocrine STC-1 Cells," *Proc. Nat'l. Acad. Sci. USA* 99(4):2392-2397 (2002).

Yamaguchi, "Basic Properties of Umami and Effects on Humans," *Physiol. Behav.* 49:833-841 (1991).

Yamamoto et al., "Identification of a Functional Promoter in the Long Terminal Repeat of Rous Sarcoma Virus," *Cell* 22(1):787-797 (1980).

Yan et al., "Bitter Taste Transduced by PLC-$\beta_2$-dependent Rise in $IP_3$ and α-Gustducin-dependent Fall in Cyclic Nucleotides," *Am. J. Physiol. Cell Physiol.* 280:C742-C751 (2001).

Yan et al., "The Calmodulin-dependent Phosphodiesterase Gene *PDE1C* Encodes Several Functionally Different Splice Variants in a Tissue-specific Manner," *J. Biol. Chem.* 271(41):25699-25706 (1996).

Yatsunami & Khorana, "GTPase of Bovine Rod Outer Segments: The Amino Acid Sequence of the α Subunit as Derived from the cDNA Sequence," *Proc. Nat'l Acad. Sci. USA* 82:4316-4320 (1985).

Yip & Wolfe, "GIP Biology and Fat Metabolism," *Life Sci.* 66(2):91-103 (2000).

Zhang et al., "The Extracellular Calcium-sensing Receptor Dimerizes Through Multiple Types of Intermolecular Interactions," *J. Biol. Chem.* 276(7):5316-5322 (2001).

Zhu et al., "Construction of Stable Laboratory and Industrial Yeast Strains Expressing a Foreign Gene by Integrative Transformation Using a Dominant Selection System," *Gene* 50(1-3):225--237 (1986).

Genbank Accession No. CO391213 (Jul. 1, 2004).
Genbank Accession No. BC076365 (Jul. 15, 2006).
Genbank Accession No. CO564040 (Jul. 19, 2004).
Genbank Accession No. CR607309 (Jul. 21, 2004).
Genbank Accession No. CL746986 (Jul. 27, 2004).
Genbank Accession No. AAX75819 (Apr. 5, 2005).
Genbank Accession No. BW925578 (Feb. 21, 2007).
Genbank Accession No. AAHY01167172 (Jul. 7, 2005).
Genbank Accession No. AAHX01474864 (Jul. 7, 2005).
Genbank Accession No. XP_731761 (Apr. 21, 2006).
Genbank Accession No. NW_676870 (Aug. 10, 2005).
Genbank Accession No. CZ945728 (Aug. 11, 2005).
Genbank Accession No. AAIY01480701 (Aug. 15, 2005).
Genbank Accession No. DQ120416 (Jan. 18, 2006).
Genbank Accession No. DT688588 (Sep. 12, 2005).
Genbank Accession No. DU489399 (Oct. 6, 2005).

* cited by examiner

FIG. 1B

| Nucleotide position | 135 | 163 | 179 | 182 | 186 | 264 | 270 | 312 | 652 | 692 | 965 | 969 | 1300 | 2647 | 2689 |
|---|---|---|---|---|---|---|---|---|---|---|---|---|---|---|---|
| C57BL/6J | A | A | T | C | T | - | A | T | T | T | A | C | G | T | T |
| FVB/N, SWR, ST/bJ | A | A | T | T | T | G | G | C | C | C | G | T | A | C | C |
| Non-taster strains | G | G | C | T | T | G | G | C | C | C | G | C | A | T | C |
| Coding change | s | T55A | I60T | P61L | s | i | s | i | i | s | s | C261R | R371Q | S692L | I706T |

```
           predicted leader sequence                        A  T          o o
mT1R3  -----MPALAIMGLSLAAFLELGMGASLCLSQQFKAQGDYILGGLFPLGSTEEATLN-QRTQPNSDPCNRFSP---LCLFLAMAMKMAV-80
rT1R1  ---MLFWAAHLLLSLQLVYCWAFSCQRTESSPGFSLPGDFLLAGLFSLHGDCLQV----RHRPLVTSCDRPDSFNGHGYHLFQAMRFTV
rT1R2  ----MGPQARTLCLLSLLLHVLPKPGKLVENSDFHLAGDYLLGGLFTLHANVKSIS--HLSYLQVPKCNEFTMKV-LGYNLMQAMRFAV
mECaSR --------MAWFGYCLALLALTWHSSAYGPDQRAQKKGDIILGGLFPIHFGVSAKDQDLKSRPESVECIRYNFR---GFRWLQAMIFAI
mGluR1 ..FFPMIFLEMSILPRMPDRKVLLAGASSQRSVARMDGDVIIGALFSVHHQPP------AEKVPERKCGEIREQ--YGIQRVEAMFHTL mT1R3  EEINNGSALLPGLRLGYDLFDTCSEPVVTMKSSLMFLAKVGSQ-----SIAAYCNY-------TQYQPRVLAVIGPHSSELALITGKFF-157
rT1R1  EEINNSSALLPNITLGYELYDVCSESANVYATLRVLALQGPR-----HIEIQKDL-------RNHSSKVVAFIGPDNTDHAVTTAALL
rT1R2  EEINNCSSLLPGVLLGYEMVDVCYLSNNIHPGLYFLAQDDD-----LLPILKDY-------SQYMPHVVAVIGPDNSESAITVSNIL
mECaSR EEINSSPALLPNMTLGYRIFDTCNTVSKALEATLSFVAQNKIDS---LNLDEFCNC------SEHIPSTIAVVGATGSGVSTAVANLL
mGluR1 DKINADPVLLPNITLGSEIRDSCWHSSVALEQSIEFIRDSLISIRDEKDGLNRCLPDGQTLPPGRTKKPIAGVIGPGSSSVAIQVQNLL o o                  o                      o
mT1R3  SFFLMPQVSYSASMDRLSDRETFPSFFRTVPSDRVQLAVVTLLQNFSWNWVAALGSDDDYGREGLSIFSS-LANARGICIAHEGLVPQ-246
rT1R1  GPFLMPLVSYEASSVVLSAKRKFPSFLRTVPSDRHQVEVMVQLLQSFGWNWISLIGSYGDYGQLGVQALEE-LAVPRGICVAFKDIVPF
rT1R2  SHFLIPQITYSAISDKLRDKRHFPSMLRTVPSATHHIEAMVQLMVHFQWNWIVVLVSDDDYGRENSHLLSQRLTKTSDICIAFQEVLPI
mECaSR GLFYIPQVSYASSSRLLSNKNQFKSFLRTIPNDEHQATAMADIIEYFRWNWVGTIAADDDYGRPGIEKFREEAEER-DICIDFSELISQ
mGluR1 QLFDIPQIAYSATSIDLSDKTLYKYFLRVVPSDTLQARAMLDIVKRYNWTYVSAVHTEGNYGESGMDAFKELAAQE-GLCIAHSDKIYS o              o  o
mT1R3  HDTS----GQQLGKVLDVLRQVNQSKVQVVVLFASARAVYSLFSYSIHHGLSPK-VWVASESWLTSDLVMTLPNIARVGTVLGFLQRGA-331
rT1R1  S-----ARVGDPR-MQSMMQHLAQARTTVVVFSNRHLARVFFRSVVLANLTGK-VWVASEDWAISTYITSVTGIQGIGTVLGVAVQQR
rT1R2  PESSQVMRSEEQRQLDNILDKLRRTSARVVVFSPELSLYSFFHEVLRWNFTG-FVWIASESWAIDPVLHNLTELRHTGTFLGVTIQRV
mECaSR Y--------SDEEEIQQVVEVIQNSTAKVIVVFSSGPDLEPLIKEIVRRNITGR-IWLASEAWASSSLIAMPEYFHVVGGTIGFGLKAG
mGluR1 N------AGEKSFDRLLRKLRERLPKARVVVCFCEGMTVRGLLSAMRRLGVVGEFSLIGSDGWADRDEVIEGYEVEANGGITIKLQSPE o
mT1R3  LLPEFSHYVE----------THLALAADPAFCASLNAELDLEEHV---------------MGQRCPRDDIMLQNLSSGLLQNLSAG-393
rT1R1  QVPGLKEFEE---------SYVRAVTAAPSACPEGSWSTC------------------NQLCRECHTFTTRNMPTLGAFSM
rT1R2  SIPGFSQFRV----RRDKPGYPVPNTTNLRTTC---------------------------NQDCDACLNTTKSFNNILILSGE
mECaSR QIPGFREFLQKVHPRKSVHNGFAKEFWEETFNCHLQDGAKGPLPVDTFVRSHEEGGNRLLNSSTAFRPLCTGDENINSVETPYMDYEHL
mGluR1 VRS-FDDYFLKLRLDTNTRNPWFPEFWQHRFQCRLPGHLL----------------ENPNFKKVCTGNESL--EENYVQDSK-- mT1R3  QLHHQIFATYAAVYSVAQALHNTLQ--CN-------VSHCHVSEHVLPWQLLENM-YNMSFHARDLTLQ-FDAECNVDMEYDLKMWVWQ-471
rT1R1  SAA---YRVYEAVYAVAHGLHQLLG--CT-------SEICSRG-PVYPWQLLQQI-YKVNFLLHENTVA-FDDNCDTLGYYDIIAWDWN
rT1R2  RVV---YSVYSAVYAVAHALHRLLG--CN-------RVRCTKQ-KVYPWQLLREI-WHVNFTLLGNRLF-FDQQGDMPLLLDIIQWQWD
mECaSR RIS---YNVYLAVYSIAHALQDIYT--CLPGRGLFTNGSCADIKKVEAWQVLKHLR-HLNFTNNMGEQVTFDECCDLVGNYSIINWHLS
mGluR1 ----MGF-VINAIYAMAHGLQNMHHALCPG-----HVGLCDAMKPIDGRKLLDFLI-KSSFVGVSGEEVWFDEKCDAPGRYDIMNLQYT mT1R3  SPTPVLHTVGTFNGT--------LQLQQSKMYWPG--NQVPVSQCSRQCKDGQVRRVKGFH-SCCYDCVDCKAGSYR-KHPDDFTCTPC-548
rT1R1  GPEWTFEIIGSASLSPVH-----LDINKTKIQWHGKNNQVPVSVCTTDCLAGHHRVVVGSH-HCCFECVPCEAGTFL-NMSELHICQPC
rT1R2  LSQNPFQSIASYSPTSKR-----LTYIN-NVSWYTPNNTVPVSMCSKSCQPGQMKKSVGLH-PCCFECLDCMPGTYLNRSADEFNCLSC
mECaSR PEDGSIVFKEVGYYNVYAKKGERLFINEGKILWSGFSREVPFSNCSRDCQAGTRKGIIEGEPTCCFECAECPDG-EYSGETDASACDKC
mGluR1 EAN-RYDYVHVGTWHEGV-----LNIDDYKIQMNK-SGMV-RSVCSEPCLKGQIKVIRKGEVSCCWICTACKENEFVQ---DEFTCRAC
```

FIG. 8A

```
TTGTTAGTGCTGGAGACTTCTACCTACCATGCCAGCTTTGGCTATCATGG
GTCTCAGCCTGGCTGCTTTCCTGGAGCTTGGGATGGGGCCTCTTTGTGT
CTGTCACAGCAATTCAAGGCACAAGGGGACTACATACTGGGCGGGCTATT
TCCCCTGGGCTCAACCGAGGAGGCCACTCTCAACCAGAGAACACAACCCA
ACAGCATCCCGTGCAACAGGTATGGAGGCTAGTAGCTGGGGTGGGAGTGA
ACCGAAGCTTGGCAGCTTTGGCTCCGTGGTACTACCAATCTGGGAAGAGG
TGGTGATCAGTTTCCATGTGGCCTCAGGTTCTCACCCCTTGGTTTGTTCC
TGGCCATGGCTATGAAGATGGCTGTGGAGGAGATCAACAATGGATCTGCC
TTGCTCCCTGGGCTGCGGCTGGGCTATGACCTATTTGACACATGCTCCGA
GCCAGTGGTCACCATGAAATCCAGTCTCATGTTCCTGGCCAAGGTGGGCA
GTCAAAGCATTGCTGCCTACTGCAACTACACAGTACCAACCCCGTGTG
CTGGCTGTCATCGGCCCCACTCATCAGAGCTTGCCCTCATTACAGGCAA
GTTCTTCAGCTTCTTCCTCATGCCACAGGTGAGCCCACTTCCTTTGTGTT
CTCAACCGATTGCACCCATTGAGCTCTCATATCAGAAGTGCTTCTTGAT
CACCACAGGTCAGCTATAGTGCCAGCATGGATCGGCTAAGTGACCGGGAA
ACGTTTCCATCCTTCTTCCGCACAGTGCCCAGTGACCGGGTGCAGCTGCA
GGCAGTTGTGACTCTGTTGCAGAACTTCAGCTGGAACTGGGTGGCCGCCT
TAGGGAGTGATGATGACTATGGCCGGGAAGGTCTGAGCATCTTTTCTAGT
CTGGCCAATGCACGAGGTATCTGCATCGCACATGAGGGCCTGGTGCCACA
ACATGACACTAGTGGCCAACAGTTGGGCAAGGTGCTGGATGTACTACGCC
AAGTGAACCAAAGTAAAGTACAAGTGGTGGTGCTGTTTGCCTCTGCCCGT
GCTGTCTACTCCCTTTTTAGTTACAGCATCCATCATGGCCTCTCACCCAA
GGTATGGGTGGCCAGTGAGTCTTGGCTGACATCTGACCTGGTCATGACAC
TTCCCAATATTGCCCGTGTGGGCACTGTGCTTGGGTTTTTGCAGCGGGGT
GCCCTACTGCCTGAATTTTCCCATTATGTGGAGACTCACCTTGCCCTGGC
CGCTGACCCAGCATTCTGTGCCTCACTGAATGCGGAGTTGGATCTGGAGG
AACATGTGATGGGGCAACGCTGTCCACGGTGTGACGACATCATGCTGCAG
AACCTATCATCTGGGCTGTTGCAGAACCTATCAGCTGGGCAATTGCACCA
CCAAATATTTGCAACCTATGCAGCTGTGTACAGTGTGGCTCAAGCCCTTC
ACAACACCCTACAGTGCAATGTCTCACATTGCCACGTATCAGAACATGTT
CTACCCTGGCAGGTAAGGGTAGGGTTTTTGCTGGGTTTTGCCTGCTCCT
GCAGGAACACTGAACCAGGCAGAGCCAAATCTTGTTGTGACTGGAGAGGC
CTTACCCTGACTCCACTCCACAGCTCCTGGAGAACATGTACAATATGAGT
TTCCATGCTCGAGACTTGACACTACAGTTTGATGCTGAAGGGAATGTAGA
CATGGAATATGACCTGAAGATGTGGGTGTGGCAGAGCCCTACACCTGTAT
TACATACTGTGGGCACCTTCAACGGCACCCTTCAGCTGCAGCAGTCTAAA
ATGTACTGGCCAGGCAACCAGGTAAGGACAAGACAGGCAAAAGGATGGT
GGGTAGAAGCTTGTCGGTCTTGGCCAGTGCTAGCCAAGGGGAGGCCTAA
CCCAAGGCTCCATGTACAGGTGCCAGTCTCCAGTGTTCCGCCAGTGCA
AAGATGGCCAGGTTCGCCGAGTAAAGGGCTTTCATTCCTGCTGCTATGAC
TGCGTGGACTGCAAGGCGGGCAGCTACCGGAAGCATCCAGGTGAACCGTC
TTCCCTAGACAGTCTGCACAGCCGGGCTAGGGGCAGAAGCATTCAAGTC
TGGCAAGCGCCCTCCCGCGGGCTAATGTGGAGACAGTTACTGTGGGGC
TGGCTGGGGAGGTCGGTCTCCATCAGCAGACCCCACATTACTTTTCTTC
CTTCCATCACTACAGATGACTTCACCTGTACTCCATGTAACCAGGACCAG
```

FIG. 8B

```
TGGTCCCCAGAGAAAAGCACAGCCTGCTTACCTCGCAGGCCCAAGTTTCT
GGCTTGGGGGGAGCCAGTTGTGCTGTCACTCCTCCTGCTGCTTTGCCTGG
TGCTGGGTCTAGCACTGGCTGCTCTGGGGCTCTCTGTCCACCACTGGGAC
AGCCCTCTTGTCCAGGCCTCAGGTGGCTCACAGTTCTGCTTTGGCCTGAT
CTGCCTAGGCCTCTTCTGCCTCAGTGTCCTTCTGTTCCCAGGGCGGCCAA
GCTCTGCCAGCTGCCTTGCACAACAACCAATGGCTCACCTCCCTCTCACA
GGCTGCCTGAGCACACTCTTCCTGCAAGCAGCTGAGACCTTTGTGGAGTC
TGAGCTGCCACTGAGCTGGGCAAACTGGCTATGCAGCTACCTTCGGGGAC
TCTGGGCCTGGCTAGTGGTACTGTTGGCCACTTTTGTGGAGGCAGCACTA
TGTGCCTGGTATTTGATCGCTTTCCCACCAGAGGTGGTGACAGACTGGTC
AGTGCTGCCCACAGAGGTACTGGAGCACTGCCACGTGCGTTCCTGGGTCA
GCCTGGGCTTGGTGCACATCACCAATGCAATGTTAGCTTTCCTCTGCTTT
CTGGGCACTTTCCTGGTACAGAGCCAGCCTGGCCGCTACAACCGTGCCCG
TGGTCTCACCTTCGCCATGCTAGCTTATTTCATCACCTGGGTCTCTTTTG
TGCCCCTCCTGGCCAATGTGCAGGTGGCCTACCAGCCAGCTGTGCAGATG
GGTGCTATCCTAGTCTGTGCCCTGGGCATCCTGGTCACCTTCCACCTGCC
CAAGTGCTATGTGCTTCTTTGGCTGCCAAAGCTCAACACCCAGGAGTTCT
TCCTGGGAAGGAATGCCAAGAAAGCAGCAGATGAGAACAGTGGCGGTGGT
GAGGCAGCTCAGGGACACAATGAATGACCACTGACCCGTGACCTTCCCTT
TAGGGAACCTAGCCCTACCAGAAATCTCCTAAGCCAACAAGCCCCGAATA
GTACCTCAGCCTGAGACGTGAGACACTTAACTATAGACTTGGACTCCACT
GACCTTAGCCTCACAGTGACCCCTTCCCCAAACCCCCAAGGCCTGCAGTG
CACAAGATGGACCCTATGAGCCCACCTATCCTTTCAAAGCAAGATTATCC
TTGATCCTATTATGCCCACCTAAGGCCTGCCCAGGTGACCCACAAAAGGT
TCTTTGGGACTTCATAGCCATACTTTGAATTCAGAAATTCCCCAGGCAGA
CCATGGGAGACCAGAAGGTACTGCTTGCCTGAACATGCCCAGCCCTGAGC
CCTCACTCAGCACCCTGTCCAGGCGTCCCAGGAATAGAAGGCTGGGCATG
TATGTGTGTGTGTGTGTGTGTGTGTGTGTGTGTGTGTGTGTGTATGTA
CGTATGTATGTATGTATCAGGACAGAACAAGAAAGACATCAGGCAGAGGA
CACTCAGGAGGTAGGCAACATCCAGCCTTCTCCATCCCTAGCTGAGCCCT
AGCCTGTAGGAGAGAACCAGGTCGCCGCCAGCACCTTGGACAGATCACAC
ACAGGGTGCGGGTCAGCACCACGGCCAGCGCCAGCCACGCGGGACCCCTG
GAATCAGCTTCTAGTACCAAGGACAGAAAAGTTGCCGCAAGGCCCCTTAC
TGGCCAGCACCAGGGACAGAGCCACATGCCTAAGCGGCAAGGGACAAGAG
CATCGTCCATCTGCAGGCAGGATCAGACCCGGGTCAGTTCTGGACTGGCC
CCACACCTGAATCCCGGAGCAGCTCAGCTGGAGAAAGAGAAACAAGCC
ACACATCAGTCCCATAAAATTAAACGCTTTTTTTAGTGTT
```

FIG. 9

```
1     ccatgccagc tttggctatc atgggtctca gcctggctgc tttcctggag cttgggatgg
61    gggcctcttt gtgtctgtca cagcaattca aggcacaagg ggactacata ctgggcgggc
121   tatttcccct gggctcaacc gaggaggcca ctctcaacca gagaacacaa cccaacagca
181   tcccgtgcaa caggtatgga ggctagtagc tggggtggga gtgaaccgaa gcttggcagc
241   tttggctccg tggtactacc aatctgggaa gaggtggtga tcagtttcca tgtggcctca
301   ggttctcacc ccttggtttg ttcctggcca tggctatgaa gatggctgtg gaggagatca
361   acaatggatc tgccttgctc cctgggctgc ggctgggcta tgacctattt gacacatgct
421   ccgagccagt ggtcaccatg aaatccagtc tcatgttcct ggccaaggtg ggcagtcaaa
481   gcattgctgc ctactgcaac tacacacagt accaacccg tgtgctggct gtcatcggcc
541   cccactcatc agagcttgcc ctcattacag gcaagttctt cagcttcttc ctcatgccac
601   aggtgagccc acttcctttg tgttctcaac cgattgcacc cattgagctc tcatatcaga
661   aagtgcttct tgatcaccac aggtcagcta tagtgccagc atggatcggc taagtgaccg
721   ggaaacgttt ccatccttct tccgcacagt gcccagtgac cgggtgcagc tgcaggcagt
781   tgtgactctg ttgcagaact tcagctggaa ctgggtggcc gccttaggga gtgatgatga
841   ctatggccgg gaaggtctga gcatcttttc tagtctggcc aatgcacgag gtatctgcat
901   cgcacatgag ggcctggtgc cacaacatga cactagtggc caacagttgg caaggtgct
961   ggatgtacta cgccaagtga accaaagtaa agtacaagtg gtggtgctgt tgcctctgc
1021  ccgtgctgtc tactcccttt ttagttacag catccatcat ggcctctcac ccaaggtatg
1081  ggtggccagt gagtcttggc tgacatctga cctggtcatg acacttccca atattgcccg
1141  tgtgggcact gtgcttgggt ttttgcagcg gggtgcccta ctgcctgaat tttcccatta
1201  tgtggagact caccttgccc tggccgctga cccagcattc tgtgcctcac tgaatgcgga
1261  gttggatctg gaggaacatg tgatggggca acgctgtcca cggtgtgacg acatcatgct
1321  gcagaaccta tcatctgggc tgttgcagaa cctatcagct gggcaattgc caccaaat
1381  atttgcaacc tatgcagctg tgtacagtgt ggctcaagcc ttcacaaca cctacagtg
1441  caatgtctca cattgccacg tatcagaaca tgttctaccc tggcaggtaa gggtagggtt
1501  ttttgctggg ttttgcctgc tcctgcagga acactgaacc aggcagagcc aaatcttgtt
1561  gtgactggag aggccttacc ctgactccac tccacagctc ctggagaaca tgtacaatat
1621  gagtttccat gctcgagact tgacactaca gtttgatgct gaagggaatg tagacatgga
1681  atatgacctg aagatgtggg tgtggcagag ccctacacct gtattacata ctgtgggcac
1741  cttcaacggc acccttcagc tgcagcagtc taaaatgtac tggccaggca accaggtaag
1801  gacaagacag gcaaaaagga tggtgggtag aagcttgtcg gtcttgggcc agtgctagcc
1861  aaggggaggc ctaacccaag gctccatgta caggtgccag tctcccagtg ttcccgccag
1921  tgcaaagatg gccaggttcg ccgagtaaag ggctttcatt cctgctgcta tgactgcgtg
1981  gactgcaagg cgggcagcta ccggaagcat ccaggtgaac cgtcttccct agacagtctg
2041  cacagccggg ctaggggca gaagcattca agtctggcaa gcgccctccc gcggggctaa
2101  tgtggagaca gttactgtgg gggctggctg gggaggtcgg tctcccatca gcagacccca
2161  cattactttt cttccttcca tcactacaga tgacttcacc tgtactccat gtaaccagga
2221  ccagtggtcc ccagagaaaa gcacagcctg cttacctcgc aggcccaagt ttctggcttg
2281  gggggagcca gttgtgctgt cactcctcct gctgctttgc ctggtgctgg gtctagcact
2341  ggctgctctg gggctctctg tccaccactg ggacagccct cttgtccagg cctcaggtgg
2401  ctcacagttc tgctttggcc tgatctgcct aggcctcttc tgcctcagtg tccttctgtt
2461  cccaggacgg ccaagctctg ccagctgcct tgcacaacaa ccaatggctc acctccctct
2521  cacaggctgc ctgagcacac tcttcctgca agcagctgag acctttgtgg agtctgagct
2581  gccactgagc tgggcaaact ggctatgcag ctaccttcgg ggactctggg cctggctagt
2641  ggtactgttg gccacttttg tggaggcagc actatgtgcc tggtatttga tcgctttccc
2701  accagaggtg gtgacagact ggtcagtgct gcccacagag gtactggagc actgccacgt
2761  gcgttcctgg gtcagcctgg gcttggtgca catcaccaat gcaatgttag cttttcctctg
2821  ctttctgggc actttcctgg tacagagcca gcctggccgc tacaaccgtg cccgtggtct
2881  caccttcgcc atgctagctt atttcatcac ctgggtctct ttgtgcccc tcctggccaa
2941  tgtgcaggtg gcctaccagc cagctgtgca gatgggtgct atcctagtct gtgccctggg
3001  catcctggtc accttccacc tgcccaagtg ctatgtgctt ctttggctgc aaagctcaa
3061  cacccaggag ttcttcctgg gaaggaatgc caagaaagca gcagatgaga acagtggcgg
3121  tggtgaggca gctcaggaac acaatgaatg acc
```

T1R3 TRANSGENIC ANIMALS, CELLS AND RELATED METHODS

This application is a continuation-in-part of U.S. patent application Ser. No. 10/475,620, filed Apr. 29, 2004 now abandoned, which is a U.S. National of PCT/US02/12656, filed Apr. 22, 2002, which claims benefit of U.S. Provisional Patent Application Ser. No. 60/285,209, filed Apr. 20, 2001, all of which are hereby incorporated by reference in their entirety.

This invention was made with government support under grant numbers MH57241, DC00310, DC003055, DC003155, and DC004766 awarded by the National Institutes of Health. The government has certain rights in this invention.

BACKGROUND

The present invention relates to the discovery, identification and characterization of a G protein coupled receptor, referred to herein as T1R3, which is expressed in taste receptor cells and associated with the perception of sweet taste. The invention encompasses T1R3 nucleotides, host cell expression systems, T1R3 proteins, fusion proteins, polypeptides and peptides, antibodies to the T1R3 protein, transgenic animals that express a T1R3 transgene, and recombinant "knock-out" animals that do not express T1R3.

Also within the scope of the present invention are transgenic cells that are heterozygous or homozygous for a nonfunctional T1R3 gene. The invention also encompasses methods of producing T1R3 transgenic animals and cells, particularly transgenic animals and cells that express a non-native T1R3 protein, and knock-out animals and cells.

The invention further relates to methods for identifying modulators of the T1R3-mediated taste response and the use of such modulators to either inhibit or promote the perception of sweetness. The modulators of T1R3 activity may be used as flavor enhancers in foods, beverages and pharmaceuticals.

The sense of taste plays a critical role in the life and nutritional status of humans and other organisms. Human taste perception may be categorized according to four well-known and widely accepted descriptors, sweet, bitter, salty and sour (corresponding to particular taste qualities or modalities), and two more controversial qualities: fat and amino acid taste. The ability to identify sweet tasting foodstuffs is particularly important as it provides vertebrates with a means to seek out needed carbohydrates with high nutritive value. The perception of bitter, on the other hand, is important for its protective value, enabling humans to avoid a plethora of potentially deadly plant alkaloids and other environmental toxins such as ergotamine, atropine and strychnine. During the past few years a number of molecular studies have identified components of bitter-responsive transduction cascades, such as α-gustducin (McLaughlin, S. K. et al., *Nature*, 357: 563-569 (1992); Wong, G. T. et al., *Nature*, 381: 796-800 (1996)), Gγ13 (Huang, L. et al., *Nat. Neurosci.*, 2: 1055-1062 (1999)) and the T2R/TRB receptors (Adler, E. et al., *Cell*, 10: 693-702 (2000); Chandrashekar, J. et al., *Cell*, 100: 703-711 (2000); Matsunami, H. et al., *Nature*, 404: 601-604 (2000)).

Meanwhile, umami taste seems to be mediated by modified versions of metabotropic glutamate receptors (mGluRs) known as mGluR4 (Chaudhari and Roper, *Ann. N Y Acad. Sci.*, 855: 398-406 (1998)) and by G-protein-coupled receptors (GPCRs) at the cell surface.

However, the components of sweet taste transduction have not been identified so definitively (Lindemann, B., *Physiol. Rev.*, 76: 719-766 (1996); Gilbertson, T. A. et al., *Curr. Opin. Neurobiol.*, 10: 519-527 (2000)), and the elusive sweet-responsive receptors have neither been cloned nor physically characterized.

Based on biochemical and electrophysiological studies of taste cells the following two models for sweet transduction have been proposed and are widely accepted (Lindemann, B., *Physiol. Rev.*, 76: 719-766 (1996); Gilbertson, T. A. et al., *Curr. Opin. Neurobiol.*, 10: 519-527 (2000)). First, a GPCR-$G_s$-cAMP pathway-sugars are thought to bind to and activate one or more G protein coupled receptors (GPCRs) linked to $G_s$; receptor-activated $G\alpha_s$ activates adenylyl cyclase (AC) to generate cAMP; cAMP activates protein kinase A which phosphorylates a basolateral K+ channel, leading to closure of the channel, depolarization of the taste cell, voltage-dependent $Ca^{2+}$ influx and neurotransmitter release. Second, a GPCR-$G_q$/Gβγ-$IP_3$ pathway-artificial sweeteners presumably bind to and activate one or more GPCRs coupled to PLCβ2 by either the α subunit of $G_q$ or by Gβγ subunits; activated $G\alpha_q$ or released Gβγ activates PLCβ2 to generate inositol trisphosphate ($IP_3$) and diacyl glycerol (DAG); $IP_3$ and DAG elicit $Ca^{2+}$ release from internal stores, leading to depolarization of the taste cell and neurotransmitter release. Progress in this field has been limited by the inability to clone sweet-responsive receptors.

Genetic studies in mice have identified two loci, sac (determines behavioral and electrophysiological responsiveness to saccharin, sucrose and other sweeteners) and dpa (determines responsiveness to D-phenylalanine), that provide major contributions to differences between sweet-sensitive and sweet-insensitive strains of mice (Fuller, J. L., *J. Hered*, 65: 33-36 (1974); Lush, I. E., *Genet. Res.*, 53: 95-99 (1989); Capeless, C. G. and Whitney, G., *Chem Senses*, 20: 291-298 (1995); Lush, I. E. et al., *Genet. Res.*, 66: 167-174 (1995)). Sac has been mapped to the distal end of mouse chromosome 4, and dpa mapped to the proximal portion of mouse chromosome 4 (Ninomiya, Y. et al., In *Chemical Senses*, vol. 3, Genetics of Perception and Communication (ed. C. J. Wysocki and M. R. Kare, New York: Marcel Dekker), pp. 267-278 (1991); Bachmanov, A. A. et al., *Mammal Genome*, 8: 545-548 (1977); Blizzard, D. A. et al., *Chem Senses*, 24: 373-385 (1999); Li, X. et al., *Genome*, 12: 13-16 (2001)). The orphan taste receptor T1R1 was tentatively mapped to the distal region of chromosome 4, hence, it was proposed as a candidate for sac (Hoon, M. A. et al., *Cell*, 96: 541-551 (1999)). However, detailed analysis of the recombination frequency between T1R1 and markers close to sac in F2 mice indicates that T1R1 is rather distant from sac (~5 cM away according to genetic data of Li et al. (Li, X. et al., *Genome*, 12: 13-16 (2001)); and more than a million base pairs away from D18346, the marker closest to sac. Another orphan taste receptor, T1R2, also maps to mouse chromosome 4, however, it is even further away from D18346/sac than is T1R1.

To thoroughly understand the molecular mechanisms underlying taste sensation, it is important to identify each molecular component in the taste signal transduction pathways. The present invention relates to the cloning of a G protein coupled receptor, T1R3, that is believed to be involved in taste transduction and may be involved in the changes in taste cell responses associated with sweet taste perception.

The present invention also encompasses non-human transgenic animals that do not express functional T1R3 protein, particularly knock-out animals, and transgenic animals that express a non-native T1R3 protein. Also within the scope of the invention are cells that do not express functional T1R3 protein, particularly knock-out cells, and transgenic cells that express a non-native T1R3 protein. Experimental model systems based on these animals and cells can be used to further define the role of the T1R3 receptor and its responses to different types of tastants and taste modulators, furthering our understanding of the molecular biology and biochemistry of taste. Such model systems would also be useful for screening for novel tastants, enhancers of desirable flavors, and blockers of undesirable flavors.

SUMMARY OF THE INVENTION

The present invention relates to the discovery, identification and characterization of a novel G protein coupled receptor referred to hereafter as T1R3, that participates in the taste signal transduction pathway. T1R3 is a receptor protein with a high degree of structural similarity to the family 3 G protein coupled receptors (hereinafter GPCR). As demonstrated by Northern Blot analysis, expression of the T1R3 transcript is tightly regulated, with the highest level of gene expression found in taste tissue. In situ hybridization indicates that T1R3 is selectively expressed in taste receptor cells, but is absent from the surrounding lingual epithelium, muscle or connective tissue. Moreover, T1R3 is highly expressed in taste buds from fungiform, foliate and circumvallate papillae.

The present invention encompasses T1R3 nucleotides, host cells expressing such nucleotides and the expression products of such nucleotides. The invention encompasses T1R3 protein, T1R3 fusion proteins, antibodies to the T1R3 receptor protein and transgenic animals that express a T1R3 transgene or recombinant knock-out animals that do not express the T1R3 protein.

The present invention also provides transgenic cells that express a T1R3 transgene or recombinant knock-out cells that do not express the T1R3 protein. The present invention also encompasses methods of producing the transgenic animals and cells.

Further, the present invention also relates to screening methods that utilize the T1R3 gene and/or T1R3 gene products as targets for the identification of compounds which modulate, i.e., act as agonists or antagonists, of T1R3 activity and/or expression. Compounds which stimulate taste responses similar to those of sweet tastants can be used as additives to act as flavor enhancers in foods, beverages or pharmaceuticals by increasing the perception of sweet taste. Compounds which inhibit the activity of the T1R3 receptor may be used to block the perception of sweetness.

Also within the scope of the present invention are methods of using T1R3 transgenic animals and cells, particularly knock-out animals and cells, to identify novel tastants and taste modulators. The present invention also provides methods of using transgenic animals and cells to further define T1R3-mediated signal transduction and the response of the T1R3 receptor to various tastants and taste modulators.

The invention is based, in part, on the discovery of a GPCR expressed at high levels in taste receptor cells. In taste transduction, sweet compounds are thought to act via a second messenger cascade utilizing PLCβ2 and IP$_3$. Colocalization of α-gustducin, PLCβ$_2$, gβ3 and Gγ13 and T1R3 to one subset of taste receptor cells indicates that they may function in the same transduction pathway.

The present invention relates to a transgenic non-human mammal heterozygous or homozygous for a nonfunctional T1R3 gene.

In some embodiments, the transgenic mammal is essentially free of any functional T1R3 protein.

In some embodiments, the T1R3 gene in the transgenic mammal's germ or somatic cells has been disrupted by recombination with a heterologous nucleotide sequence.

In some embodiments, expression of the T1R3 gene has been disrupted by RNA interference.

In some embodiments, transgenic mammal is a mouse.

In some embodiments, the transgenic mammal exhibits an impaired response to a sweet tastant. In some embodiments, the sweet tastant is a natural sweetener selected from glucose, sucrose, maltose, fructose, trehalose, sorbitol and D-tryptophan. In some embodiments, the sweet tastant is an artificial sweetener selected from sucralose, saccharin, acesulfame K and SC45647.

In some embodiments, the transgenic mammal exhibits an impaired response to an umami tastant. In some embodiments, the umami tastant is monosodium glutamate, inosine monophosphate or a combination thereof.

In some embodiments, the transgenic mammal exhibits an altered nerve response to a tastant. In some embodiments, the tastant is a sweet tastant. In some embodiments, the tastant is an umami tastant.

In some embodiments, the transgenic mammal is heterozygous or homozygous for a non-native T1R3 gene. In some embodiments, the transgenic mammal is capable of expressing a non-native T1R3 protein. In some embodiments, the transgenic mammal is a mouse and the T1R3 gene is native to a human, an ape or an old world monkey.

The present invention also relates to a transgenic non-human mammalian cell heterozygous or homozygous for a nonfunctional T1R3 gene.

In some embodiments, the cell is murine.

In some embodiments, the cell is heterozygous or homozygous for a non-native T1R3 gene. In some embodiments, the cell is capable of expressing a non-native T1R3 protein. In some embodiments, the cell is murine and the T1R3 gene is native to a human, an ape or an old world monkey.

In some embodiments of any of the cells described above, the cell is a taste cell or a gastrointestinal cell.

The present invention also relates to a method of producing a transgenic non-human mammal with a nonfunctional T1R3 gene, which comprises the steps of:

(a) constructing a targeting molecule comprising a disrupting nucleotide sequence flanked by sequences specific to or neighboring the T1R3 gene;

(b) introducing the targeting molecule into a non-human mammalian embryonic stem cell; and (c) using a transformed cell having a T1R3 gene rendered nonfunctional by homologous recombination with the targeting molecule or a fragment thereof to produce a transgenic mammal characterized by cells with the nonfunctional T1R3 gene.

In some embodiments, the method of producing the transgenic mammal further comprises the step of:

(d) breeding transgenic mammals carrying the nonfunctional T1R3 gene to produce descendants homozygous for the nonfunctional T1R3 gene.

The present invention also relates to a method of identifying a modulator of T1R3-mediated signal transduction, comprising the steps of:

(a) administering a test compound or mixture of compounds to a transgenic non-human mammal, wherein the transgenic mammal is heterozygous or homozygous for a nonfunctional T1R3 gene, and evaluating the effect of the test compound or mixture of compounds on the transgenic mammal;

(b) in a separate experiment, administering the test compound or mixture of compounds to a T1R3-expressing non-human mammal, and evaluating the effect of the test compound or mixture of compounds on the T1R3-expressing mammal; and (c) comparing the effect in step (a) with the effect in step (b), wherein a difference in effect indicates that the test compound or mixture of compounds modulates T1R3-mediated signal transduction.

The present invention also relates to a method of determining whether a tastant affects T1R3-mediated signal transduction, comprising the steps of:

(a) administering a tastant to a transgenic non-human mammal, wherein the transgenic mammal is heterozygous or homozygous for a nonfunctional T1R3 gene, and evaluating the effect of the tastant on the transgenic mammal;

(b) in a separate experiment, administering the tastant to a T1R3-expressing non-human mammal, and evaluating the effect of the tastant on the T1R3-expressing mammal; and (c) comparing the effect in step (a) with the effect in step (b), wherein a difference in effect indicates that the tastant affects T1R3-mediated signal transduction.

The present invention also relates to a method of identifying a modulator of T1R3-mediated signal transduction, comprising the steps of:

(a) administering a test compound or mixture of compounds to a transgenic non-human mammalian cell, wherein the cell is heterozygous or homozygous for a nonfunctional T1R3 gene, and evaluating the effect of the test compound or mixture of compounds on the cell;

(b) in a separate experiment, administering the test compound or mixture of compounds to a T1R3-expressing non-human mammalian cell, and evaluating the effect of the test compound or mixture of compounds on the cell; and (c) comparing the effect in step (a) with the effect in step (b), wherein a difference in effect indicates that the test compound or mixture of compounds modulates T1R3-mediated signal transduction.

The present invention also relates to a method of determining whether a tastant affects T1R3-mediated signal transduction, comprising the steps of:

(a) administering a tastant to a transgenic non-human mammalian cell, wherein the cell is heterozygous or homozygous for a nonfunctional T1R3 gene, and evaluating the effect of the tastant on the cell;

(b) in a separate experiment, administering the tastant to a T1R3-expressing non-human mammalian cell, and evaluating the effect of the tastant on the cell; and (c) comparing the effect in step (a) with the effect in step (b), wherein a difference in effect indicates that the tastant affects T1R3-mediated signal transduction.

The present invention also relates to a method of identifying a modulator of T1R3-mediated signal transduction, comprising the steps of:

(a) administering a test compound or mixture of compounds to a tissue slice derived from a transgenic non-human mammal, wherein the transgenic mammal is heterozygous or homozygous for a nonfunctional T1R3 gene, and evaluating the effect of the test compound or mixture of compounds on the tissue slice;

(b) in a separate experiment, administering the test compound or mixture of compounds to a tissue slice derived from a T1R3-expressing non-human mammal, and evaluating the effect of the test compound or mixture of compounds on the tissue slice; and (c) comparing the effect in step (a) with the effect in step (b), wherein a difference in effect indicates that the test compound or mixture of compounds modulates T1R3-mediated signal transduction.

The present invention also relates to a method of determining whether a tastant affects T1R3-mediated signal transduction, comprising the steps of:

(a) administering a tastant to a tissue slice derived from a transgenic non-human mammal, wherein the transgenic mammal is heterozygous or homozygous for a nonfunctional T1R3 gene, and evaluating the effect of the tastant on the tissue slice;

(b) in a separate experiment, administering the tastant to a tissue slice derived from a T1R3-expressing non-human mammal, and evaluating the effect of the tastant on the tissue slice; and (c) comparing the effect in step (a) with the effect in step (b), wherein a difference in effect indicates that the tastant affects T1R3-mediated signal transduction.

The present invention also relates to a method of identifying a modulator of T1R3-mediated signal transduction, comprising the steps of:

(a) administering a test compound or mixture of compounds to a taste bud derived from a transgenic non-human mammal, wherein the transgenic mammal is heterozygous or homozygous for a nonfunctional T1R3 gene, and evaluating the effect of the test compound or mixture of compounds on the taste bud;

(b) in a separate experiment, administering the test compound or mixture of compounds to a taste bud derived from a T1R3-expressing non-human mammal, and evaluating the effect of the test compound or mixture of compounds on the taste bud; and (c) comparing the effect in step (a) with the effect in step (b), wherein a difference in effect indicates that the test compound or mixture of compounds modulates T1R3-mediated signal transduction.

The present invention also relates to a method of determining whether a tastant affects T1R3-mediated signal transduction, comprising the steps of:

(a) administering a tastant to a taste bud derived from a transgenic non-human mammal, wherein the transgenic mammal is heterozygous or homozygous for a nonfunctional T1R3 gene, and evaluating the effect of the tastant on the taste bud;

(b) in a separate experiment, administering the tastant to a taste bud derived from a T1R3-expressing non-human mammal, and evaluating the effect of the tastant on the taste bud; and (c) comparing the effect in step (a) with the effect in step (b), wherein a difference in effect indicates that the tastant affects T1R3-mediated signal transduction.

In some embodiments of the methods described above, the effects are assessed using a behavioral assay.

In some embodiments of the methods described above, the effects are assessed by electrophysiological measurement of neural activity.

In some embodiments of the methods described above, the effects are assessed by examining levels of cAMP, cGMP, $IP_3$, DAG or PDE.

In some embodiments of the methods described above, the effects are assessed by examining levels of ions, phosphorylation, dephosphorylation or transcription. In some embodiments, the effects are assessed by $Ca^{2+}$ imaging. In some embodiments, the effects are assessed by patch-clamp recordings.

In some embodiments of the methods described above, the tastant is a sweet tastant. In some embodiments of the methods described above, the tastant is an umami tastant.

DEFINITIONS AND GENERAL TECHNIQUES

Unless defined otherwise, all technical and scientific terms used herein have the same meaning as commonly understood by one of ordinary skill in the art. In case of conflict, the present application including the definitions will control. Also, unless otherwise required by context, singular terms shall include pluralities, and plural terms shall include the singular. All publications, patents and other references mentioned herein are incorporated by reference.

Although methods and materials similar or equivalent to those described herein can be used in practice or testing of the present invention, suitable methods and materials are described below. The materials, methods and examples are illustrative only, and are not intended to be limiting. Other features and advantages of the invention will be apparent from the detailed description and from the claims.

Throughout this specification and claims, the word "comprise," or variations such as "comprises" or "comprising," will be understood to imply the inclusion of a stated integer or group of integers but not the exclusion of any other integer or group of integers.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

As used herein, the following definitions shall apply unless otherwise indicated.

The term "homologous recombination" refers to rearrangement of DNA segments at a sequence-specific site (or sites) within or between DNA molecules through base-pairing mechanisms.

The term "homologous region" refers to a sequence within the target gene locus chosen for duplication in the targeting molecule, having sufficient length and homology to provide for site-specific integration of the targeting molecule into the target gene locus, i.e., T1R3, by homologous recombination.

The term "targeting molecule" or "targeting vector" refers to a DNA molecule that is capable of specifically disrupting a target gene, i.e., T1R3, in a transfected cell by homologous recombination so as to prevent expression of a functional protein, i.e., the T1R3 receptor. The DNA molecule may be linear or circular.

The term "disrupting sequence" or "disrupting nucleotide sequence" refers to a nucleotide sequence in a targeting molecule that disrupts a target gene upon site-specific integration of the targeting molecule so as to prevent expression of the target gene, i.e., T1R3.

The term "heterologous" sequence refers to a nucleotide sequence that differs from the sequence comprising the target nucleotide sequence. Heterologous DNA differs from target DNA by the substitution, insertion and/or deletion of one or more nucleotides. Thus, an endogenous gene sequence may be incorporated into a targeting molecule to target its insertion into a different regulatory region of the genome of the same organism. The modified DNA sequence obtained in this way is a heterologous DNA sequence. Heterologous DNA sequences also include endogenous sequences that have been modified to correct or introduce gene defects or to change the amino acid sequence encoded by the endogenous gene. Further, heterologous DNA sequences include exogenous DNA sequences that are not related to endogenous sequences, e.g., sequences derived from a different species. Such "exogenous" DNA sequences include those that encode exogenous polypeptides or exogenous regulatory sequences. DNA sequences encoding positive selection markers are further examples of heterologous DNA sequences.

The term "ES cells" refers to embryonic stem cells.

The term "gene targeting" refers to a type of homologous recombination that occurs when a fragment of genomic DNA is introduced into a mammalian cell and that fragment locates and recombines with endogenous homologous sequences as exemplified in U.S. Pat. No. 5,464,764, issued November 1995, and U.S. Pat. No. 5,777,195, issued Jul. 7, 1998, the contents of which are hereby incorporated by reference herein in their entireties.

The term "transgenic animal" refers to an animal containing one or more cells bearing genetic information received, directly or indirectly, by deliberate genetic manipulation at a subcellular level, such as by microinjection or infection with recombinant virus. The genetic information is typically provided in the form of a "transgene" carried by the transgenic animal. This transgene can be integrated within a chromosome, or it can be extra-chromosomally replicating DNA. In a preferred embodiment, the transgene is integrated within a chromosome. A transgenic animal can include a heterozygous animal (e.g., with one altered allele and one wild-type allele), a homozygous animal (e.g., with two altered alleles) or an animal having more than one gene having at least one allele that has been altered. In some embodiments, the transgenic animal is a mouse.

The transgenic animal may carry the transgene in less than all of its cells. Such a transgenic animal is referred to herein as a "chimeric animal" or a "mosaic animal". In a preferred embodiment, the transgenic animal carries the transgene in all of its cells.

In a preferred embodiment, the term "transgenic animal" as used herein refers to a transgenic animal in which the transgene was introduced into a germ line cell, thereby conferring the ability to transfer the information to offspring. If offspring in fact possess some or all of the transgene, then they, too, are transgenic animals.

In some embodiments, the transgene comprises an altered or deficient gene. In this case, the transgene does not encode the gene product that is native to the host animal, and its expression product can be altered to a small or greater degree, or it can be absent altogether.

The term "knock-out animal"-refers to a transgenic animal in which the transgene comprises an inactive or nonfunctional gene. A knock-out animal lacks all or essentially all of an activity of one or more specific gene/allele, RNA or protein product(s) relative to the corresponding wild-type animal, i.e., the gene is non-functional as compared to the wild-type gene. In a particular embodiment of this type, the knock-out animal contains within its genome a specific gene/allele that has been inactivated by a method such as gene targeting. In another embodiment, RNA interference may be used to silence the expression of a given gene (see, e.g., Paddison et al., *PNAS*, 99: 1443-1448 (2002)). The knock-out animal may produce an interfering RNA (an RNAi) that prevents a given RNA from being translated into a protein. An RNAi can be delivered into a target cell via a variety of methods, including but not limited to liposome fusion (transposomes), routine nucleic acid transfection methods such as electroporation, calcium phosphate precipitation, and microinjection, and infection by viral vectors. As used herein, the term "knock-out animal" can include a heterozygous animal (e.g., with one nonfunctional allele and one wild-type allele), a homozygous animal (e.g., with two nonfunctional alleles) or an animal having more than one gene having at least one allele that has been inactivated. In some embodiments, the knock-out animal is a mouse.

The term "single null gene" refers to a gene that has one defective allele (i.e., a heterozygous gene).

The term "double null gene" refers to a gene that has both alleles defective (i.e., a homozygous gene).

As used herein, italicizing the name of T1R3 shall indicate the T1R3 gene, T1R3 DNA, cDNA, or RNA, in contrast to its encoded protein product which is indicated by the name of T1R3 in the absence of italicizing. For example, "T1R3" shall mean the T1R3 gene, TlR3 DNA, cDNA, or RNA whereas "T1R3" shall indicate the protein product of the T1R3 gene.

The term "modulator" includes inhibitors and activators. These are inhibitory, activating or modulating molecules identified using assays for signal transduction, e.g., ligands, agonists, antagonists and their homologs and mimetics. Inhibitors include compounds that block, decrease, prevent, delay activation of, inactivate, desensitize or down-regulate signal transduction, e.g., antagonists. Inhibitors include compounds that, e.g., bind to components of signal transduction to partially or totally block stimulation of signal transduction. Activators include compounds that stimulate, increase, initiate, activate, facilitate, enhance activation of, sensitize or up-regulate signal transduction. Activators include compounds that, e.g., bind to components of signal transduction to stimulate signal transduction. Modulators also include compounds that, e.g., alter the interaction of a receptor with extracellular proteins that bind activators or inhibitors, G-proteins, kinases, and arrestin-like proteins, which also deactivate and desensitize receptors. Modulators include naturally occurring and synthetic ligands, antagonists, agonists, small molecules and the like.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, T or U) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled with, e.g., isotopes, chromophores, lumiphores or chromogens, or indirectly labeled with, e.g., biotin, to which a streptavidin complex may later bind. By assaying for the presence or absence of the probe, one can detect the presence or absence of the select sequence or subsequence.

Oligonucleotides that are not commercially available can be chemically synthesized using methods known to those of skill in the art. These methods include the solid phase phosphoramidite triester method first described by Beaucage & Caruthers, *Tetrahedron Letts.*, 22: 1859-62 (1981), using an automated synthesizer, as described in Van Devanter et al., *Nucleic Acids Res.*, 12: 6159-68 (1984). Purification of oligonucleotides is by either native acrylamide gel electrophoresis or by anion-exchange HPLC as described in Pearson & Reanier, *J. Chrom.*, 255: 137-49 (1983).

The term "recombinant" when used with reference to, e.g., a cell, nucleic acid, protein or vector, indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all.

The word "tastant" is generally understood to include substances having a taste quality. It will be obvious to those skilled in the art that the word "tastant" is also applicable to substances, with or without taste, that bind to, interact with or otherwise affect taste bud membranes and/or taste cell components such as receptors, ion channels and other signal transduction elements. Examples of tastants include a molecule from a food, a beverage, a medicament, a component of the medicament, a breakdown product of the component of the medicament, a preservative or a nutritional supplement. In some embodiments, the component of the medicament is a vehicle for the medicament. Other examples of tastants include a molecule from a medical or dental composition, such as a contrast material or a local oral anesthetic, or from a cosmetic, such as a face cream or lipstick. The tastant can also be a metallic salt, an oral film, or a molecule from any composition that may contact taste membranes. Examples include, but are not limited to, soap, shampoo, toothpaste, mouthwash, mouthrinse, denture adhesive, glue on the surface of stamps, glue on the surface of envelopes, or a composition used in pest control, such as rat or cockroach poison.

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994).

Gene expression of a taste signaling protein can be analyzed by techniques known in the art, e.g., reverse transcription and amplification of mRNA, isolation of total RNA or poly A+ RNA, northern blotting, dot blotting, in situ hybridization, RNase protection, probing DNA microchip arrays, and the like (see, e.g., Gunthand et al., *AIDS Res. Hum. Retroviruses*, 14: 869-76 (1998); Kozal et al., *Nat. Med.*, 2: 753-59 (1996); Matson et al., *Anal. Biochem.*, 224: 110-16 (1995); Lockhart et al., *Nat. Biotechnol.*, 14: 1675-80 (1996); Gingeras et al., *Genome Res.*, 8: 435-48 (1998); Hacia et al., *Nucleic Acids Res.*, 26: 3865-66 (1998)).

Potential tastants and modulators can be selected on the basis of whether there is a statistical significance between the test response and the normal response. Potential tastants and modulators are selected that show a statistically significant change in the characteristic measured or determined. In a particular embodiment, the normal response of the knock-out animal in the presence of a sweet or umami tastant or other modulator of T1R3-mediated signal transduction is characteristically different by being characteristically lower or higher than that of wild-type animals.

BRIEF DESCRIPTION OF THE DRAWINGS

FIG. 1B. The nucleotide (SEQ ID NO: 1) and predicted amino acid (SEQ ID NO: 2) sequences of human T1R3. The ends of the introns are indicated in highlighted lower case letters.

FIG. 5A. mT1R3 allelic differences. mT1R3 allelic differences between eight inbred mouse strains. All non-taster strains showed identical sequences and were grouped in one row. In the bottom row the amino acid immediately before the position number is always from the non-tasters, while the amino acid immediately before the position number is from whichever tasters differed at that position from the non-tasters. The two columns in bold represent positions where all tasters differed from non-tasters and where the differences in nucleotide sequence result in amino acid substitutions. Nucleotide differences that do not alter the encoded amino acid are indicated as s: silent. Nucleotide differences within introns are indicated as i: intron.

FIG. 6. The amino acid sequence of mouse T1R3 (SEQ ID NO: 3) is aligned with that of two other rat taste receptors (rT1R1 (SEQ ID NO: 4) and rT1R2 (SEQ ID NO: 5)), the murine extracellular calcium sensing (mECaSR (SEQ ID NO: 6)) and the metabotropic glutamate type 1 (mGluR1 (SEQ ID NO: 7)) receptors. Regions of identity among all five receptors are indicated by white letters on black; regions where one or more of these receptors share identity with T1R3 are indicated by black letters on gray. Boxes with dashed lines indicate regions predicted to be involved in dimerization (based upon the solved structure for the amino terminal domain of mGluR1 (SEQ ID NO: 7)); filled circles indicate predicted ligand binding residues based on mGluR1 (SEQ ID NO: 7); blue lines linking cysteine residues indicate predicted intermolecular disulfide bridges based on mGluR1. Amino acid sequences noted above the alignment indicate polymorphisms that are found in all strains of nontaster mice. The predicted N-linked glycosylation site conserved in all five receptors is indicated by a black squiggle; the predicted N-linked glycosylation site specific to T1R3 in nontaster strains of mice is indicated by the red squiggle.

FIGS. 8A and 8B. A murine T1R3 nucleotide sequence (SEQ ID NO: 8).

FIG. 9. A complete T1R3 CDS (SEQ ID NO: 9) from a taster strain of mice, C57BL/6J. This nucleotide sequence has been deposited as GenBank No. AF368024.

DETAILED DESCRIPTION OF THE INVENTION

Figure 1A:
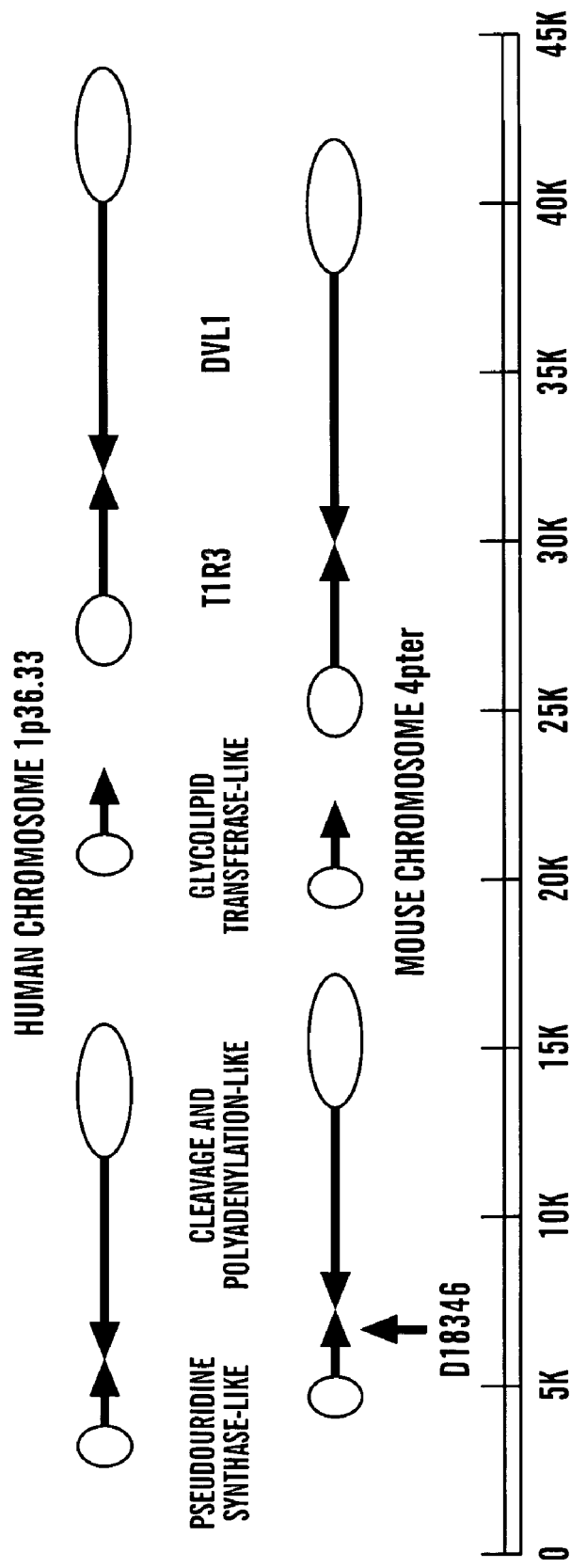
FIG. 1A. Synteny between human lp36.33 and mouse 4pter chromosomal regions near the mouse Sac locus. Shaded circles indicate the approximate location of the predicted start codons for each gene; arrows indicate the full span of each gene including both introns and exons; arrowheads indicate the approximate location of each polyadenylation signal. Genes indicated by lowercase letters were predicted by Genscan and named according to their closest homolog. Genes indicated by capital letters (T1R3 and DVL1) were experimentally identified and verified. The mouse marker D18346 indicated is closely linked to the Sac locus and lies within the predicted pseudouridine synthaselike gene. The region displayed corresponds to ~45,000 bp; the bottom scale marker indicates kilobases (K).

T1R3 is a novel receptor that participates in receptor-mediated taste signal transduction and belongs to the family 3 G protein coupled receptors. The present invention encompasses T1R3 nucleotides, T1R3 proteins and peptides, as well as antibodies to the T1R3 protein. The invention also relates to host cells and animals genetically engineered to express the T1R3 receptor or to inhibit or "knock-out" expression of the animal's endogenous T1R3.

Also within the scope of the invention are transgenic cells that express a non-native T1R3 protein or transgenic cells that do not express functional T1R3 protein, e.g. knock-out cells. The invention also provides methods of making transgenic animals and cells comprising disrupted, nonfunctional or non-native T1R3 genes. Also within the scope of the present invention are methods of using the animals of the invention and tissues, taste buds and cells derived from the animals to identify and study tastants, including sweet and umami tastants, and other modulators of T1R3-mediated signal transduction, such as enhancers of desirable flavors and blockers of undesirable flavors.

The invention further provides screening assays designed for the identification of modulators, such as agonists and antagonists, of T1R3 activity. The use of host cells that naturally express T1R3 or genetically engineered host cells and/or animals offers an advantage in that such systems allow the identification of compounds that affect the signal transduced by the T1R3 receptor protein.

Various aspects of the invention are described in greater detail in the subsections below.

The T1R3 Gene

Figure 1B:
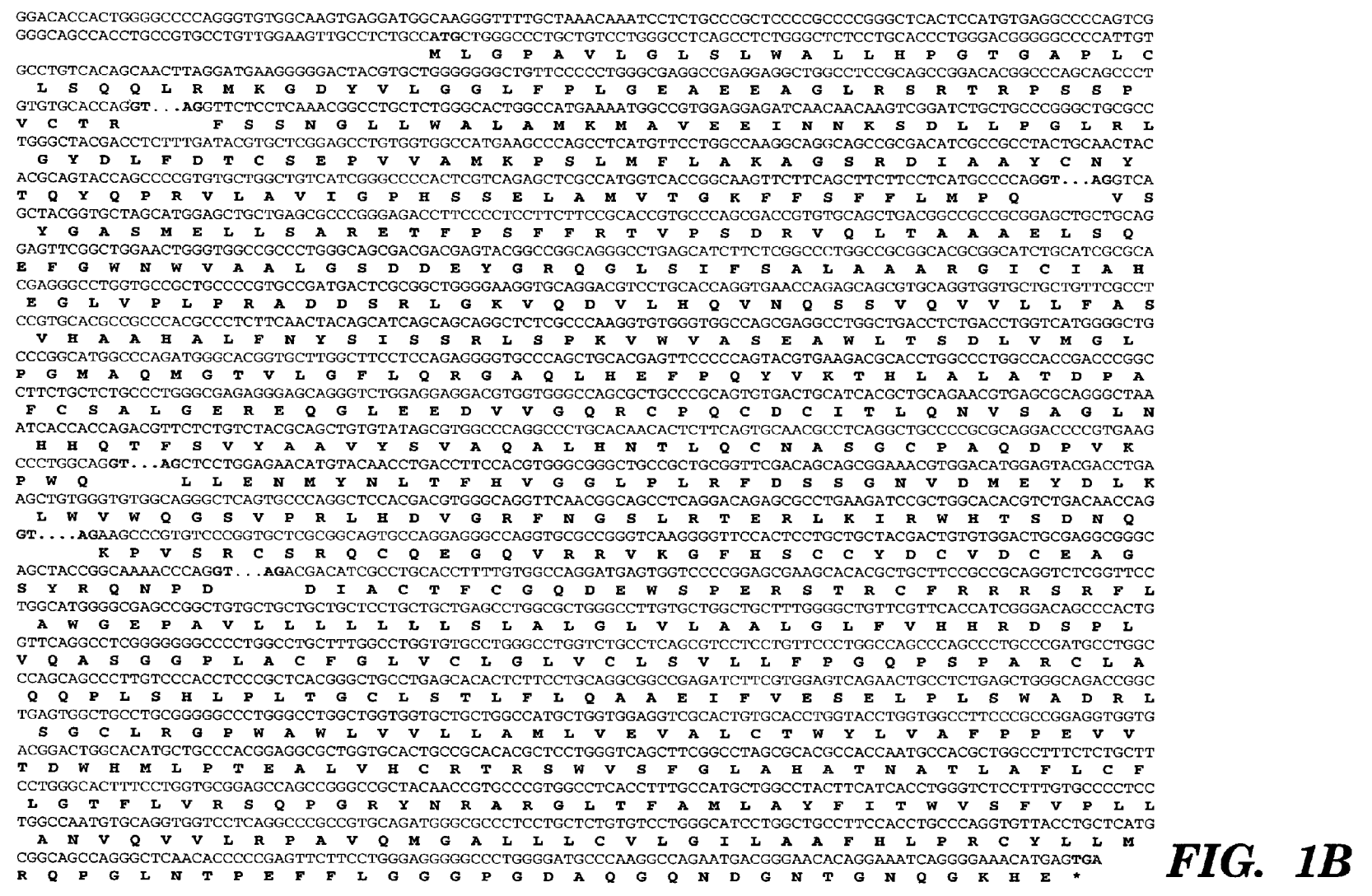

The cDNA sequence (SEQ ID NO: 1) and deduced amino acid sequence (SEQ ID NO: 2) of human T1R3 is shown in FIG. 1B. The T1R3 nucleotide sequences of the invention include: (a) the DNA sequence shown in FIG. 1B; (b) nucleotide sequences that encode the amino acid sequence shown in FIG. 1B; (c) any nucleotide sequence that (i) hybridizes to the nucleotide sequence set forth in (a) or (b) under stringent conditions, e.g., hybridization to filter-bound DNA in 0.5 M NaHPO₄, 7% sodium dodecyl sulfate (SDS), 1 mM EDTA at 65EC, and washing in 0.1×SSC/0.1% SDS at 68EC (Ausubel F. M. et al., eds., 1989, Current Protocols in Molecular Biology, Vol. I, Green Publishing Associates, Inc., and John Wiley & sons, Inc., New York, at p. 2.10.3) and (ii) encodes a functionally equivalent gene product; and (d) any nucleotide sequence that hybridizes to a DNA sequence that encodes the amino acid sequence shown in FIG. 1B, under less stringent conditions, such as moderately stringent conditions, e.g., washing in 0.2×SSC/0.1% SDS at 42EC (Ausubel et al., 1989 supra), yet which still encodes a functionally equivalent T1R3 gene product. Functional equivalents of the T1R3 protein include naturally occurring T1R3 present in species other than humans. The invention also includes degenerate variants of sequences (a) through (d). The invention also includes nucleic acid molecules, that may encode or act as T1R3 antisense molecules, useful, for example, in T1R3 gene regulation (for and/or as antisense primers in amplification reactions of T1R3 gene nucleic acid sequences).

In addition to the T1R3 nucleotide sequences described above, homologs of the T1R3 gene present in other species can be identified and readily isolated, without undue experimentation, by molecular biological techniques well known in the art. For example, cDNA libraries, or genomic DNA libraries derived from the organism of interest can be screened by hybridization using the nucleotides described herein as hybridization or amplification probes.

The invention also encompasses nucleotide sequences that encode mutant T1R3s, peptide fragments of the T1R3, truncated T1R3, and T1R3 fusion proteins. These include, but are not limited to nucleotide sequences encoding polypeptides or peptides corresponding to functional domains of T1R3, including but not limited to, the ATD (amino terminal domain) that is believed to be involved in ligand binding and dimerization, the cysteine rich domain, and/or the transmembrane spanning domains of T1R3, or portions of these domains; truncated T1R3s in which one or two domains of T1R3 is deleted, e.g., a functional T1R3 lacking all or a portion of the ATD region. Nucleotides encoding fusion proteins may include but are not limited to full length T1R3, truncated T1R3 or peptide fragments of T1R3 fused to an unrelated protein or peptide such as an enzyme, fluorescent protein, luminescent protein, etc., which can be used as a marker.

Based on the model of T1R3's structure, it is predicted that T1R3 dimerizes to form a functional receptor. Thus, certain of these truncated or mutant T1R3 proteins may act as dominant-negative inhibitors of the native T1R3 protein. T1R3 nucleotide sequences may be isolated using a variety of different methods known to those skilled in the art. For example, a cDNA library constructed using RNA from a tissue known to express T1R3 can be screened using a labeled T1R3 probe. Alternatively, a genomic library may be screened to derive nucleic acid molecules encoding the T1R3 receptor protein. Further, T1R3 nucleic acid sequences may be derived by performing PCR using two oligonucleotide primers designed on the basis of the T1R3 nucleotide sequences disclosed herein. The template for the reaction may be cDNA obtained by reverse transcription of mRNA prepared from cell lines or tissue known to express T1R3.

The invention also encompasses (a) DNA vectors that contain any of the foregoing T1R3 sequences and/or their complements (i.e., antisense); (b) DNA expression vectors that contain any of the foregoing T1R3 sequences operatively associated with a regulatory element that directs the expression of the T1R3 coding sequences; (c) genetically engineered host cells that contain any of the foregoing T1R3 sequences operatively associated with a regulatory element that directs the expression of the T1R3 coding sequences in the host cell; and (d) transgenic mice or other organisms that contain any of the foregoing T1R3 sequences. As used herein, regulatory elements include but are not limited to inducible and non-inducible promoters, enhancers, operators and other elements known to those skilled in the art that drive and regulate expression.

T1R3 Proteins and Polypeptides

T1R3 protein, polypeptides and peptide fragments, mutated, truncated or deleted forms of the T1R3 and/or T1R3 fusion proteins can be prepared for a variety of uses, including but not limited to the generation of antibodies, the identification of other cellular gene products involved in the regulation of T1R3 mediated taste transduction, and the screening for compounds that can be used to modulate taste perception such as novel sweetners and taste modifiers.

FIG. 1B shows the deduced amino acid sequence (SEQ ID NO: 2) of the human T1R3 protein. The T1R3 amino acid sequences of the invention include the amino acid sequence shown in FIG. 1B. Further, T1R3s of other species are encompassed by the invention. In fact, any T1R3 protein encoded by the T1R3 nucleotide sequences described in Section 5.1, above, is within the scope of the invention.

The invention also encompasses proteins that are functionally equivalent to the T1R3 encoded by the nucleotide sequences described in Section 5.1, as judged by any of a number of criteria, including but not limited to the ability of a sweet tastant to activate T1R3 in a taste receptor cell, leading to transmitter release from the taste receptor cell into the synapse and activation of an afferent nerve. Such functionally equivalent T1R3 proteins include but are not limited to proteins having additions or substitutions of amino acid residues within the amino acid sequence encoded by the T1R3 nucleotide sequences described, above, in Section 5.1, but which result in a silent change, thus producing a functionally equivalent gene product.

Peptides corresponding to one or more domains of T1R3 (e.g., amino terminal domain, the cysteine rich domain and/or the transmembrane spanning domains), truncated or deleted T1R3s (e.g., T1R3 in which the amino terminal domain, the cysteine rich domain and/or the transmembrane spanning domains is deleted) as well as fusion proteins in which the full length T1R3, a T1R3 peptide or a truncated T1R3 is fused to an unrelated protein are also within the scope of the invention and can be designed on the basis of the T1R3 nucleotide and T1R3 amino acid sequences disclosed herein. Such fusion proteins include fusions to an enzyme, fluorescent protein, or luminescent protein which provide a marker function.

While the T1R3 polypeptides and peptides can be chemically synthesized (e.g., see Creighton, 1983, Proteins: Structures and Molecular Principles, W. H. Freeman & Co., N.Y.), large polypeptides derived from T1R3 and the full length T1R3 itself may be advantageously produced by recombinant DNA technology using techniques well known in the art for expressing a nucleic acid containing T1R3 gene sequences and/or coding sequences. Such methods can be used to construct expression vectors containing the T1R3 nucleotide sequences described in Section 5.1 and appropriate transcriptional and translational control signals. These methods include, for example, in vitro recombinant DNA techniques, synthetic techniques, and in vivo genetic recombination. (See, for example, the techniques described in Sambrook et al., 1989, supra, and Ausubel et al., 1989, supra).

A variety of host-expression vector systems may be utilized to express the T1R3 nucleotide sequences of the invention. Where the T1R3 peptide or polypeptide is expressed as a soluble derivative (e.g., peptides corresponding to the amino terminal domain the cysteine rich domain and/or the transmembrane spanning domain) and is not secreted, the peptide or polypeptide can be recovered from the host cell. Alternatively, where the T1R3 peptide or polypeptide is secreted the peptide or polypeptides may be recovered from the culture media. However, the expression systems also include engineered host cells that express T1R3 or functional equivalents, anchored in the cell membrane. Purification or enrichment of the T1R3 from such expression systems can be accomplished using appropriate detergents and lipid micelles and methods well known to those skilled in the art. Such engineered host cells themselves may be used in situations where it is important not only to retain the structural and functional characteristics of the T1R3, but to assess biological activity, i.e., in drug screening assays.

The expression systems that may be used for purposes of the invention include but are not limited to microorganisms such as bacteria transformed with recombinant bacteriophage, plasmid or cosmid DNA expression vectors containing T1R3 nucleotide sequences; yeast transformed with recombinant yeast expression vectors containing T1R3 nucleotide sequences or mammalian cell systems harboring recombinant expression constructs containing promoters derived from the genome of mammalian cells or from mammalian viruses.

Appropriate expression systems can be chosen to ensure that the correct modification, processing and subcellular localization of the T1R3 protein occurs. To this end, eukaryotic host cells which possess the ability to properly modify and process the T1R3 protein are preferred. For long-term, high yield production of recombinant T1R3 protein, such as that desired for development of cell lines for screening purposes, stable expression is preferred. Rather than using expression vectors which contain origins of replication, host cells can be transformed with DNA controlled by appropriate expression control elements and a selectable marker gene, i.e., tk, hqprt, dhfr, neo, and hyqro gene, to name a few. Following the introduction of the foreign DNA, engineered cells may be allowed to grow for 1-2 days in enriched media, and then switched to a selective media. Such engineered cell lines may be particularly useful in screening and evaluation of compounds that modulate the endogenous activity of the T1R3 gene product.

Transgenic Animals

The T1R3 gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate T1R3 transgenic animals.

The transgenic animals of the present invention include non-human animals that are heterozygous or homozygous for a T1R3 transgene. The T1R3 transgene may comprise any of the T1R3 nucleic acid sequences described herein. The transgenic animals may comprise a non-native T1R3 transgene either in the presence or absence of the native (wild-type) T1R3 gene.

In some embodiments, the T1R3 transgene comprises an altered T1R3 gene. An altered or deficient T1R3 gene does not encode the T1R3 that is native to the host animal, and its expression product can be altered to a small or greater degree, or it can be absent altogether.

The T1R3 mutation may be a targeted deletion mutation, a targeted substitution mutation and/or a targeted insertion mutation. However, the preferred mutation is a deletion mutation, and especially preferred is a deletion mutation which results in a deletion of most, if not all, of the T1R3 gene. Transgenic animals are generated which have an altered or, preferably, completely deleted T1R3 gene. T1R3 gene deletions, gene modifications and or gene insertions can render the native gene nonfunctional, producing a knock-out animal, or can lead to a T1R3 with altered expression or activity. T1R3 knock-out mice are preferred and exemplified herein in Examples 2-4.

A preferred deletion mutation may contain a deletion of anywhere from 1 nucleotide to deletion of the entire gene, including the open reading frame and associated cis-acting regulatory sequences associated with wild-type T1R3. A smaller deletion within the open reading frame is preferably not divisible by three, so as to result in a frameshift mutation resulting in a protein which most likely is non-functional. It is preferred that any such smaller deletion not divisible by three be targeted toward the 5' region of the open reading frame to increase the possibility of generating a non-functional truncated protein product. However, as noted above, it is preferable that the deletion mutation encompass most, if not all, of the T1R3 gene so as to prevent of expression of a functional T1R3 protein.

In cases where it is useful to express a non-native T1R3 gene in a transgenic animal in the absence of a native T1R3 gene, the altered T1R3 gene induces a null or knock-out phenotype in the animal. The native T1R3 gene is rendered substantially, preferably completely, nonfunctional, while the non-native T1R3 gene can be expressed. The non-native T1R3 gene could be introduced according to standard techniques known in the art. In one such embodiment, the transgenic animal is a knock-out mouse, and the non-native gene comprises the human, ape or old world monkey T1R3 gene. Such a transgenic mouse would be useful for studies of tastants or taste modulators that are only perceived by old world primates such as humans, apes and old world monkeys. For example, only old world primates perceive sweeteners such as brazzein, aspartame and monellin as sweet.

Any technique known in the art may be used to introduce the T1R3 transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, *Proc. Natl. Acad. Sci. USA* 82: 6148-6152); gene targeting in embryonic stem cells (Thompson et al., 1989, *Cell*, 56: 313-321); electroporation of embryos (Lo, 1983, Mol Cell. Biol. 3: 1803-1814); and sperm-mediated gene transfer (Lavitrano et al., 1989, *Cell* 57: 717-723); etc. For a review of such techniques, see Gordon, 1989, *Transgenic Animals, Intl. Rev. Cytol.* 115: 171-229, which is incorporated by reference herein in its entirety.

The present invention provides for transgenic animals that carry the T1R3 transgene in all their cells, as well as animals which carry the transgene in some, but not all their cells, i.e., mosaic animals. The transgene may also be selectively introduced into and activated in a particular cell type by following, for example, the teaching of Lasko et al., (Lasko, M. et al., 1992, *Proc. Natl. Acad. Sci. USA* 89: 6232-6236). The regulatory sequences required for such a cell-type specific activation will depend upon the particular cell type of interest, and will be apparent to those of skill in the art. When it is desired that the T1R3 transgene be integrated into the chromosomal site of the endogenous T1R3 gene, gene targeting is preferred. Briefly, when such a technique is to be utilized, vectors containing some nucleotide sequences homologous to the endogenous T1R3 gene are designed for the purpose of integrating, via homologous recombination with chromosomal sequences, into and disrupting the function of the nucleotide sequence of the endogenous T1R3 gene.

The first step in the use of gene targeting to produce the transgenic animals of this invention is to prepare a DNA sequence ("targeting molecule" or "targeting vector") that is capable of specifically disrupting a T1R3 gene in animal cells carrying that gene and rendering that gene nonfunctional. The targeting molecule is then used to transfect animal cells and to disrupt the functional T1R3 genes in those cells. The transgenic animal cells may then be used to produce the transgenic animals of this invention. Construction of a T1R3 targeting molecule capable of disrupting a murine T1R3 target gene is described in Example 2.

Production of a DNA targeting molecule requires a DNA clone comprising at least a portion of the T1R3 target gene or DNA clones comprising sequences between which at least a portion of the T1R3 target gene lies. Such DNA clones necessary for practice of the present invention may be obtained by a variety of means. For example, suitable DNA clones may be obtained by following the T1R3 gene cloning methods set forth herein, by use of the sequences provided herein or other published sequences for chemical synthesis of T1R3 genes or portions thereof, or by use of the available sequences for chemical synthesis of oligonucleotide probes which may be used in well-known procedures to isolate T1R3 gene sequences from a cDNA library or a genomic library.

A DNA targeting molecule that is capable, in accordance with this invention, of disrupting a functional T1R3 gene native in cells may be produced using information and processes well known in the art. Such a DNA targeting molecule must be capable of integrating at a native T1R3 gene locus ("target gene locus") and disrupting the T1R3 gene expression associated with that locus so that no expression of native T1R3 protein is possible. These essential functions depend on two basic structural features of the targeting molecule.

The first structural feature of the targeting molecule is a pair of regions that are homologous to chosen regions of the target gene locus. That homology (in terms of both sequence identity and length) causes the targeting molecule to integrate by base pairing mechanisms ("homologous recombination") at the site chosen in the target gene locus in transfected cells. The regions of homology between the target gene and the targeting molecule result in site-specific integration of the heterologous sequence.

The second structural feature of the targeting molecule is a disrupting sequence between the homologous regions. The disrupting sequence prevents expression of functional T1R3 protein from the T1R3 target gene following the replacement of a portion of that target gene by the integrated targeting molecule.

Properties of the targeting molecule that may be varied in the practice of the present invention include the lengths of the homologous regions, what regions of the target gene locus are to be duplicated as the homologous regions of the targeting molecule, the length of the disrupting sequence, the identity of the disrupting sequence, and what sequence of the target gene is to be replaced by the targeting molecule.

It should be noted that the target gene locus nucleotide sequences chosen for homology in the targeting molecule remain unchanged after integration of the targeting molecule. Those sequences of the target gene locus are merely replaced by the duplicate (homologous) sequences in the targeting molecule. Identity between the chosen regions of the target gene locus and the homologous regions in the targeting molecule is the means by which the targeting molecule delivers the disrupting sequence precisely into the T1R3 target gene.

It is necessary that the nucleotide sequence of the disrupting region not express a functional native T1R3 protein and not express a protein or polypeptide toxic to the transformed cell. It is also preferred that the disrupting sequence not be extensively homologous to sites in the genome of the transfected cell. Such homology would be likely to diminish the efficiency of the targeting molecule, and might severely impair its function.

For some embodiments of the present invention it is preferred that the disrupting sequence have a dual function, i.e., be both a selectable marker and a disrupting sequence. In those embodiments, the length and identity of the disrupting sequence will be determined largely by the selectable marker coding sequence and associated expression control sequences. The selectable marker gene provides for positive selection of transfected cells that have taken up and integrated the targeting molecule. The need for a selectable marker will depend on the methods chosen for transfection of cells and transgenic animal production. The choice of those methods, in turn, will depend on the species of animal on which this invention is being practiced. For example, a preferred method for production of transgenic mice involves murine ES cells, and a preferred method of transfecting ES cells is electroporation, with which a selectable marker is preferred. The preferred selectable marker is the antibiotic resistance gene, neomycin phosphotransferase ("neo"). A neo gene with mammalian expression control sequences is commercially available (Stratagene Cloning Systems, La Jolla, Calif.). Although neo is preferred for mammalian cell selection, other marker genes, such as thymidine kinase, dihydrofolate reductase, hygromycin B phosphotransferase, xanthine-guanine phosphoribosyl transferase, adenosine deaminase, asparagine synthetase and CAD (carbamyl phosphate synthetase/aspartate transcarbamylase/dihydroorotase) may be used with appropriate culture media.

In some embodiments of the present invention, the disrupting sequence comprises a non-native T1R3 gene. In those embodiments, the disrupting sequence simultaneously disrupts the native T1R3 gene and introduces the non-native T1R3 gene. A targeting molecule containing such a disrupting sequence can be used to produce a T1R3 knock-out animal that is capable of expressing a non-native T1R3 protein.

In this discussion, the targeting molecule is described as a linear DNA molecule. However, it should be recognized that a targeting molecule of the present invention could also be embodied as a circular DNA molecule. A circular targeting molecule could comprise a pair of homologous regions separated by a disrupting region, as described for a linear targeting molecule. Alternatively, a circular targeting molecule could comprise a single homologous region. Upon integration at the target gene locus, the circular molecule would become linearized, with a portion of the homologous region at each end. Thus, the single homologous region effectively becomes two homologous regions, as described in the discussion of linear targeting molecules (see Watson et al., *Molecular Biology of the Gene* (4th Ed.), Benjamin/Cummings, Menlo Park, Calif., p. 606). One differing aspect of a circular targeting molecule with a single homologous region is that it inserts the disrupting sequence into the target gene and disrupts it without replacing any of the target gene. A second differing aspect is that the single homologous region must be within the target gene and located 5' to at least one critical site in the T1R3 coding sequence.

Once a DNA targeting molecule capable of disrupting a functional native T1R3 gene has been produced, it may be introduced into a desired animal cell to produce a founder line of the desired transgenic animals. Upon transfection of the desired animal cell with the targeting molecule, the disrupting region of the targeting molecule is integrated into the target T1R3 gene, rendering that gene non-functional.

The cell type chosen for transfection with the T1R3 targeting molecule must be pluripotent. The defining characteristic of pluripotent cells is developmental plasticity, which is necessary for production of a transgenic animal. Pluripotent cells are exemplified by oocytes, sperm and embryonic cells. Oocytes and embryonic cells are preferred in the practice of the present invention. Animal species is a major factor in the choice of pluripotent cell type to be used in practicing the present invention. For example, ES cell culture methods are not fully developed for all species.

Embryonic stem cells maintained in culture are preferred for the production of transgenic small mammals such as mice and hamsters, with short generation intervals and large litter size. Generation interval and litter size are factors to be considered, because the ES cell method yields chimeric animals. Advantages of the ES cell method are that ES cells can be maintained in culture in large numbers, and they can be efficiently transformed by standard electroporation techniques.

The transgene can be introduced into the ES cells by a variety of methods known in the art, including electroporation, microinjection, and lipofection. Cells carrying the transgene can then be injected into blastocysts which are then implanted into pseudopregnant animals. In alternate embodiments, the transgene-targeted embryonic stem cells can be co-incubated with fertilized eggs or morulae followed by implantation into females. After gestation, the animals obtained are chimeric founder transgenic animals. The founder animals can be used in further embodiments to cross with wild-type animals to produce F1 animals heterozygous for the altered T1R3 gene. In further embodiments, these heterozygous animals can be interbred to obtain the viable transgenic embryos whose somatic and germ cells are homozygous for the altered T1R3 gene and thereby lack a functional native T1R3 gene. In other embodiments, the heterozygous animals can be used to produce cell lines.

The method of Krimpenfort et al. (Bio/Technology 9, pp. 844-47 (1991)) is preferred for production of transgenic cattle and other large mammals in accord with the present invention. In that method, immature oocytes are collected by aspiration of follicles on ovaries from slaughtered animals. The oocytes are fertilized in vitro by standard techniques. The DNA targeting molecule is placed in the pronucleus of the single-cell embryo by microinjection at an appropriate time interval after oocyte fertilization (between 16 and 23 hours for cattle). Differential interference contrast microscopy is preferred for microinjection of bovine zygotes, due to their opacity. The embryos are cultured for an appropriate period following microinjection (nine days for cattle), and they are then evaluated for development and normal appearance. An animal that started estrous on the same day that the oocytes were fertilized is used as a recipient of one or two cultured embryos that have developed to the compact morula or early blastula stage.

In an alternative microinjection approach for producing transgenic mammals, including sheep and cattle, early embryos are obtained surgically from oviducts of superovulated, artificially inseminated mammals, subjected to microinjection of the T1R3 targeting molecule, and transferred back to the donor female or another physiologically receptive female for gestation (Ebert et al., *Bio/Technology* 9, pp. 835-38 (1991)). The use of embryos retrieved after in vivo fertilization may yield a somewhat higher number of transgenic animals per embryo, but the method is more labor-intensive than the method of Krimpenfort et al., described above. For a discussion of surgical techniques used to obtain single-cell embryos from sheep, see PCT patent publication WO 90/08832.

Once transgenic animals have been generated, the expression of the recombinant T1R3 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of T1R3 gene-expressing tissue may also be evaluated immunocytochemically using antibodies specific for the T1R3 transgene product.

In some embodiments, the transgenic mammal is a mouse. The T1R3 transgenic mouse may be heterozygous or homozygous for an altered T1R3 gene. In a preferred embodiment, the T1R3 transgenic mouse is a knock-out mouse that is heterozygous or homozygous for a nonfunctional T1R3 gene. Mice homozygous for a nonfunctional T1R3 gene do not produce functional T1R3 protein. In another preferred embodiment, the T1R3 knock-out mouse is capable of expressing a non-native T1R3 gene. In a specific embodiment, the non-native T1R3 gene is native to a human, ape or old world monkey.

Mice that are homozygous for a nonfunctional T1R3 gene such that they do not produce functional T1R3 protein are specifically exemplified in Examples 2-4. In behavioral tests such as the two-bottle preference test, these mice exhibit indifference to sucrose and three artificial sweeteners (sucralose, acesulfame K and SC45647) and a reduced response to glucose. In addition, they show a reduced response to the umami tastant monosodium glutamate (MSG). Nerve recordings from the gustatory nerves also show modified responses to tastants. Recordings from the chorda tympani (CT) branch of the facial and glossopharyngeal nerve show nearly abolished responses to sweet-tasting amino acids, sugar alcohols and sugars (e.g., D-tryptophan) and diminished responses to other sweeteners (e.g., sucrose, fructose, maltose and sorbitol). Nerve responses are not diminished for glucose. At the highest concentration tested, responses to the umami tastant MSG are also diminished. Moreover, the response to MSG in addition to the umami taste potentiator IMP is markedly reduced and indistinguishable from the response to MSG alone.

Thus, mice homozygous for the nonfunctional T1R3 gene exhibit no preference for artificial sweeteners and have diminished, but not abolished behavioral and nerve responses to sugar and umami compounds. This indicates that murine responses to artificial sweeteners are mediated by the T1R3 receptor whereas T1R3-independent receptors and/or pathways mediate at least part of the murine responses to other sweeteners and umami tastants.

Cells

The T1R3 gene products can also be expressed in transgenic cells. These cells may be of any species, including, but not limited to, mice, rats, rabbits, guinea pigs, pigs, micropigs, goats, and non-human primates, e.g., baboons, monkeys and chimpanzees.

The transgenic cells of the present invention include non-human cells that are heterozygous or homozygous for a T1R3 transgene. The T1R3 transgene may comprise any of the T1R3 nucleic acid sequences described herein. The transgenic cells may comprise a non-native T1R3 transgene either in the presence or absence of the native (wild-type) T1R3 gene.

In some embodiments, the T1R3 transgene comprises an altered T1R3 gene. An altered or deficient T1R3 gene does not encode the T1R3 that is native to the cell, and its expression product can be altered to a small or greater degree, or it can be absent altogether.

The T1R3 mutation may be a targeted deletion mutation, a targeted substitution mutation and/or a targeted insertion mutation. However, the preferred mutation is a deletion mutation, and especially preferred is a deletion mutation which results in a deletion of most, if not all, of the T1R3 gene. Transgenic cells are generated which have an altered or, preferably, completely deleted T1R3 gene. T1R3 gene deletions, gene modifications and or gene insertions can render the native gene nonfunctional, producing a knock-out cell, or can lead to a T1R3 with altered expression or activity. T1R3 knock-out murine cells are preferred.

A preferred deletion mutation may contain a deletion of anywhere from 1 nucleotide to deletion of the entire gene, including the open reading frame and associated cis-acting regulatory sequences associated with wild-type T1R3. A smaller deletion within the open reading frame is preferably not divisible by three, so as to result in a frameshift mutation resulting in a protein which most likely is non-functional. It is preferred that any such smaller deletion not divisible by three be targeted toward the 5' region of the open reading frame to increase the possibility of generating a non-functional truncated protein product. However, as noted above, it is preferable that the deletion mutation encompass most, if not all, of the T1R3 gene so as to prevent of expression of a functional T1R3 protein.

In cases where it is useful to express a non-native T1R3 gene in a transgenic cell in the absence of a native T1R3 gene, the altered T1R3 gene induces a null or knock-out phenotype in the cell. The native T1R3 gene is rendered substantially, preferably completely, nonfunctional, while the non-native T1R3 gene can be expressed. The non-native T1R3 gene could be introduced according to standard techniques known in the art. In one such embodiment, the transgenic cell is a knock-out murine cell, and the non-native gene comprises the human, ape or old world monkey T1R3 gene. Such a transgenic murine cell would be useful for studies of tastants or taste modulators that are only perceived by old world primates such as humans, apes and old world monkeys. For example, only old world primates perceive sweeteners such as brazzein, aspartame, thaumatin and monellin as sweet.

Cells particularly suitable for the present invention are cells that comprise or are capable of expressing elements of the taste signal transduction pathway. In some embodiments of the invention, the cells comprise or are capable of expressing at least one of the following taste signaling proteins: T1R1, T1R2, T1R4, Trpm5, T2R, Trpm5, PDE1A, PLCβ2, Gγ13, Gβ3, inositol trisphosphate receptor type 3, adenylyl cyclase isoform 8, α-gustducin and α-transducin. In a preferred embodiment, the cells are taste cells. In another preferred embodiment, the cells are gastrointestinal cells, preferably endocrine L cells, more preferably NCI-H716 cells, which have been deposited as ATCC No. CCL-251. NCI-H716 cells are capable of expressing a number of endogenous taste signaling elements, including, e.g., α-gustducin, T1R1, T1R2, T1R3, Trpm-5, PDE1A, PLCβ2, TAS2R3, TAS2R4, TAS2R10, TAS2R13, TAS2R38, TAS2R43, TAS2R44, TAS2R45, TAS2R46 and TAS2R48.

Methods of introducing genes into cells are well known in the art. Any of these techniques may be used to introduce a T1R3 transgene into a cell in order to produce the transgenic cells of the present invention. In some embodiments, the cells are isolated or derived from the non-human transgenic mammals provided herein. In a preferred embodiment, the animals are mice.

Preferably, the cells are grown in tissue culture. Alternative forms of cell culture, such as organ culture of tissue from chimeric or transgenic animals, may also be used. Methods for culturing taste cells, such as isolated taste buds, are known in the art. See, e.g., Ruiz, C. J. et al., *Chem. Senses*, 26: 861-73 (2001); Kishi, M. et al., *Neuroscience*, 106: 217-225 (2001); Kishi, M. et al., *Biosci. Biotechnol. Biochem.*, 66: 484-487 (2002). Methods for transferring foreign genes into isolated taste cells have also been described. See, e.g., Kishi, M. et al.,

*Neuroscience,* 106: 217-225 (2001); Stone, L. M. et al., *Chem. Senses,* 27: 779-787 (2002).

In some embodiments, the transgenic cell is heterozygous or homozygous for an altered T1R3 gene. In a preferred embodiment, the T1R3 transgenic cell is a knock-out cell that is heterozygous or homozygous for a nonfunctional T1R3 gene. Cells homozygous for a nonfunctional T1R3 gene do not produce functional T1R3 protein. In another preferred embodiment, the T1R3 knock-out cell is capable of expressing a non-native T1R3 gene. In a specific embodiment, the non-native T1R3 gene is native to a human, ape or old world monkey. In a more specific embodiment, the cell is murine.

Experimental model systems based on the cells of the present invention can be used to further define T1R3-mediated taste signal transduction. For example, such experimental model systems may be used to study T1R3-mediated signal transduction, such as the role of signal transduction elements and their responses to different types of tastants and taste modulators. Such model systems would also be useful for screening for novel tastants and other modulators of T1R3-mediated signal transduction, including enhancers of desirable flavors and blockers of undesirable flavors.

Antibodies to T1R3 Proteins

Antibodies that specifically recognize one or more epitopes of T1R3, or epitopes of conserved variants of T1R3, or peptide fragments of T1R3 are also encompassed by the invention. Such antibodies include but are not limited to polyclonal antibodies, monoclonal antibodies (mAbs), humanized or chimeric antibodies, single chain antibodies, Fab fragments, F (ab')$_2$ fragments, fragments produced by a Fab expression library, anti-idiotypic (anti-Id) antibodies, and epitope-binding fragments of any of the above.

The antibodies of the invention may be used, for example, in conjunction with compound screening schemes, as described, below, for the evaluation of the effect of test compounds on expression and/or activity of the T1R3 gene product.

For production of antibodies, various host animals may be immunized by injection with a T1R3 protein, or T1R3 peptide. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacille Calmette-Guerin) and *Corynebacterium parvum.*

Polyclonal antibodies comprising heterogeneous populations of antibody molecules, may be derived from the sera of the immunized animals. Monoclonal antibodies may be obtained by any technique which provides for the production of antibody molecules by continuous cell lines in culture. These include, but are not limited to, the hybridoma technique of Kohler and Milstein, (1975, *Nature* 256: 495-497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80: 2026-2030), and the EBV-hybridoma technique (Cole et al., 1985, *Monoclonal Antibodies And Cancer Therapy,* Alan R. Liss, Inc., pp. 77-96). Such antibodies may be of any immunoglobulin class including IgG, IgM, IgE, IgA, IgD and any subclasses thereof. The hybridoma producing the mAb of this invention may be cultivated in vitro or in vivo. Production of high titres of Mabs in vivo makes this the presently preferred method of production.

In addition, techniques developed for the production of "chimeric antibodies" by splicing the genes from a mouse antibody molecule of appropriate antigen specificity together with genes from a human antibody molecule of appropriate biological activity can be used (Morrison et al., 1984, *Proc. Nat'l. Acad. Sci.,* 81: 6851-6855; Neuberger et al., 1984, *Nature,* 312: 604-608; Takeda et al. 1985, *Nature* 314: 452-454). Alternatively, techniques developed for the production of humanized antibodies (U.S. Pat. No. 5,585,089) or single chain antibodies (U.S. Pat. No. 4,946,778 Bird, 1988, *Science* 242: 423-426; Huston et al., 1988, *Proc. Nat'l. Acad. Sci USA,* 85: 5879-5883; and Ward et al., 1989, *Nature* 334: 544-546) may be used to produce antibodies that specifically recognize one or more epitopes of T1R3.

Screening Assays for Drugs and Other Chemical Compounds Useful in Regulation of Taste Perception The present invention relates to screening assay systems designed to identify compounds or compositions that modulate T1R3 activity or T1R3 gene expression, and thus, may be useful for modulation of sweet taste perception.

The present invention also relates to screening assay systems designed to identify compounds or compositions that modulate T1R3 activity or T1R3 gene expression, and thus, may be useful for modulation of umami taste perception.

In accordance with the invention, a cell-based assay system can be used to screen for compounds that modulate the activity of the T1R3 and thereby, modulate the perception of sweetness. To this end, cells that endogenously express T1R3 can be used to screen for compounds. Alternatively, cell lines, such as 293 cells, COS cells, CHO cells, fibroblasts, and the like, genetically engineered to express T1R3 can be used for screening purposes. Preferably, host cells genetically engineered to express a functional T1R3 re those that respond to activation by sweet tastants, such as taste receptor cells. Further, ooyctes or liposomes engineered to express T1R3 may be used in assays developed to identify modulators of T1R3 activity.

The present invention provides for methods for identifying a compound that induces the perception of a sweet taste (a "sweetness activator") comprising (i) contacting a cell expressing the T1R3 receptor with a test compound and measuring the level of T1R3 activation; (ii) in a separate experiment, contacting a cell expressing the T1R3 receptor protein with a vehicle control and measuring the level of T1R3 activation where the conditions are essentially the same as in part (i), and then (iii) comparing the level of activation of T1R3 measured in part (i) with the level of activation of T1R3 in part (ii), wherein an increased level of activated T1R3 in the presence of the test compound indicates that the test compound is a T1R3 activator.

The present invention also provides for methods for identifying a compound that inhibits the perception of a sweet taste (a "sweetness inhibitor") comprising (i) contacting a cell expressing the T1R3 receptor protein with a test compound in the presence of a sweet tastant and measuring the level of T1R3 activation; (ii) in a separate experiment, contacting a cell expressing the T1R3 receptor protein with a sweet tastant and measuring the level of T1R3 activation, where the conditions are essentially the same as in part (i) and then (iii) comparing the level of activation of T1R3 measured in part (i) with the level of activation of T1R3 in part (ii), wherein a decreased level of activation of T1R3 in the presence of the test compound indicates that the test compound is a T1R3 inhibitor.

A "sweet tastant", as defined herein, is a compound or molecular complex that induces, in a subject, the perception of a sweet taste. In particular, a sweet tastant is one which results in the activation of the T1R3 protein resulting in one or more of the following: (i) an influx of $Ca^{2+}$ into the cell; (ii) release of $Ca^{2+}$ from internal stores; (iii) activation of coupled G proteins such as Gs and/or gustducin; (iv) activation of second messenger-regulating enzymes such as adenylyl cyclase and/or phospholipase C. Examples of sweet tastants include but are not limited to saccharin or sucrose, or other sweeteners.

In some embodiments, the sweet tastant is a natural sweetener. Examples of natural sweeteners include glucose, sucrose, maltose, fructose, sorbitol, D-tryptophan and trehalose. In other embodiments, the sweet tastant is an artificial sweetener. Examples of artificial sweeteners include sucralose, saccharin, acesulfame K, SC45647, aspartame, monellin, thaumatin and brazzein. It should be noted that only humans, apes and old world monkeys perceive artificial sweeteners such as aspartame, monellin, thaumatin and brazzein as sweet.

An "umami tastant", as defined herein, is a compound or molecular complex that induces, in a subject, the perception of an umami taste. In particular, an umami tastant is one which results in the activation of the T1R3 protein resulting in one or more of the following: (i) an influx of $Ca^{2+}$ into the cell; (ii) release of $Ca^{2+}$ from internal stores; (iii) activation of coupled G proteins such as Gs, Gi, transducin and/or gustducin; (iv) activation of second messenger-regulating enzymes such as adenylyl cyclase and/or phospholipase C. Examples of umami tastants include but are not limited to monosodium glutamate (MSG), inosine monophosphate (IMP) and combinations of MSG and IMP.

In utilizing such cell systems, the cells expressing the T1R3 receptor are exposed to a test compound or to vehicle controls (e.g., placebos). After exposure, the cells can be assayed to measure the expression and/or activity of components of the signal transduction pathway of T1R3, or the activity of the signal transduction pathway itself can be assayed.

Also within the scope of the present invention are assay systems that make use of the transgenic cells or the present invention, or taste buds or tissue slices derived from the transgenic animals of the present invention. These assays may be used to screen for compounds that modulate activity or expression of components of the T1R3 signal transduction pathway, thereby mimicking or modulating the perception of sweet or umami tastants. Components of the T1R3 signal transduction pathway include, e.g., the T1R3 receptor, ion channels and other signal transduction elements. In a preferred embodiment, the cells, taste buds or tissue slices used in these assays are derived from T1R3 knock-out animals. In another preferred embodiment, the cells, taste buds or tissue slices used in these assays are derived from T1R3 knock-out animals that are capable of expressing a non-native T1R3 protein. In a more preferred embodiment, the cells, taste buds or tissue slices are derived from T1R3 knock-out mice.

In utilizing such systems, the transgenic cells, taste buds or tissue slices are exposed to a test compound or mixture of compounds. After exposure, the cells, taste buds or tissue slices can be assayed to measure the expression and/or activity of components of the T1R3 signal transduction pathway, or the activity of the T1R3 signal transduction pathway itself can be assayed. This response can then be compared with the response exhibited by wild-type or other T1R3-containing cells, taste buds or tissue slices exposed to the same test compound or mixture of compounds. If the compounds act through the T1R3 pathway, one would expect the response of transgenic cells, taste buds or tissue slices to differ from the response of T1R3-containing cells, taste buds or tissue slices. If there is no such difference with a particular test compound or mixture of compounds, then its mode of action is through a T1R3-independent pathway. In this way, compounds that act via components of the T1R3 signal transduction pathway can be identified and their effects examined.

Thus, the present invention provides for a method of identifying a modulator of T1R3-mediated signal transduction, comprising the steps of:

(a) administering a test compound or mixture of compounds to a transgenic non-human mammalian cell, wherein the cell is heterozygous or homozygous for a nonfunctional T1R3 gene, and evaluating the effect of the test compound or mixture of compounds on the cell;

(b) in a separate experiment, where the conditions are essentially the same as in step (a), administering the test compound or mixture of compounds to a T1R3-expressing non-human mammalian cell, and evaluating the effect of the test compound or mixture of compounds on the cell; and (c) comparing the effect in step (a) with the effect in step (b), wherein a difference in effect indicates that the test compound or mixture of compounds modulates T1R3-mediated signal transduction.

The present invention also relates to a method of identifying a modulator of T1R3-mediated signal transduction, comprising the steps of:

(a) administering a test compound or mixture of compounds to a tissue slice derived from a transgenic non-human mammal, wherein the transgenic mammal is heterozygous or homozygous for a nonfunctional T1R3 gene, and evaluating the effect of the test compound or mixture of compounds on the tissue slice;

(b) in a separate experiment, where the conditions are essentially the same as in step (a), administering the test compound or mixture of compounds to a tissue slice derived from a T1R3-expressing non-human mammal, and evaluating the effect of the test compound or mixture of compounds on the tissue slice; and (c) comparing the effect in step (a) with the effect in step (b), wherein a difference in effect indicates that the test compound or mixture of compounds modulates T1R3-mediated signal transduction.

The present invention also provides for a method of identifying a modulator of T1R3-mediated signal transduction, comprising the steps of:

(a) administering a test compound or mixture of compounds to a taste bud derived from a transgenic non-human mammal, wherein the transgenic mammal is heterozygous or homozygous for a nonfunctional T1R3 gene, and evaluating the effect of the test compound or mixture of compounds on the taste bud;

(b) in a separate experiment, where the conditions are essentially the same as in step (a), administering the test compound or mixture of compounds to a taste bud derived from a T1R3-expressing non-human mammal, and evaluating the effect of the test compound or mixture of compounds on the taste bud; and (c) comparing the effect in step (a) with the effect in step (b), wherein a difference in effect indicates that the test compound or mixture of compounds modulates T1R3-mediated signal transduction.

In some embodiments of the assays described above, the modulator induces the perception of a sweet taste or an umami taste. In some embodiments, the modulator inhibits the perception of a sweet taste or an umami taste. In some embodiments, the modulator in combination with a low level of tastant enhances the perception of a sweet taste or an umami taste. In some embodiments, the modulator in combination with a tastant reduces the perception of a sweet taste or an umami taste. In some embodiments, the mammal is a mouse.

Assays based on the transgenic cells disclosed herein, or taste buds or tissue slices derived from the transgenic animals disclosed herein may also be used to study the T1R3 signal transduction pathway and the in vivo function of components of that pathway. For example, these assays may be used to characterize the effect of known tastants or taste modulators on the expression or activity of T1R3 or some other component of the T1R3 signal transduction pathway, such as, for example, a T1R3-associated G protein. In a preferred embodiment, the cells, taste buds or tissue slices used in such assays are derived from knock-out animals. In another preferred embodiment, the cells, taste buds or tissue slices used in such assays are derived from knock-out animals that are capable of expressing a non-native T1R3 protein. In a more preferred embodiment, the cells, taste buds or tissue slices are derived from knock-out mice.

In utilizing such systems, the transgenic cells, taste buds or tissue slices are exposed to a tastant. After exposure, the cells, taste buds or tissue slices can be assayed to measure the expression and/or activity of components of the T1R3 signal transduction pathway, or the activity of the T1R3 signal transduction pathway itself can be assayed. This response can then be compared with the response exhibited by wild-type or other T1R3-containing cells, taste buds or tissue slices exposed to the same tastant. If the tastant acts through the T1R3 pathway, one would expect the response of transgenic cells, taste buds or tissue slices to differ from the response of T1R3-containing cells, taste buds or tissue slices. If there is no such difference with a particular tastant, then its mode of action is through a T1R3-independent pathway. In this way, the effects of tastants can be studied.

The present invention encompasses a method of determining whether a tastant affects T1R3-mediated signal transduction, comprising the steps of:

(a) administering a tastant to a transgenic non-human mammalian cell, wherein the cell is heterozygous or homozygous for a nonfunctional T1R3 gene, and evaluating the effect of the tastant on the cell;

(b) in a separate experiment, where the conditions are essentially the same as in step (a), administering the tastant to a T1R3-expressing non-human mammalian cell, and evaluating the effect of the tastant on the cell; and (c) comparing the effect in step (a) with the effect in step (b), wherein a difference in effect indicates that the tastant affects T1R3-mediated signal transduction.

The present invention also provides for a method of determining whether a tastant affects T1R3-mediated signal transduction, comprising the steps of:

(a) administering a tastant to a tissue slice derived from a transgenic non-human mammal, wherein the transgenic mammal is heterozygous or homozygous for a nonfunctional T1R3 gene, and evaluating the effect of the tastant on the tissue slice;

(b) in a separate experiment, where the conditions are essentially the same as in step (a), administering the tastant to a tissue slice derived from a T1R3-expressing non-human mammal, and evaluating the effect of the tastant on the tissue slice; and (c) comparing the effect in step (a) with the effect in step (b), wherein a difference in effect indicates that the tastant affects T1R3-mediated signal transduction.

Also within the scope of the present invention is a method of determining whether a tastant affects T1R3-mediated signal transduction, comprising the steps of:

(a) administering a tastant to a taste bud derived from a transgenic non-human mammal, wherein the transgenic mammal is heterozygous or homozygous for a nonfunctional T1R3 gene, and evaluating the effect of the tastant on the taste bud;

(b) in a separate experiment, where the conditions are essentially the same as in step (a), administering the tastant to a taste bud derived from a T1R3-expressing non-human mammal, and evaluating the effect of the tastant on the taste bud; and (c) comparing the effect in step (a) with the effect in step (b), wherein a difference in effect indicates that the tastant affects T1R3-mediated signal transduction.

In some embodiments, the tastant is a sweet tastant. The sweet tastant may be a natural sweetener such as glucose, sucrose, maltose, fructose, trehalose, sorbitol or D-tryptophan. The sweet tastant may also be an artificial sweetener such as sucralose, saccharin, acesulfame K, SC45647, brazzein, monellin, aspartame or thaumatin. In some embodiments, the tastant is an umami tastant. Examples of umami tastants include MSG, IMP and combinations thereof. In some embodiments, the effect of the tastant on the cell, tissue slice or taste bud derived from the transgenic animal is reduced in comparison to that in the T1R3-expressing animal, indicating that the tastant acts through the T1R3 signal transduction pathway.

The ability of a test molecule to modulate the activity of T1R3 may be measured using standard biochemical and physiological techniques. Responses such as activation or suppression of catalytic activity, phosphorylation or dephosphorylation of T1R3 and/or other proteins, activation or modulation of second messenger production, changes in cellular ion levels, association, dissociation or translocation of signaling molecules, or transcription or translation of specific genes may be monitored. In nonlimiting embodiments of the invention, changes in intracellular $Ca^{2+}$ levels may be monitored by the fluorescence of indicator dyes such as indo, fura, etc. Additionally, changes in cAMP, cGMP, $IP_3$, and DAG levels may be assayed. In yet another embodiment, activation of adenylyl cyclase, guanylyl cyclase, protein kinase A and $Ca^{2+}$ sensitive release of neurotransmitters may be measured to identify compounds that modulate T1R3 signal transduction. Further, changes in membrane potential resulting from modulation of the T1R3 channel protein can be measured using a voltage clamp or patch recording methods. In yet another embodiment of the invention, a microphysiometer can be used to monitor cellular activity.

In another embodiment, effects on phosphodiesterase (PDE) levels may be assayed to identify compounds that modulate T1R3 signal transduction.

For example, after exposure to a test compound, cell lysates can be assayed for increased intracellular levels of $Ca^{2+}$ and activation of calcium dependent downstream messengers such as adenylyl cyclase, protein kinase A or cAMP. The ability of a test compound to increase intracellular levels of $Ca^{2+}$, activate protein kinase A or increase cAMP levels in a cell expressing the T1R3 receptor compared to those levels seen with cells treated with a vehicle control, indicates that the test compound acts as an agonist (i.e., is a T1R3 activator) and induces signal transduction mediated by the T1R3 expressed by the host cell. The ability of a test compound to inhibit sweet tastant induced calcium influx, inhibit protein kinase A or decrease cAMP levels in a cell expressing the T1R3 receptor compared to those levels seen with a vehicle control indicates that the test compound acts as an antagonist (i.e., is a T1R3 inhibitor) and inhibits signal transduction mediated by T1R3.

In other embodiments of the present invention, the ability of a test compound to increase intracellular levels of $Ca^{2+}$, activate protein kinase A or increase cAMP levels in T1R3-containing cells, taste buds or tissue slices compared to those levels seen with transgenic cells, taste buds or tissue slices, particularly knock-out cells or tissue slices, indicates that the test compound stimulates expression or activity of a component of the T1R3 signal transduction pathway, inducing T1R3-mediated signal transduction. The ability of a test compound to increase intracellular levels of $Ca^{2+}$, activate protein kinase A or increase cAMP levels to the same extent in both T1R3-containing cells, taste buds or tissue slices and transgenic cells, taste buds or tissue slices, particularly knock-out cells, taste buds or tissue slices, indicates that the test compound acts through a T1R3-independent pathway.

In a specific embodiment of the invention, levels of cAMP can be measured using constructs containing the cAMP responsive element linked to any of a variety of different reporter genes. Such reporter genes may include but are not limited to chloramphenicol acetyltransferase (CAT), luciferase, β-glucuronidase (GUS), growth hormone, or placentalalkaline-phosphatase (SEAP). Such constructs are introduced into cells expressing T1R3 thereby providing a recombinant cell useful for screening assays designed to identify modulators of T1R3 activity.

Following exposure of the cells to the test compound, the level of reporter gene expression may be quantitated to determine the test compound's ability to regulate T1R3 activity. Alkaline phosphatase assays are particularly useful in the practice of the invention as the enzyme is secreted from the cell. Therefore, tissue culture supernatant may be assayed for secreted alkaline phosphatase. In addition, alkaline phosphatase activity may be measured by calorimetric, bioluminescent or chemiluminescent assays such as those described in Bronstein, I. et al., *Biotechniques,* 17: 172-177 (1994). Such assays provide a simple, sensitive easily automatable detection system for pharmaceutical screening.

Additionally, to determine intracellular cAMP concentrations, a scintillation proximity assay (SPA) may be utilized (SPA kit is provided by Amersham Life Sciences, Illinois). The assay utilizes $^{125}$I-label cAMP, an anti-cAMP antibody, and a scintillant-incorporated microsphere coated with a secondary antibody. When brought into close proximity to the microsphere through the labeled cAMPantibody complex, $^{125}$I, will excite the scintillant to emit light. Unlabeled cAMP extracted from cells competes with the $^{125}$I-labeled cAMP for binding to the antibody and thereby diminishes scintillation. The assay may be performed in 96-well plates to enable high-throughput screening and 96 well-based scintillation counting instruments such as those manufactured by Wallac or Packard may be used for readout.

In yet another embodiment of the invention, levels of intracellular $Ca^{2+}$ can be monitored using $Ca^{2+}$ indication dyes, such as Fluo-3 and Fura-Red using methods such as those described in Komuro and Rakic, *The Neuron in Tissue Culture* (L. W. Haymes, Ed. Wiley, New York 1998).

Test activators which activate T1R3, identified by any of the above methods, may be subjected to further testing to confirm their ability to induce an umami perception. Test inhibitors which inhibit the activation of T1R3 by umami tastants, identified by any of the above methods, may then be subjected to further testing to confirm their inhibitory activity.

Test activators which activate the activity of T1R3, identified by any of the above methods, may be subjected to further testing to confirm their ability to induce a sweetness perception. Test inhibitors which inhibit the activation of T1R3 by sweet tastants, identified by any of the above methods, may then be subjected to further testing to confirm their inhibitory activity. The ability of the test compound to modulate the activity of the T1R3 receptor may be evaluated by behavioral, physiologic, or in vitro methods.

For example, a behavioral study may be performed where a test animal may be offered the choice of consuming a composition comprising the putative T1R3 activator and the same composition without the added compound. A preference for the composition comprising a test compound, indicated, for example, by greater consumption, would have a positive correlation with activation of T1R3 activity. Additionally, lack of preference by a test animal of food containing a putative inhibitor of T1R3 in the presence of a sweetener would have a positive correlation with the identification of an sweetness inhibitor.

In addition to cell based assays, non-cell based assay systems may be used to identify compounds that interact with, e.g., bind to T1R3. Such compounds may act as antagonists or agonists of T1R3 activity and may be used to regulate sweet taste perception.

To this end, soluble T1R3 may be recombinantly expressed and utilized in non-cell based assays to identify compounds that bind to T1R3. The recombinantly expressed T1R3 polypeptides or fusion proteins containing one or more of the domains of T1R3 prepared as described in Section 5.2, infra, can be used in the non-cell based screening assays. For example, peptides corresponding to the amino terminal domain that is believed to be involved in ligand binding and dimerization, the cysteine rich domain and/or the transmembrane spanning domains of T1R3, or fusion proteins containing one or more of the domains of T1R3 can be used in non-cell based assay systems to identify compounds that bind to a portion of the T1R3; such compounds may be useful to modulate the signal transduction pathway of the T1R3. In non-cell based assays the recombinantly expressed T1R3 may be attached to a solid substrate such as a test tube, microtitre well or a column, by means well known to those in the art (see Ausubel et al., supra). The test compounds are then assayed for their ability to bind to the T1R3.

The T1R3 protein may be one which has been fully or partially isolated from other molecules, or which may be present as part of a crude or semi-purified extract. As a non-limiting example, the T1R3 protein may be present in a preparation of taste receptor cell membranes. In particular embodiments of the invention, such taste receptor cell membranes may be prepared as set forth in Ming, D. et al., *Proc. Natl. Sci. U.S.A.,* 95: 8933-8938 (1998), incorporated by reference herein. Specifically, bovine circumvallate papillae ("taste tissue", containing taste receptor cells), may be hand dissected, frozen in liquid nitrogen, and stored at −80EC prior to use. The collected tissues may then be homogenized with a Polytron homogenizer (three cycles of 20 seconds each at 25,000 RPM) in a buffer containing 10 mM Tris at pH 7.5, 10% vol/vol glycerol, 1 mM EDTA, 1 mM DTT, 10 pg/pl pepstatin A, 10 μg/pl leupeptin, 10 μg/μl aprotinin, and 100 μM 4-(2-amino ethyl) benzenesulfoyl fluoride hydrochloride. After particulate removal by centrifugation at 1,500×g for 10 minutes, taste membranes may be collected by centrifugation at 45,000×g for 60 minutes. The pelleted membranes may then be rinsed twice, re-suspended in homogenization buffer lacking protease inhibitors, and further homogenized by 20 passages through a 25 gauge needle. Aliquots may then be either flash frozen or stored on ice until use. As another non-limiting example, the taste receptor may be derived from recombinant clones (see Hoon, M. R. et al., *Cell,* 96: 541-551 (1999)).

Assays may also be designed to screen for compounds that regulate T1R3 expression at either the transcriptional or translational level. In one embodiment, DNA encoding a reporter molecule can be linked to a regulatory element of the T1R3 gene and used in appropriate intact cells, cell extracts or lysates to identify compounds that modulate T1R3 gene expression. Appropriate cells or cell extracts are prepared from any cell type that normally expresses the T1R3 gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

To identify compounds that regulate T1R3 translation, cells or in vitro cell lysates containing T1R3 transcripts may be tested for modulation of T1R3 mRNA translation. To assay for inhibitors of T1R3 translation, test compounds are assayed for their ability to modulate the translation of T1R3 mRNA in in vitro translation extracts.

In addition, compounds that regulate T1R3 activity may be identified using animal models. Behavioral, physiological, or biochemical methods may be used to determine whether T1R3 activation has occurred. Behavioral and physiological methods may be practiced in vivo. As an example of a behavioral measurement, the tendency of a test animal to voluntarily ingest a composition, in the presence or absence of test activator, may be measured. If the test activator induces T1R3 activity in the animal, the animal may be expected to experience a sweet taste, which would encourage it to ingest more of the composition. If the animal is given a choice of whether to consume a composition containing a sweet tastant only (which activates T1R3) or a composition containing a test inhibitor together with a sweet tastant, it would be expected to prefer to consume the composition containing sweet tastant only. Thus, the relative preference demonstrated by the animal inversely correlates with the activation of the T1R3 receptor.

As another example of a behavioral measurement, the tendency of knock-out and T1R3-expressing animals to voluntarily ingest a composition containing a test compound may be compared. If the test compound stimulates expression or activity of a component of the T1R3 signal transduction pathway, only the T1R3-expressing animal would be expected to experience a sweet or umami taste, which would encourage it to ingest more of the composition. If a T1R3-expressing animal is given a choice of whether to consume a composition containing the test compound (that induces T1R3-mediated signal transduction) or a composition lacking the test compound, it would be expected to prefer to consume the composition containing the test compound. The knock-out animal, in contrast, would not be expected to exhibit a preference. Thus, a preference demonstrated by a T1R3-expressing animal and not by a knock-out animal correlates with stimulation of an element of the T1R3 signal transduction pathway. Alternatively, if the test compound acts through a T1R3-independent pathway, the preferences exhibited by the T1R3-expressing and knock-out animals should be the same.

Thus, the present invention provides for a method of identifying a modulator of T1R3-mediated signal transduction, comprising the steps of:

(a) administering a test compound or mixture of compounds to a transgenic non-human mammal, wherein the transgenic mammal is heterozygous or homozygous for a nonfunctional T1R3 gene, and evaluating the effect of the test compound or mixture of compounds on the transgenic mammal;

(b) in a separate experiment, where the conditions are essentially the same as in step (a), administering the test compound or mixture of compounds to a T1R3-expressing non-human mammal, and evaluating the effect of the test compound or mixture of compounds on the T1R3-expressing mammal; and (c) comparing the effect in step (a) with the effect in step (b), wherein a difference in effect indicates that the test compound or mixture of compounds modulates T1R3-mediated signal transduction.

In some embodiments of the assay described above, the modulator induces the perception of a sweet taste or an umami taste. In some embodiments, the modulator inhibits the perception of a sweet taste or an umami taste. In some embodiments, the modulator in combination with a low level of tastant enhances the perception of a sweet taste or an umami taste. In some embodiments, the modulator in combination with a tastant reduces the perception of a sweet taste or an umami taste. In some embodiments, the mammal is a mouse.

Also within the scope of the present invention is the use of animal models to study the T1R3 signal transduction pathway and the in vivo function of components of that pathway. For example, these assays may be used to characterize the effect of known tastants or taste modulators on the expression or activity of T1R3 or some other component of the T1R3 signal transduction pathway, such as, for example, a T1R3-associated G protein. In a preferred embodiment, the knock-out animals used in such assays are knock-out mice.

As an example, the effect of a known sweet or umami tastant on T1R3-expressing and knock-out animals may be compared. If the tastant acts solely through a component of the T1R3 signal transduction pathway, only the T1R3-expressing animal would be expected to experience a sweet or umami taste, which would encourage it to prefer compositions containing the tastant. The knock-out animal, in contrast, would be expected to exhibit no preference for the composition containing the tastant. Thus, a preference exhibited by the T1R3-containing animal and not by the knock-out animal indicates that the tastant acts through the T1R3 signal transduction pathway. In contrast, a finding that both the T1R3-containing animal and the knock-out animal prefer the composition containing the tastant would indicate that the tastant acts though a T1R3-independent pathway. A finding that the knock-out animal exhibits some preference for the tastant-containing composition, but less than the preference exhibited by the T1R3-containing animal, would suggest that the tastant acts through both the T1R3 pathway and at least a second pathway.

Thus, the present invention encompasses a method of determining whether a tastant affects T1R3-mediated signal transduction, comprising the steps of:

(a) administering a tastant to a transgenic non-human mammal, wherein the transgenic mammal is heterozygous or homozygous for a nonfunctional T1R3 gene, and evaluating the effect of the tastant on the transgenic mammal;

(b) in a separate experiment, where the conditions are essentially the same as in step (a), administering the tastant to a T1R3-expressing non-human mammal, and evaluating the effect of the tastant on the T1R3-expressing mammal; and (c) comparing the effect in step (a) with the effect in step (b), wherein a difference in effect indicates that the tastant affects T1R3-mediated signal transduction.

In some embodiments of the animal model assay described above, the tastant is a sweet tastant. For example, the tastant may be a natural sweetener or an artificial sweetener. In some embodiments, the tastant is an umami tastant. In some embodiments, the effect of the tastant on the knock-out animal is lower than that in the T1R3-expressing animal, indicating that the tastant stimulates T1R3-mediated signal transduction.

In some embodiments of each of the animal model assays described above, the effect of the modulator or tastant is assessed using a behavioral assay. Specific behavioral tests that were performed on T1R3 knock-out and wild-type mice are described in Example 3. In some embodiments, the effect of the modulator or tastant is assessed by electrophysiological measurement of neural activity. Specific electrophysiological studies that were performed on T1R3 knock-out and wild-type mice are described in Example 4.

Specific types of behavioral assays useful in the present invention include, for example, lickometer assays, two-bottle preference assays, and conditioned taste aversion assays.

Physiological methods include nerve response studies, which may be performed using a nerve operably joined to a taste receptor cell containing tissue, in vivo or in vitro. Since exposure to sweet tastant which results in T1R3 activation may result in an action potential in taste receptor cells that is then propagated through a peripheral nerve, measuring a nerve response to a sweet tastant is, inter alia, an indirect measurement of T1R3 activation. An example of nerve response studies performed using the glossopharyngeal nerve are described in Ninomiya, Y. et al., *Am. J. Physiol. (London)*, 272: R1002-R1006 (1997).

The assays described above can identify compounds which modulate T1R3 activity. For example, compounds that affect T1R3 activity include but are not limited to compounds that bind to the T1R3, and either activate signal transduction (agonists) or block activation (antagonists). Compounds that affect T1R3 gene activity (by affecting T1R3 gene expression, including molecules, e.g., proteins or small organic molecules, that affect transcription or interfere with splicing events so that expression of the full length or the truncated form of the T1R3 can be modulated) can also be identified using the screens of the invention. However, it should be noted that the assays described can also identify compounds that modulate T1R3 signal transduction (e.g., compounds which affect downstream signaling events, such as inhibitors or enhancers of G protein activities which participate in transducing the signal activated by tastants binding to their receptor). The identification and use of such compounds which affect signaling events downstream of T1R3 and thus modulate effects of T1R3 on the perception of taste are within the scope of the invention.

The compounds which may be screened in accordance with the invention include, but are not limited to, small organic or inorganic compounds, peptides, antibodies and fragments thereof, and other organic compounds (e.g., peptidomimetics) that bind to T1R3 and either mimic the activity triggered by the natural tastant ligand (i.e., agonists) or inhibit the activity triggered by the natural ligand (i.e., antagonists). Such compounds may be naturally occurring compounds such as those present in fermentation broths, cheeses, plants, and fungi, for example.

Compounds may include, but are not limited to, peptides such as, for example, soluble peptides, including but not limited to members of random peptide libraries (see, e.g., Lam, K. S. et al., *Nature*, 354: 82-84 (1991); Houghten, R. et al., 1991, *Nature*, 354: 84-86 (1991)); and combinatorial chemistry-derived molecular library made of D- and/or L-configuration amino acids, phosphopeptides (including, but not limited to, members of random or partially degenerate, directed phosphopeptide libraries; (see, e.g., Songyang, Z. et al., *Cell*, 72: 767-778 (1993)), antibodies (including, but not limited to, polyclonal, monoclonal, humanized, anti-idiotypic, chimeric or single chain antibodies, and FAb, F(ab')$_2$ and FAb expression library fragments, and epitope binding fragments thereof), and small organic or inorganic molecules.

Other compounds which may be screened in accordance with the invention include but are not limited to small organic molecules that affect the expression of the T1R3 gene or some other gene involved in the T1R3 signal transduction pathway (e.g., by interacting with the regulatory region or transcription factors involved in gene expression); or such compounds that affect the activity of the T1R3 or the activity of some other intracellular factor involved in the T1R3 signal transduction pathway, such as, for example, a T1R3 associated G-protein.

Compositions Containing Modulators of T1R3 and their Uses

The present invention provides for methods of inducing a sweet taste resulting from contacting a taste tissue of a subject with a sweet tastant, comprising administering to the subject an effective amount of a T1R3 activator, such as a T1R3 activator identified by measuring T1R3 activation as set forth in Section 5.5 supra. The present invention also provides for methods of inhibiting the sweet taste of a composition, comprising incorporating, in the composition, an effective amount of a T1R3 inhibitor. An "effective amount" of the T1R3 inhibitor is an amount that subjectively decreases the perception of sweet taste and/or that is associated with a detectable decrease in T1R3 activation as measured by one of the above assays.

The present invention further provides for a method of producing the perception of a sweet taste by a subject, comprising administering, to the subject, a composition comprising a compound that activates T1R3 activity such as a sweetness activator identified as set forth in Section 5.5 supra. The composition may comprise an amount of activator that is effective in producing a taste recognized as sweet by a subject.

Accordingly, the present invention provides for compositions comprising sweetness activators and sweetness inhibitors. Such compositions include any, substances which may come in contact with taste tissue of a subject, including but not limited to foods, beverages, pharmaceuticals, dental products, cosmetics, and wettable glues used for envelopes and stamps.

In one set of embodiments of the invention, T1R3 activators are utilized as food or beverage sweeteners. In such instances, the T1R3 activators of the invention are incorporated into foods or beverages, thereby enhancing the sweet flavor of the food or beverage without increasing the carbohydrate content of the food.

In another embodiment of the invention, a sweetness activator is used to counteract the perception of bitterness associated with a co-present bitter tastant. In these embodiments, a composition of the invention comprises a bitter tastant and a sweetness activator, where the sweetness activator is present at a concentration which inhibits bitter taste perception. For example, when the concentration of bitter tastant in the composition and the concentration of sweetness activator in the composition are subjected to an assay as disclosed in Section 5.1 supra.

The present invention may be used to improve the taste of foods by increasing the perception of sweetness or by decreasing or eliminating the aversive effects of bitter tastants. If a bitter tastant is a food preservative, the T1R3 activators of the invention may permit or facilitate its incorporation into foods, thereby improving food safety. For foods administered as nutritional supplements, the incorporation of T1R3 activators of the invention may encourage ingestion, thereby enhancing the effectiveness of these compositions in providing nutrition or calories to a subject.

The T1R3 activators of the invention may be incorporated into medical and/or dental compositions. Certain compositions used in diagnostic procedures have an unpleasant taste, such as contrast materials and local oral anesthetics. The T1R3 activators of the invention may be used to improve the comfort of subjects undergoing such procedures by improving the taste of compositions. In addition, the T1R3 activators of the invention may be incorporated into pharmaceutical compositions, including tablets and liquids, to improve their flavor and improve patient compliance (particularly where the patient is a child or a non-human animal).

The T1R3 activators of the invention may be comprised in cosmetics to improve their taste features. For example, but not by way of limitation, the T1R3 activators of the invention may be incorporated into face creams and lipsticks. In addition, the T1R3 activators of the invention may be incorporated into compositions that are not traditional foods, beverages, Pharmaceuticals, or cosmetics, but which may contact taste membranes. Examples include, but are not limited to, soaps, shampoos, toothpaste, denture adhesive, glue on the surfaces of stamps and envelopes, and toxic compositions used in pest control (e.g., rat or cockroach poison).

Example

Cloning and Characterization of the T1R3 Gene

The data presented below describes the identification of a novel taste receptor, T1R3, as being Sac. This identification is based on the following observations. T1R3 is the only GPCR present in a 1 million bp region of human genomic DNA centered on the D18346 marker most tightly linked to Sac. Expression of T1R3 is narrowly restricted and is highly expressed in a subset of taste receptor cells. Expression of T1R3 in taste receptor cells overlaps in large part with known and proposed elements of sweet transduction pathways (i.e. α-gustducin, Gγ13. T1R3 is a family 3 GPCR with a large extracellular domain sensitive to proteases (a known property of the sweet receptor). Most tellingly, a polymorphism in T1R-3 was identified that differentiated all taster strains of mice from all non-taster strains: T1R3 from non-tasters is predicted to contain an N-terminal glycosylation site that based on modeling of T1R3's structure would be expected to interfere with its dimerization. Hence, not only is T1R3 identified as sac, but based on the model of T1R3 and this polymorphic change it is also likely to be a sweet-responsive (i.e. sweet-liganded) taste receptor.

Gene Identification

To identify the mouse gene (pseudouridine synthase-like) containing the D18346 marker the D18346 sequence was used as a query sequence in a BlastN screen of the mouse expressed sequence tag (est) database. Each resulting overlapping sequence match was used iteratively to extend the sequence until the nearly full length gene was determined. The resulting contig was translated and the predicted open reading frame was used as a query in a TBlastN search of the High Throughput Genomic Sequence (HTGS) database. This search located a human BAC clone AL139287 containing the human ortholog. Genscan was used to predict genes and exons in this clone. BlastN or TBlastN searches of either the NR or the est databases were used to further define known or unknown genes in this and other clones. Each resulting predicted gene was used in TBlastN or BlastN searches of the HTGS to find overlapping BAC or PAC clones. Each of the overlapping sequences was used in BlastN searches of the HTGS to continue the build of an unordered contig of the region. The predicted genes and exons that resulted from this search were used to partially order over 1 million bases of genomic sequence centered on the pseudouridine synthase-like gene containing the D18346 marker. Two human clones were found to contain T1R3, the aforementioned AL139287 and AC026283. The human T1R3 gene was first predicted by Genscan and subsequently confirmed by RT-PCR of human fungiform taste bud RNA and/or screening of a human taste library. In addition to the above manipulations and searches we used an algorithm (designed to recognize transmembrane spans in genomic sequence) to search all of the human genomic clones on the p arm of human chromosome 1 from lpter to lp33 (Sanger Center chromosome 1 mapping project, FC and HW, unpublished). This screen predicted T1R3 as well as T1R1 and T1R2. Human T1R3 lies within 20,000 bp of the D18346 marker and the pseudouridine synthase-like gene and is the only predicted GPCR in this 1 million bp region.

The human predicted gene was then used in a TBlastN screen of the Celera mouse fragment genomic database. Each matching fragment was used to fill gaps and further extend the mouse T1R3 ortholog in repeated BlastN searches. The following mouse fragments were used to build and refine the mouse T1R3 genomic sequence: GA_49588987, GA_72283785, GA_49904613, GA_50376636, GA_74432413, GA_70914196, GA_62197520/GA_77291497, GA_74059038, GA_66556470, GA_70030888/GA_50488116, GA_50689730, GA_72936925, GA_72154490, GA_69808702. Genscan was used to predict the mouse gene from the resulting genomic contig. The predicted mouse T1R3 gene was confirmed by RT-PCR of mouse taste bud RNA. Other genes from the human genomic region centered on D18346 were used to search the Celera mouse fragments database. The sequences from these searches were used to build a mouse genomic contig of this region and confirm the linkage of D18346 with T1R3 in the mouse genome and the microsynteny of the human and mouse genes in this region. One gap in the genomic sequence, between the 5'-end of T1R3 and the 3'-end of the glycolipid-transferase-like gene was bridged by PCR and confirmed by sequence analysis.

Northern Hybridization

Total RNAs were isolated from several mouse tissues using the Trizol reagents, then 25 μg of each RNA was electrophoresed per lane on a 1.5% agarose gel containing 6.7% formaldehyde. The samples were transferred and fixed to a nylon membrane by UV irradiation. The blot was prehybridized at 65° C. in 0.25 M sodium phosphate buffer (pH 7.2) containing 7% SDS and 40 μg/ml herring sperm DNA with agitation for 5 hours; hybridization for 20 hours with the 32P-radiolabeled mouse T1R3 probe was carried out in the same solution. The membrane was washed twice at 65° C. in 20 mM sodium phosphate buffer (pH 7.2) containing 5% SDS for 40 minutes, twice at 65° C. in the same buffer containing 1% SDS for 40 minutes, and once at 70° C. in 0.1×SSC and 0.1% SDS for 30 minutes. The blot was exposed to X-ray film for 3 days at 80° C. with dual intensifying screens. The 32P-labeled T1R3 probe was generated by random nonamer priming of a 1.34-kb cDNA fragment of murine T1R3 corresponding to the 5'-end coding sequence using Exo(−) Klenow polymerase in the presence of (α-32P)-dCTP.

In Situ Hybridization 33P-labeled RNA probes T1R3 (2.6 kb) and α-gustducin (1 kb)] were used for in situ hybridization of frozen sections (10 μm) of mouse lingual tissue. Hybridization and washing were as described (Wong, G. T. et al., *Nature*, 381: 796-800 (1996)). Slides were coated with Kodak NTB-2 nuclear track emulsion and exposed at 4° C. for 3 weeks and then developed and fixed.

Gene Expression Profiling

Single taste receptor cell RT-PCR products (5 μl) were fractionated by size on a 1.6% agarose gel and transferred onto a nylon membrane. The expression patterns of the isolated cells were determined by Southern hybridization with 3'-end cDNA probes for mouse T1R3, α-gustducin, Gγ13, PLCβ2 and G3PDH. Blots were exposed for five hours at 80° C. Total RNAs from a single circumvallate papilla and a similar-sized piece of non-gustatory epithelium were also isolated, reverse transcribed, amplified and analyzed as for the individual cells.

Immunocytochemistry

Polyclonal antisera against a hemocyanin-conjugated T1R3 peptide (T1R3-A, aa 829-843) were raised in rabbits. The PLC β2 antibody was obtained from Santa-Cruz Biotechnologies. Ten micron thick frozen sections of human lingual tissue (previously fixed in 4% paraformaldehyde and cryoprotected in 20% sucrose) were blocked in 3% BSA, 0.3% Triton X-100, 2% goat serum and 0.1% Na Azide in PBS for 1 hour at room temperature and then incubated for 8 hours at 4° C. with purified antibody against α-gustducin, or antiserum against T1R3 (1:800). The secondary antibodies were Cy3-conjugated goat-anti-rabbit Ig for T1R3 and fluorescein-conjugated goat-anti-rabbit Ig for PLC β2. PLC β2 and T1R3 immunoreactivities were blocked by preincubation of the antisera with the corresponding synthetic peptides at 10 μm and 20 μM, respectively. Preimmune serum did not show any immunoreactivity. Some sections were double-immunostained with T1R3 and PLC β2 antisera as described (Bakre, M. M. et al., submitted (2001)). Briefly, sections were incubated sequentially with T1R3 antiserum, anti-rabbit-Ig Cy3 conjugate, normal anti-rabbit-Ig, PLCβ2 antibody and finally with anti-rabbit-Ig-FITC conjugate with intermittent washes between each step. Control sections that were incubated with all of the above except PLC 2 antibody did not show any fluorescence in the green channel.

Identification of Sequence Polymorphisms in mT1R3

Based on the sequence of mouse T1R3 obtained from the Celera mouse fragments database, oligonucleotide primers were designed to amplify DNA encoding regions with open reading frames. Total RNA isolated from taste papillae or tail genomic DNA isolated from one taster (C57BL/6J) and one non-taster (129/Svev) mouse strain each were used as templates to amplify mouse T1R3 cDNA and genomic DNA using RT-PCR and PCR, respectively. PCR products were sequenced completely in an ABI 310 automated sequencer. Based on the sequence obtained, four sets of oligonucleotide primers were used to amplify the T1R3 regions where polymorphisms were found between the two strains of mice. Genomic DNA from mouse strains DBA/2, BALB/c, C3H/HeJ, SWR and FVB/N, was used as template. The amplicons were purified and directly sequenced. The genealogical tree of these strains of mice was based on Hogan et al., *Manipulating the mouse embryo: a laboratory manual* (Cold Spring Harbor Laboratory, Cold Spring Harbor, 1994)) and the Jackson laboratory web site (http://www.jax.org).

Modeling the Structure of T1R3

The amino terminal domains (ATDs) of mouse T1R3 and mouse GluR1 were aligned using the ClustalW program (Thompson, J. D. et al., *Nucleic Acids Res.*, 22: 4673-4680 (1994)). The alignment was manually edited to generate an optimal alignment based on structural and functional considerations. Atomic coordinates of the mGluR1 ATD crystal structure (Kunishima, N. et al., *Nature*, 407: 971-977 (2000)) were obtained from the protein database and were used along with the alignment as the source of spatial restraints for modeling. The structural model of mouse T1R3 was generated using the program MODELLER (Sali, A. and Blundell, T. L., *J. Mol. Biol.*, 234: 779-815 (1993)). The original images for FIG. 7 were created using the programs Insight II and Weblab Viewer (Molecular Simulations Inc.) and then imported into Photoshop where the open view was created and the labels were added.

Results

Mapping of the Murine and Human Sac Regions

The murine Sac gene is the primary determinant of interstrain preference responses to sucrose, saccharin, acesulfame, dulcin, glycine and other sweeteners (Fuller, J. L., *J. Hered.*, 65: 33-36 (1974); Lush, I. E., *Genet. Res.*, 53: 95-99 (1989); Capeless, C. G. and Whitney, G., *Chem Senses*, 20: 291-298 (1995); Lush, I. E. et al., *Genet Res.*, 66: 167-174 (1995)), however, the molecular nature of the Sac gene product is unknown. Taster vs. non-taster strains of mice display differences in the electrophysiological responses of their taste nerves to sweeteners and sweet amino acids, arguing that Sac exerts its effect on the sweet pathway at the periphery (Bachmanov, A. A. et al., *Mammal Genome*, 8: 545-548 (1977)); Frank, M. E. and Blizard, D. A., *Physiol Behav.*, 67: 287-297 (1999). The most likely explanation for these differences is an allelic difference in a gene encoding a sweet-responsive taste transduction element such as a receptor, G protein subunit, effector enzyme or other member of the sweet signaling pathway. It had been speculated that the Sac gene product modified a sweet responsive receptor (Lush, I. E. et al., *Genet. Res.*, 66: 167-174 (1995)), was itself a taste receptor (Hoon, M. A. et al., *Cell*, 96: 541-551 (1999)) or a G protein subunit (Bachmanov, A. A. et al., *Mammal Genome*, 8: 545-548 (1977)). As a first step toward identifying the nature of the Sac gene we generated a contiguous map of the human genome in this region was generated. Starting with the mouse marker D18346 (Li, X. et al., *Genome*, 12: 13-16 (2001)), which maps most closely to the sac locus at 4pter, a novel mouse gene from the est database was identified: D18346 is found in the 3' untranslated region (UTR) of a novel mouse gene with homology to pseudouridine synthase. At the time this work was initiated the sequence of the human genome was nearly complete (although only partially assembled), while that of mouse was quite incomplete, hence, finished human genomic sequences and unfinished sequences from bacterial artificial chromosome (BAC) and PI artificial chromosome (PAC) clones known to map to human chromosome lpter-lp36.33 (syntenic to mouse 4pter) was screened for the ortholog of the novel pseudouridine synthase-like gene containing the D18346 marker. Using the TblastN program the high-throughput human genomic sequence (HTGS) database (NCBI) was searched to identify a PAC clone containing the human ortholog of the pseudouridine synthase-like gene. By repeated Blast searches of the human HTGS with portions of the sequence from this and overlapping PAC and BAC clones we were able to form a contiguous map ("contig") of 6 overlapping BAC or PAC clones spanning approximately one million bp of human genomic DNA sequence was found.

Using the Genscan gene prediction program we identified the predicted exons and genes within this contig were identified. Twenty three genes were predicted in this region (FIG. 1A), including "pseudouridine synthase-like", "cleavage and polyadenylation-like", and "glycolipid transfer-like"; a few genes within this region had been previously identified and/or experimentally verified by others (e.g. disheveled 1, dvll). The Celera mouse genomic database was searched to identify the murine orthologs of the genes within this region and pieced together the mouse contig (FIG. 1A).

Identification of a Novel Receptor, T1R3, within the Sac Region

In the screen of the million bp of genomic DNA sequence in the Sac region, only one predicted GPCR gene was found. The gene, which was referred to as T1R3 (for taste receptor one, member three family), was of special interest because the predicted protein it encodes is most similar to T1R1 and T1R2, two orphan GPCRs expressed in taste cells (Hoon, M. A. et al., *Cell,* 96: 541-551 (1999)), and because, as will be shown below, it is expressed specifically in taste cells. Human T1R3 (hT1R3) is located about 20 kb from the pseudouridine synthase-like gene, the human ortholog of the mouse gene containing the D18346 marker (FIG. 1A). If T1R3 is Sac, then its proximity to D18346 is consistent with the previously observed very low probability of crossovers between the marker and the Sac locus in F2 crosses and congenic mice (Li, X. et al., *Genome,* 12: 13-16 (2001)).

Figure 1C:
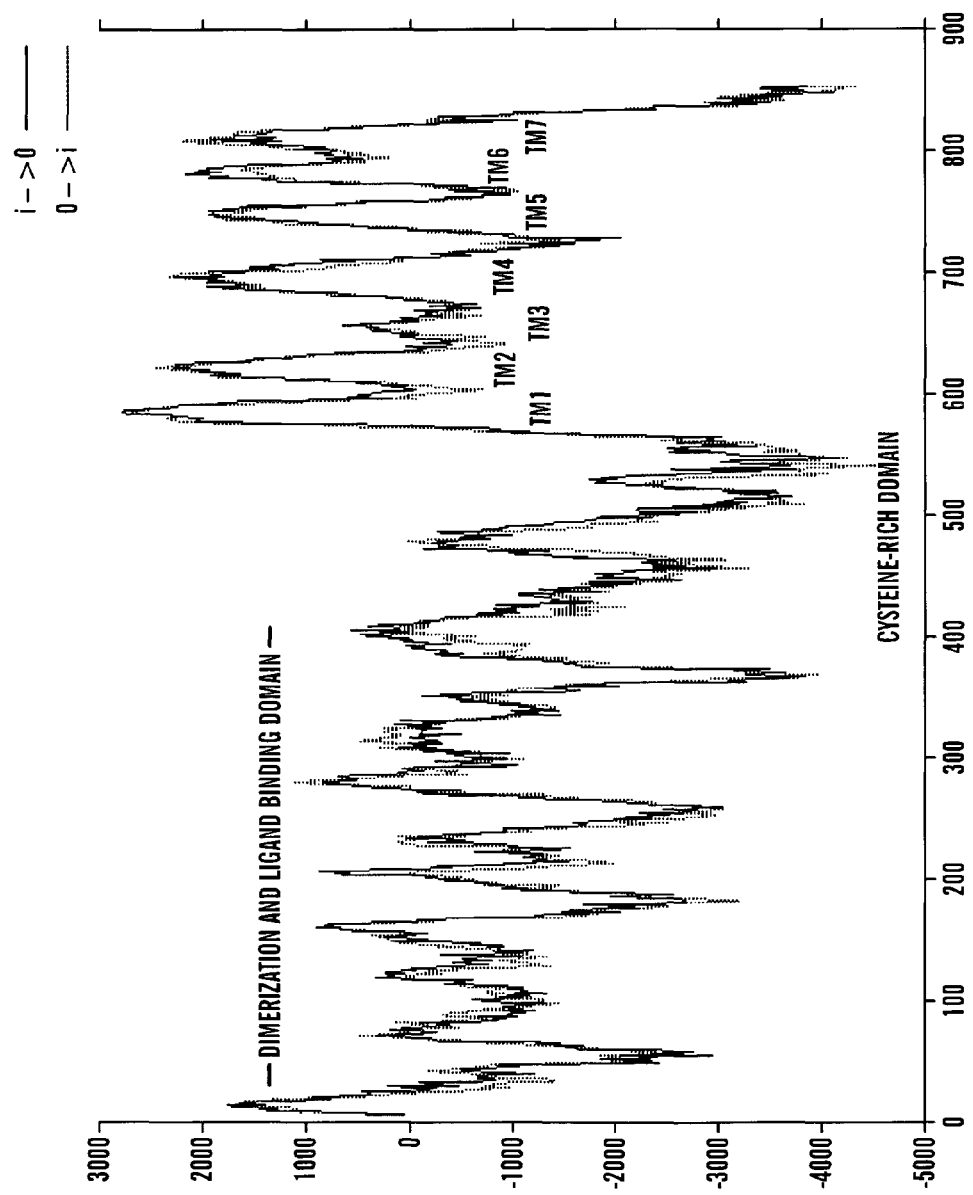
FIG. 1C. Predicted secondary structure of human T1R3. T1R3 is predicted to have seven transmembrane helices and a large N-terminal domain. Placement of the transmembrane segments was according to the TMpred program. Placement of the dimerization and ligand binding domain, and the cysteine-rich domain were based on the mGluRl receptor and other family 3 GPCRs (Kunishima, N. et al., Nature 407: 971-977 (2000)).

The intron/exon structure of the coding portion of the hT1R3 gene was predicted by Genscan to span 4 kb and contain 7 exons (FIG. 1B). To confirm and refine the inferred amino acid sequence of the predicted hT1R3 protein we cloned and sequenced multiple independent products from polymerase chain reaction (PCR) amplified hT1R3 cDNAs derived from a human tastecDNA library. Based on the nucleotide sequence of the genomic DNA and cDNAs, the hydrophobicity profile and TMpred predictions of membrane spanning regions (FIG. 1C), hT1R3 is predicted to encode a protein of 843 amino acids with seven transmembrane helices and a large 558 amino acid long extracellular domain.

Figure 5B:
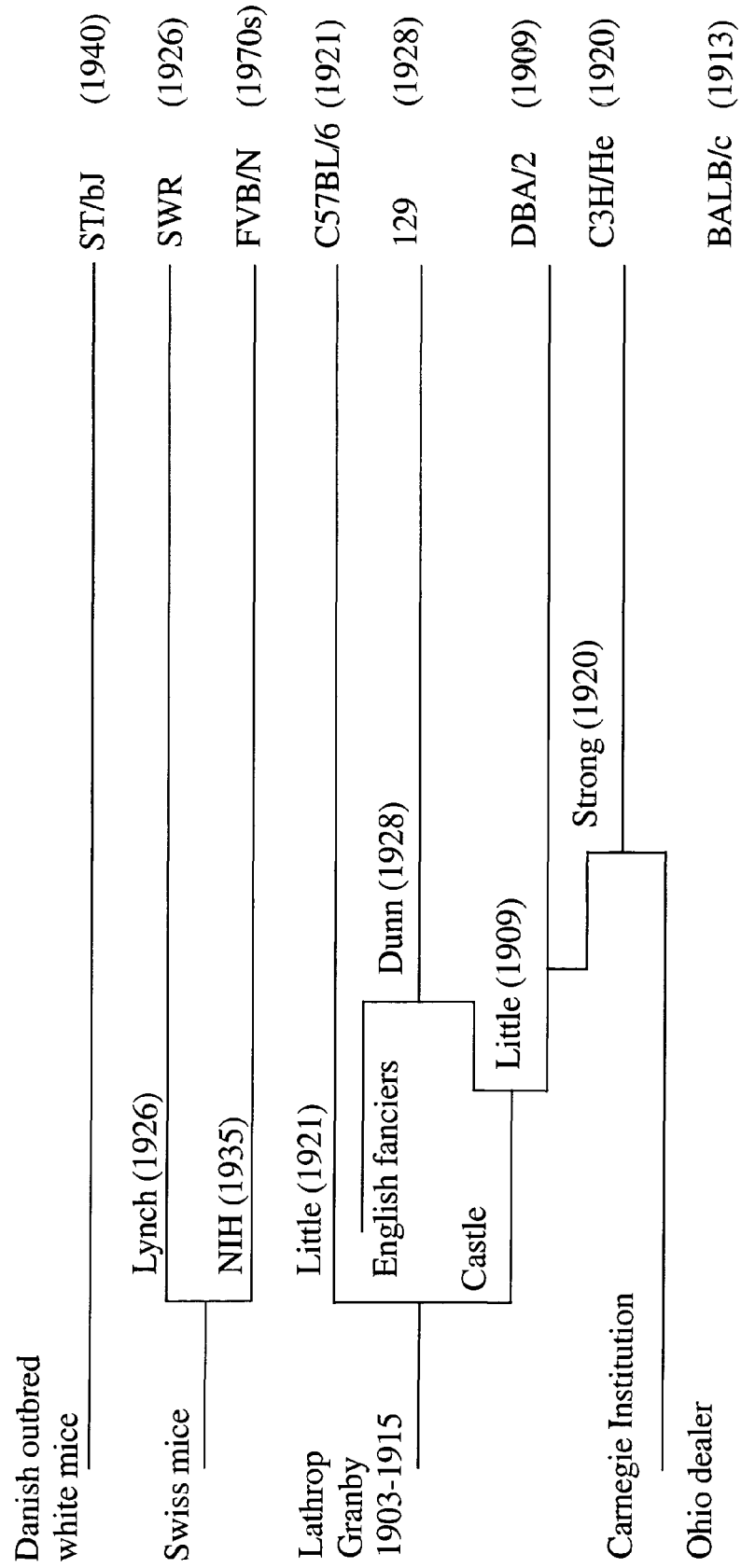
FIG. 5B. Genealogy of the inbred strains of mice analyzed in FIG. 5A. The year in which the strains were developed is indicated between brackets following the stain name. The laboratories in which these mice were established are indicated.

The corresponding mouse T1R3 (mT1R3) genomic sequence was assembled from the Celera mouse genomic fragment database. Several reverse transcriptase (RT)-PCR-generated mouse T1R3 cDNAs derived from taste budmRNA of different mouse strains were also cloned and sequenced. The coding portion of the mouse T1R3 gene from C57BL/6 spans 4 kb and contains 6 exons; the encoded protein is 858 amino acids long. Polymorphic differences between taster and non taster strains of mice, and their potential functional significance, are described below (see FIGS. 5 and 6 and related text).

T1R3 is a member of the family 3 subtype of GPCRs, all of which contain large extracellular domains, other family 3 subtype GPCRs include metabotropic glutamate receptors (mGluR), extracellular calcium sensing receptors (ECaSR), candidate pheromone receptors expressed in the vomeronasal organ (V2R), and two taste receptors, T1R1 and T1R2, of unknown ligand specificity. T1R3 is most closely related to T1R1 and T1R2, sharing ~30% amino acid sequence identity with each of these orphan taste receptors (T1R1 and T1R2 are ~40% identical to each other). At the amino acid level hT1R3 is ~20% identical to mGluRs and ~23% identical to ECaSRs. The large amino terminal domain (ATD) of family 3 GPCRs has been implicated in ligand binding and dimerization (Kunishima, N. et al., *Nature,* 407: 971-977 (2000)). Like other family 3 GPCRs, mT1R3 has an amino-terminal signal sequence, an extensive ATD of 573 amino acids, multiple predicted asparagine-linked glycosylation sites (one of which is highly conserved), and several conserved cysteine residues. Nine of these cysteines are within a region that links the ATD to the portion of the receptor containing the transmembrane domains. The potential relevance of mT1R3's ATD in phenotypic differences between taster and non-taster strains of mice is elaborated below (see FIGS. 5 and 6 and related text).

Expression of T1R3 mRNA and Protein in Taste Tissue and Taste Buds

Figure 2A:
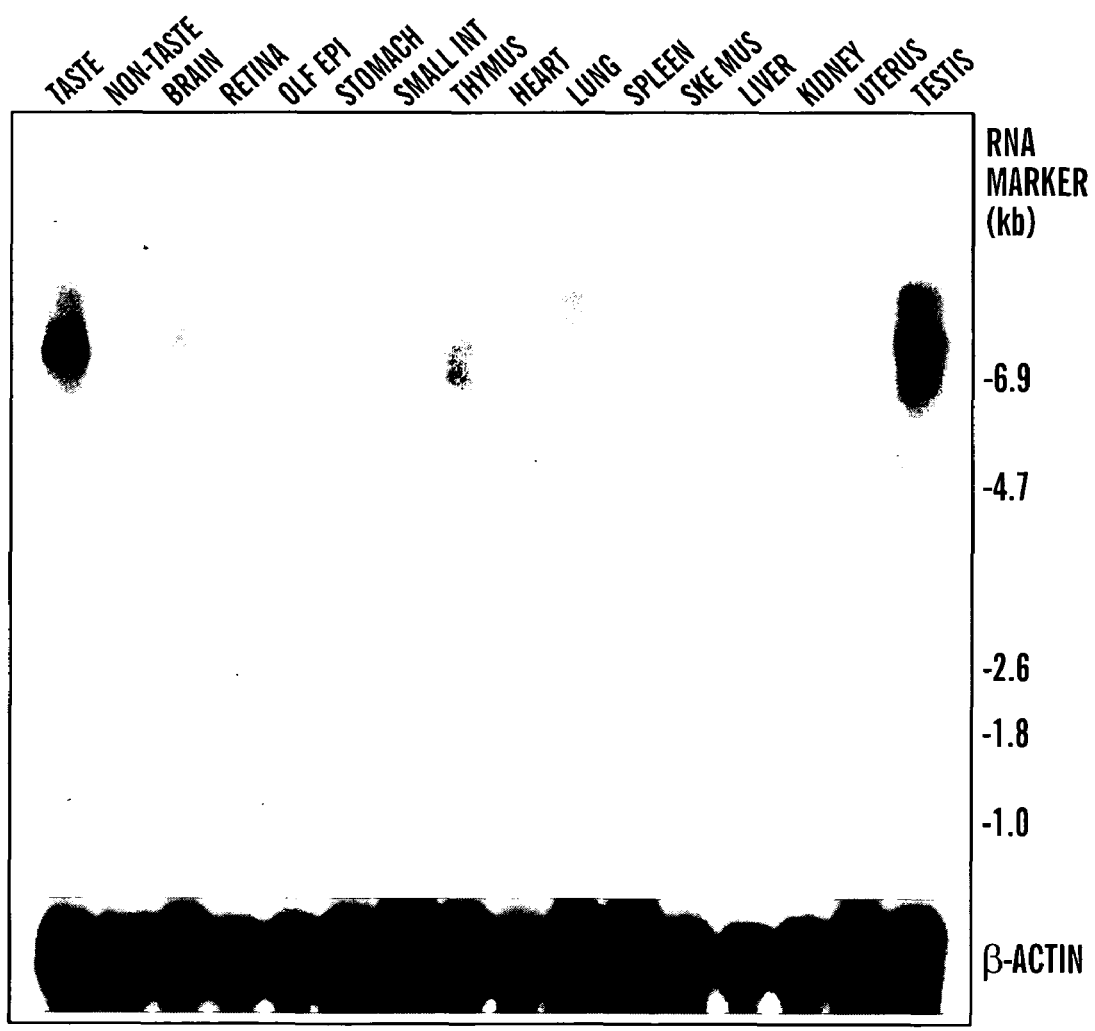
FIG. 2A. Distribution of T1R3 mRNA in mouse tissues and mouse taste cells. Autoradiogram of a Northern blot hybridized with mouse T1R3 cDNA. Each lane contained 25 µg of total RNA isolated from the following mouse tissues: circumvallate and foliate papillae-enriched lingual tissue (Taste), lingual tissue devoid of taste buds (Non-Taste), brain, retina, olfactory epithelium (Olf Epi), stomach, small intestine (Small Int), thymus, heart, lung, spleen, skeletal muscle (Ske Mus), liver, kidney, uterus and testis. A 7.2 kb transcript was detected only in the taste tissue, and a slightly larger transcript was detected in testis. The blot was exposed to X-ray film for three days. The same blot was stripped and reprobed with a β-actin cDNA (lower panel) and exposed for one day. The size of the RNA marker (in kilobases) is indicated in the right margin.

To examine the general distribution of mouse T1R3 in taste and non-taste tissues, northern blot analysis was carried out with a panel of mouse mRNAs. The mouse T1R3 probe hybridized to a 7.2 kb mRNA present in taste tissue, but not expressed in control lingual tissue devoid of taste buds (non-taste) or in any of the several other tissues examined (FIG. 2A). A somewhat larger (~7.8 kb) mRNA species was expressed at moderate levels in testis, and at very low levels in brain. A smaller (~6.7 kb) mRNA species was expressed at very low levels in thymus. The 7.2 kb taste-expressed transcript is longer than the isolated cDNAs or Genscan predicted exons, suggesting that additional untranslated sequences may be present in the transcript.

Figure 2B:
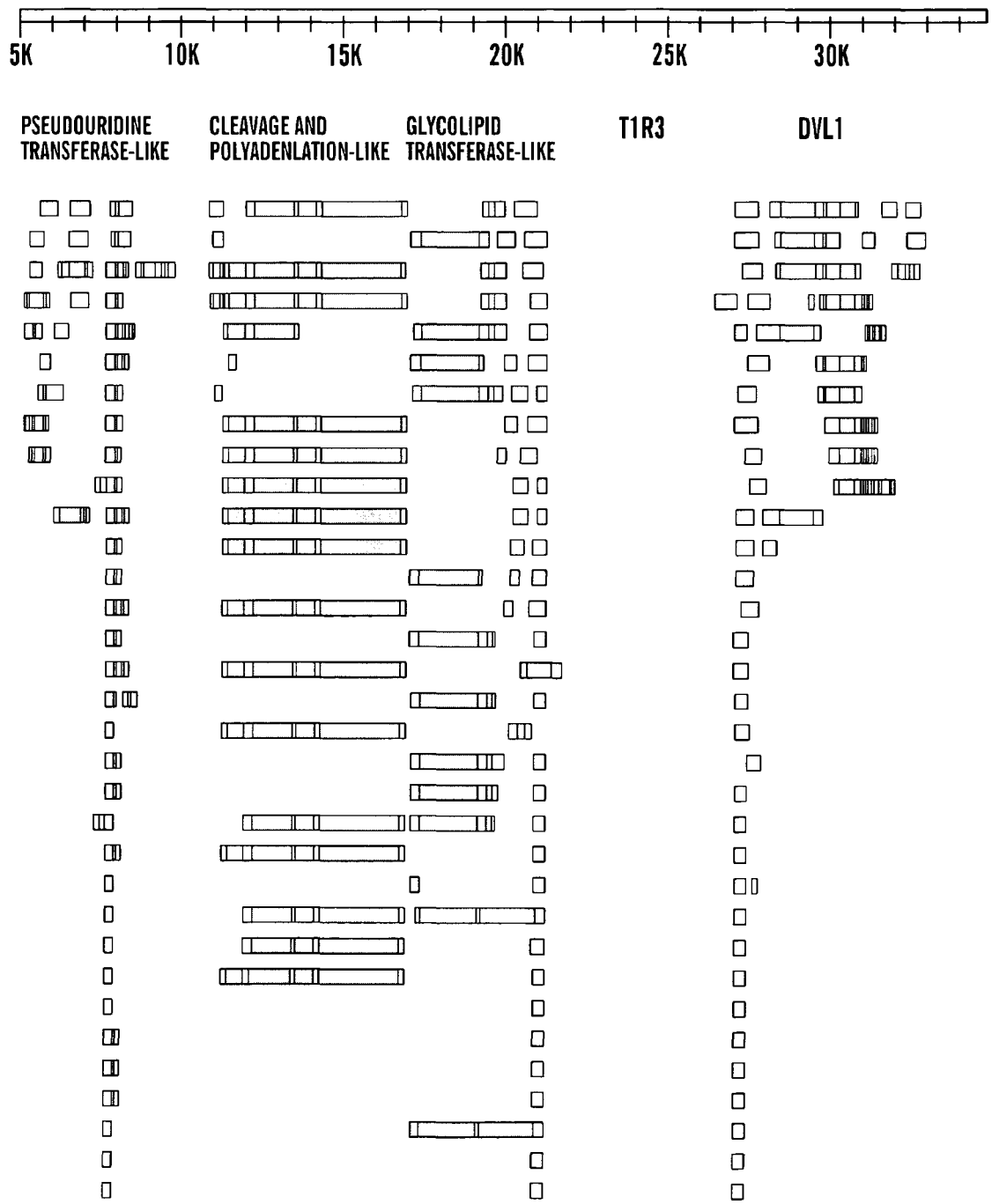
FIG. 2B. The genomic sequence of the Sac region from mouse was used as a query to search the mouse expressed sequence tag (est) database. Matches to the est database are shown in solid red and indicate exons; gaps in a particular est match are shown by black hatched lines and indicate an intron. The clustered nature of the est matches demarcates the extent of each of the genes within this region. The near absence of ests at the position of T1R3 is consistent with the highly restricted pattern of expression seen in FIG. 2A.

As another measure of the pattern of expression of T1R3 in various tissues the expressed sequence tags (est) database were examined for strong matches to T1R3 and other predicted genes in the Sac region (FIG. 2B). While dvll, glycolipid transfer-like, cleavage and polyadenylation-like, and pseudouridine synthase-like genes each had numerous highly significant matches to ests from several different tissues, T1R3 showed only a single strong match to an est from colon. This result, consistent with the northern, suggests that expression of T1R3 is highly restricted—such a pattern of under-representation in the est database would fit with T1R3 being a taste receptor.

Figure 3A:
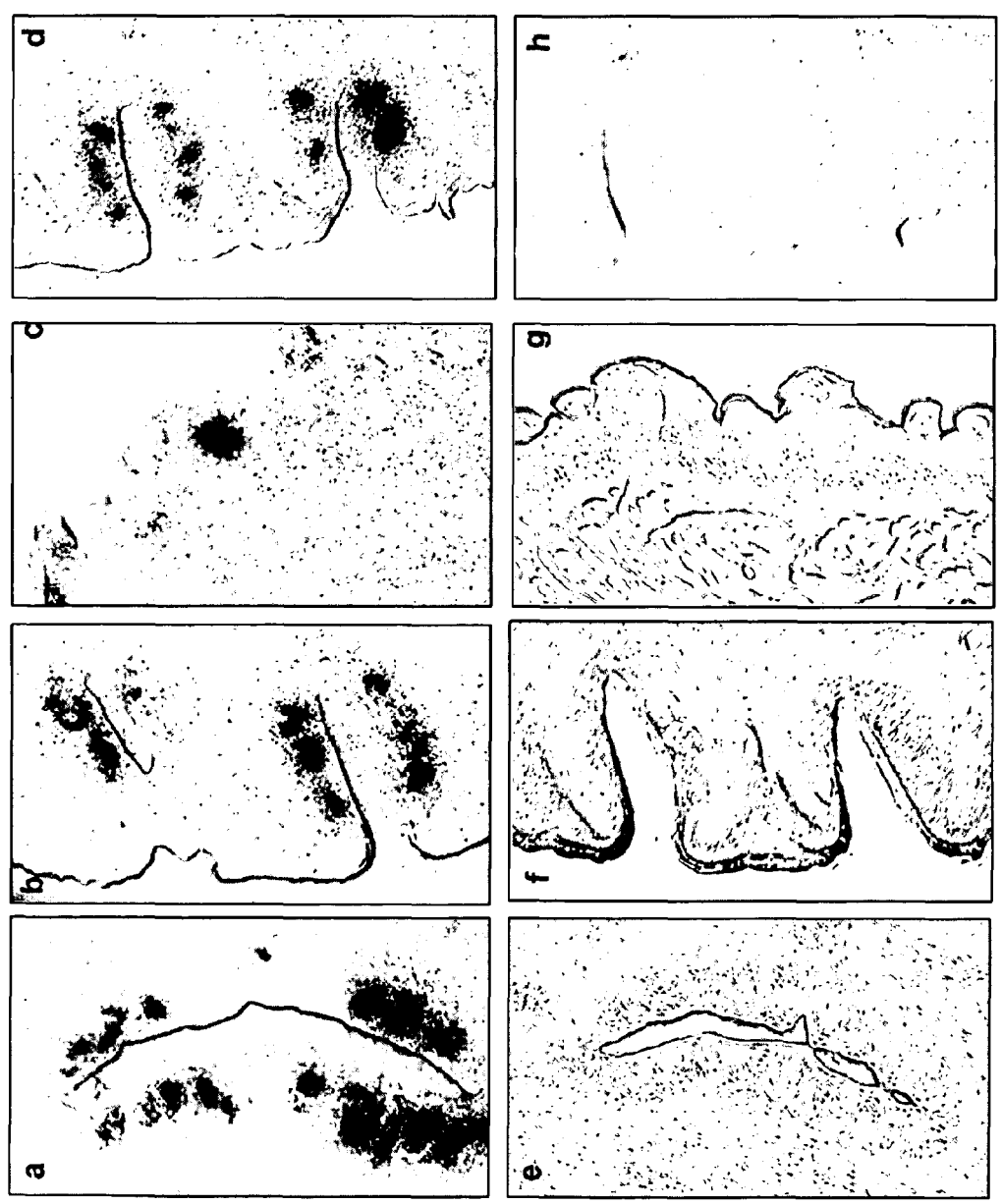
FIG. 3A. T1R3 expression in taste receptor cells. Photomicrographs of frozen sections of mouse taste papillae hybridized with $^{33}$P-labelled antisense RNA probes for T1R3 and α-gustducin. Bright-field images of circumvallate (a), foliate (b), and fungiform (c) papillae hybridized to the antisense T1R3 probe demonstrate taste bud-specific expression of T1R3. Control bright-field images of circumvallate (e), foliate (f), and fungiform papillae (g) hybridized to the sense T1R3 probe showed no nonspecific binding. The level of expression and broad distribution of T1R3 expression in taste buds was comparable to that of α-gustducin as shown in the bright field image of circumvallate papilla hybridized to antisense α-gustducin probe (d). The control bright field image of circumvallate papilla hybridized to the sense α-gustducin probe (h) showed no nonspecific binding.

To determine the cellular pattern of T1R3 expression in taste tissue, in situ hybridization was performed: T1R3 was selectively expressed in taste receptor cells, but absent from the surrounding lingual epithelium, muscle or connective tissue (FIG. 3A). Sense probe controls showed no non-specific hybridization to lingual tissue (FIG. 3A). The RNA hybridization signal for T1R3 was even stronger than that for α-gustducin (FIG. 3A), suggesting that T1R3 mRNA is very highly expressed in taste receptor cells. This is in contrast to results with T1R1 and T1R2 mRNAs, which are apparently expressed at lower levels than is α-gustducin (Hoon, M. A. et al., *Cell*, 96: 541-551 (1999)). Furthermore, T1R3 is highly expressed in taste buds from fungiform, foliate and circumvallate papillae, whereas T1R1 and T1R2 mRNAs each show different regionally variable patterns of expression (T1R1 is preferentially expressed in taste cells of the fungiform papillae and qeschmacksstreifen ('taste stripe'), to a lesser extent in those of the foliate papillae, but rarely in those of the circumvallate papillae; T1R2 is commonly expressed in taste cells of the circumvallate and foliate papillae, but rarely in those of the fungiform papillae or geschmacksstreifen) (Hoon, M. A. et al., *Cell*, 96: 541-551 (1999)).

Figure 3B:
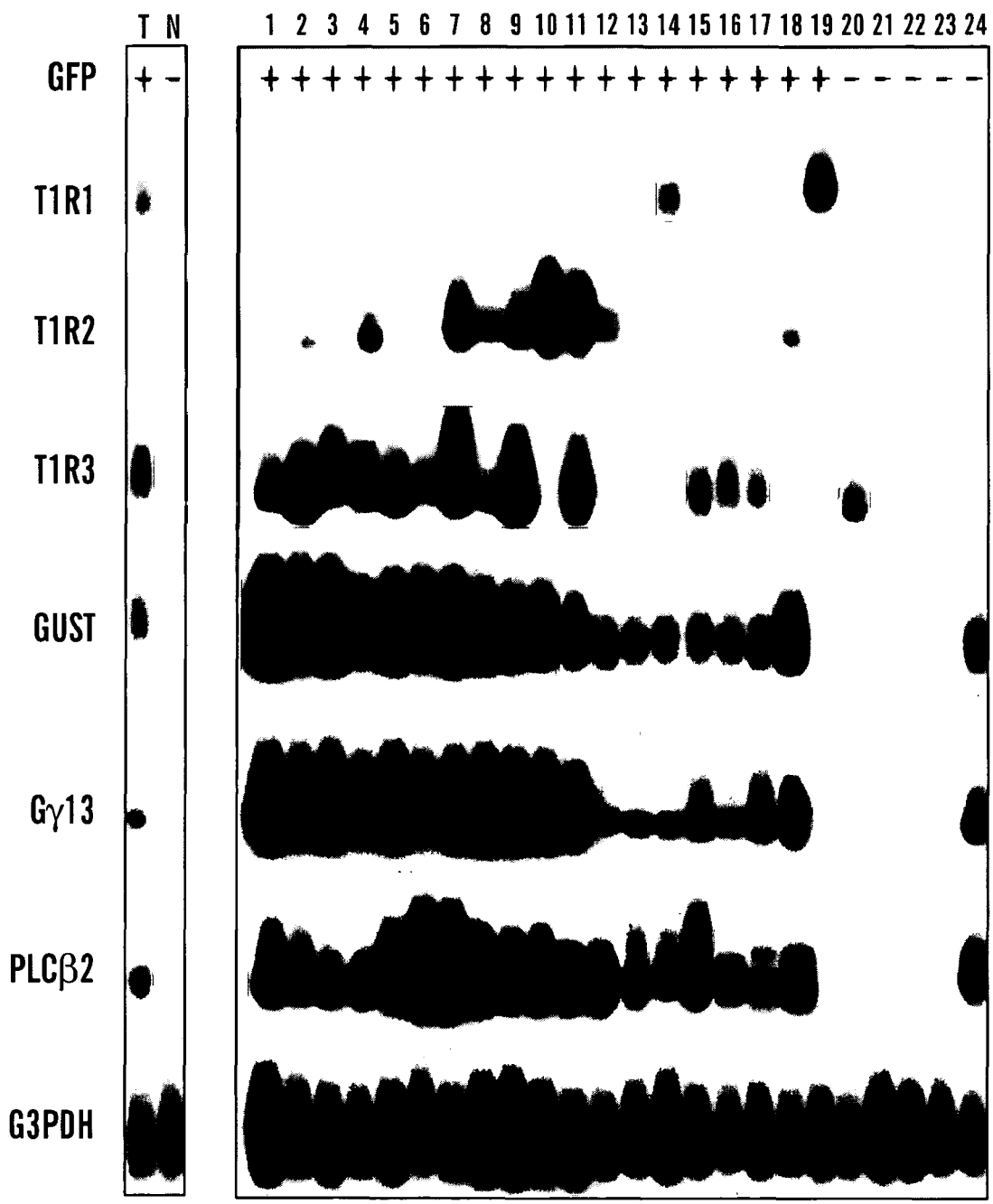
FIG. 3B. Profiling the pattern of expression of T1R3, α-gustducin, Gγ13 and PLCβ2 in taste tissue and taste cells. Left panel: Southern hybridization to RT-PCR products from murine taste tissue (T) and control non-taste lingual tissue (N). 3'-region probes from T1R3, α-gustducin (Gust), Gγ13, PLCβ2 and glyceraldehyde 3-phosphate dehydrogenase (G3PDH) were used to probe the blots. Note that T1R3, α-gustducin, Gγ13 and PLCβ2 were all expressed in taste tissue, but not in non-taste tissue. Right panel: Southern hybridization to RT-PCR products from 24 individually amplified taste receptor cells. 19 cells were GFP-positive (+), 5 cells were GFP-negative (−). Expression of α-gustducin, Gγ13 and PLCβ2 was fully coincident. Expression of T1R3 overlapped partially with that of α-gustducin, Gγ13 and PLCβ2. G3PDH served as a positive control to demonstrate successful amplification of products.

To determine if T1R3 mRNA is expressed in particular subsets of taste receptor cells, expression profiling was used (Huang, L. et al., *Nat Neurosci*, 2: 1055-1062 (1999)). First, probes from the 3' regions of mouse clones for T1R3, α-gustducin, Gγ13, PLCβ2 and G3 PDH cDNAs were hybridized to RT-PCR-amplified cDNAs from a single circumvallate papilla vs. a similar-sized piece of non-gustatory lingual epithelium. In this way it was determined that mouse T1R3, like α-gustducin, Gγ13 and PLCβ2, was expressed in taste bud-containing tissue, but not in non-gustatory lingual epithelia (FIG. 3B left). The pattern of expression of these genes in individual taste cells was next profiled: the single cell RT-PCR products were hybridized with the same set of probes used above. As previously determined (Huang, L. et al., *Nat Neurosci*, 2: 1055-1062 (1999)), all of the nineteen α-gustducin-positive cells expressed Gβ3 and Gγ13; these nineteen cells also all expressed PLCβ2 (FIG. 3B right). Twelve of these nineteen cells (63%) also expressed T1R3. Only one of the five cells that were α-gustducin/Gβ3/Gγ13/PLCβ2-negative expressed T1R3. From this it was concluded that expression of T1R3 and α-gustducin/Gβ3/Gγ13/PLCβ2, although not fully coincident, overlaps to a great extent. This contrasts with previous in situ hybridization results with taste receptor cells of the foliate papillae in which ~15% of α-gustducin-positive cells were positive for T1R1 or T1R2 (Hoon, M. A. et al., *Cell*, 96: 541-551 (1999)).

Figure 4:
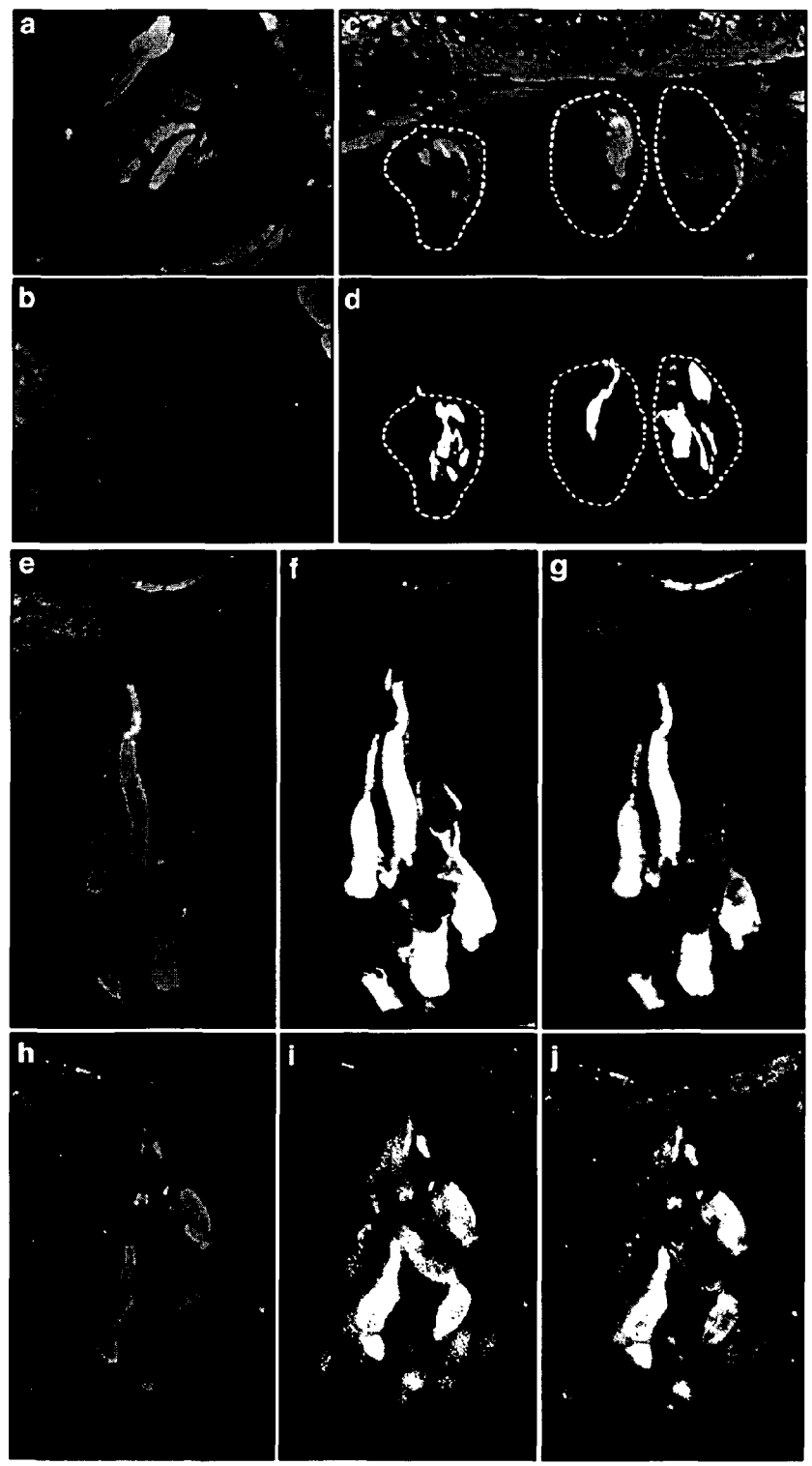
FIG. 4. Co-localization of T1R3, PLCβ2 and α-gustducin in taste receptor cells of human circumvallate papillae. (a, c) Longitudinal sections from human circumvallate papillae were labeled with rabbit antisera directed against a C-terminal peptide of human T1R3, along with a Cy3-conjugated anti-rabbit secondary antibody. (b) T1R3 immunoreactivity in longitudinal sections from human papillae was blocked by pre-incubation of the T1R3 antibody with the cognate peptide. (d) A longitudinal section adjacent to that in sections of human fungiform papillae double immunostained for T1R3 (h) and α-gustducin (i). The overlay of the two images is shown in (j). Magnification was 200× (a-d) or 400× (e-j).

Immunocytochemistry with an anti-hT1R3 antibody demonstrated that about one fifth of taste receptor cells in human circumvallate (FIG. 4AC) and fungiform (FIG. 4EH) papillae were positive for hTIR3. hTIR3 immunoreactivity was blocked by pre-incubation of the hTIR3 antibody with the cognate peptide (FIG. 4B). Longitudinal sections of the hTIR3-positive taste cells displayed an elongated bipolar morphology typical of so called light cells (many of which are α-gustducin-positive), with the immunoreactivity most prominent at or near the taste pore (FIG. 4ACEH). Labeling adjacent sections with antibodies directed against hTIR3 and PLCβ2 showed more cells positive for PLCβ2 than for hT1R3 (FIG. 4CD). Double labeling for hT1R3 and PLCβ2 (FIG. 4EFG), or for hT1R3 and α-gustducin (FIG. 4HIJ) showed many, but not all, cells to be doubly positive (more cells were positive for PLCβ2 or α-gustducin than for hT1R3), consistent with the results from expression profiling. In sum, T1R3 mRNA and protein are selectively expressed in a subset of α-gustducin/PLCβ2-positive taste receptor cells as would be expected for a taste receptor.

A Single Polymorphic Difference in T1R3 may Explain the SAC$^d$ Non-Taster Phenotype C57BL/6 mice carrying the Sac$^b$ allele and other so called taster strains of mice display enhanced preferences and larger chorda tympani nerve responses vs. DBA/2 mice (sac$^d$) and other non-taster strains for several compounds that humans characterize as sweet (e.g. sucrose, saccharin, acesulfame, dulcin and glycine) (Lush, I. E. *Genet. Res.*, 53: 95-99 (1989); Capeless, C. G. and Whitney, G., *Chem Senses*, 20: 291-298 (1995); Lush, I. E. et al., *Genet Res.*, 66: 167-174 (1995); Bachmanov, A. A. et al., *Mammal Genome*, 8: 545-548 (1977); Blizzard, D. A. et al., *Chem Senses*, 24: 373-385 (1999); Frank, M. E. and Blizard, D. A., *Physiol Behav.*, 67: 287-297 (1999)). The inferred amino acid sequence of T1R3 from taster and nontaster strains of mice were examined looking for changes that might explain these phenotypic differences (see FIG. 5A). All four non-taster strains (DBA/2, 129/Svev, BALB/c and C3H/HeJ) examined had identical nucleotide sequences despite the fact that their most recent common ancestors date back to the early 1900s or earlier (see FIG. 5B).

All four taster strains (C57BL/6J, SWR, FVB/N and ST/bj) shared four nucleotide differences vs. the non-tasters: $nt_{135}$A-G, $nt_{163}$ A-G, $nt_{179}$ T-C and $nt_{652}$ T-C (the taster nt is listed first). C57BL/6J also had a number of positions at which it differed from all other strains (see FIG. 5A); however, many of these differences were either "silent" alternate codon changes in protein coding regions or substitutions within introns where they would be unlikely to have any pronounced effect. The two coding changes (described as single letter amino acid changes at specific residues; the taster aa is listed first) were T55A and I60T. The I60T change is a particularly intriguing difference as it is predicted to introduce a novel N-linked glycosylation site in the ATD of T1R3 (see below).

Figure 7A:
FIG. 7. The predicted three dimensional structure of the amino-terminal domain (ATD) of T1R3 modeled on that of mGluRl (19) using the Modeller program. The model shows a homodimer of T1R3. (a) The view from the "top" of the dimer looking down from the extracellular space toward the membrane. (b) The T1R3 dimer viewed from the side. In this view the transmembrane region (not displayed) would attach to the bottom of the dimer. (c) The T1R3 dimer is viewed from the side as in (b), except the two dimers have been spread apart (indicated by the double headed arrow) to reveal the contact surface. A space-filling representation (colored red) of three glycosyl moieties (N-acetylgalactose-N-acetyl-galactose-Mannose) has been added at the novel predicted site of glycosylation of non-taster mT1R3. Note that the addition of even three sugar moieties at this site is sterically incompatible with dimerization. Regions of T1R3 corresponding to those of mGluR1 involved in dimerization are shown by space filling amino acids. The four different segments that form the predicted dimerization surface are color-coded in the same way as are the dashed boxes in FIG. 5. The portions of the two molecules outside of the dimerization region are represented by a backbone tracing. The two polymorphic amino acid residues of T1R3 that differ in taster vs. nontaster strains of mice are within the predicted dimerization interface nearest the amino terminus (colored light blue). The additional N-glycosylation site at aa58 unique to the non-taster form of T1R3 is indicated in each panel by the straight arrows.
Figure 7B:
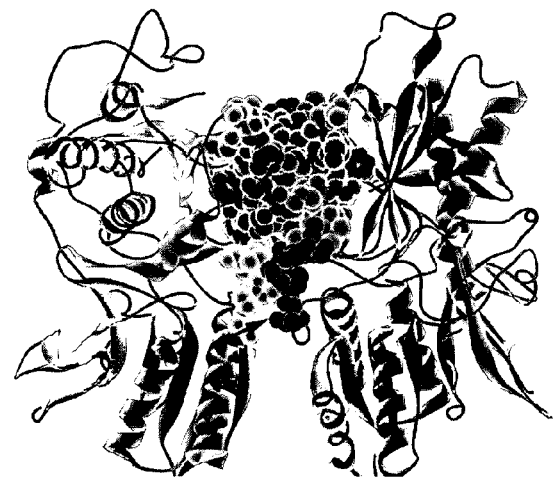

To consider the functional relevance of these two amino acid differences in the T1R3 proteins from taster vs. nontaster, the ATD of T1R3 (SEQ ID NO: 3) was aligned with those of other members of the type 3 subset of GPCRs (FIG. 6) and the ATD of T1R3 was modeled based on the recently solved structure of the ATD of the related mGluR1 receptor (Kunishima, N. et al., *Nature*, 407:971-977 (2000)) (FIG. 7). The ATD of T1R3 displays 28, 30, 24, and 20% identity to those of T1R1 (SEQ ID NO: 4), T1R2 (SEQ ID NO: 5), CaSR (SEQ ID NO: 6) and mGluR1 (SEQ ID NO: 7), respectively (FIG. 6). 55 residues of ~570 in the ATD were identical among all five receptors. Included among these conserved residues is a predicted N-linked glycosylation site at N85 of T1R3. Based on homology to mGluR1, regions predicted to be involved in dimerization of T1R3 are aa 55-60, 107-118, 152-160, and 178-181 (shown in FIG. 6 within dashed boxes). The I60T taster to non-taster substitution is predicted to introduce a novel N-linked glycosylation site 27 amino acids upstream from the conserved N-linked glycosylation site present in all five receptors. The new N-linked glycosylation site at N58 might interfere with normal glycosylation of the conserved site at N85, alter the structure of the ligand binding domain, interfere with potential dimerization of the receptor, or have some other effect on T1R3 function.

Figure 7C:
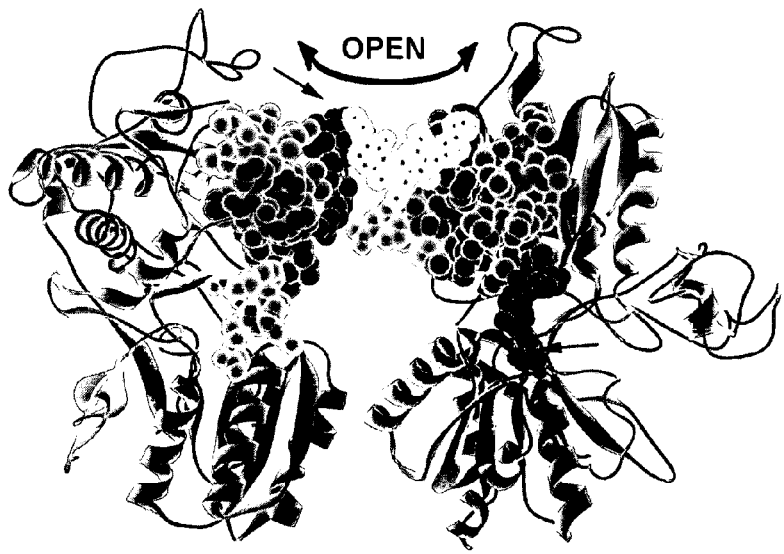

To determine if glycosylation at N58 of the nontaster variant of mT1R3 might be expected to alter the function of the protein we modeled its ATD on that of mGluR1 (Kunishima, N. et al., *Nature*, 407: 971-977 (2000)) (FIG. 7). The regions of potential dimerization in T1R3 are very similar to those of mGluR1 and the amino acids in these regions form tight fitting contact surfaces that suggest that dimerization is indeed likely in T1R3. From the model of the three dimensional structure of the ATD of T1R3 we can see that the novel N-linked glycosylation site at N58 would have a profound effect on T1R3's ability to dimerize (FIG. 7C). The addition of even a short carbohydrate group at N58 (a trisaccharide moiety has been added in the model in FIG. 7C) would disrupt at least one of the contact surfaces required for stability of the dimer. Therefore, if T1R3, like mGluR1, adopts a dimeric form (either homodimer or heterodimer), then the predicted N-linked glycosyl group at N58 would be expected to preclude T1R3 from forming self-homodimers or heterodimers with any other GPCRs co-expressed with T1R3 using the same dimerization interface. Even if the novel predicted glycosylation site at N58 of non-taster T1R3 is not utilized, the T55A and I60T substitutions at the predicted surface of dimerization may themselves affect the ability of T1R3 to form dimers.

Example 2

Method Used to Produce Transgenic Mice

Figure 10:
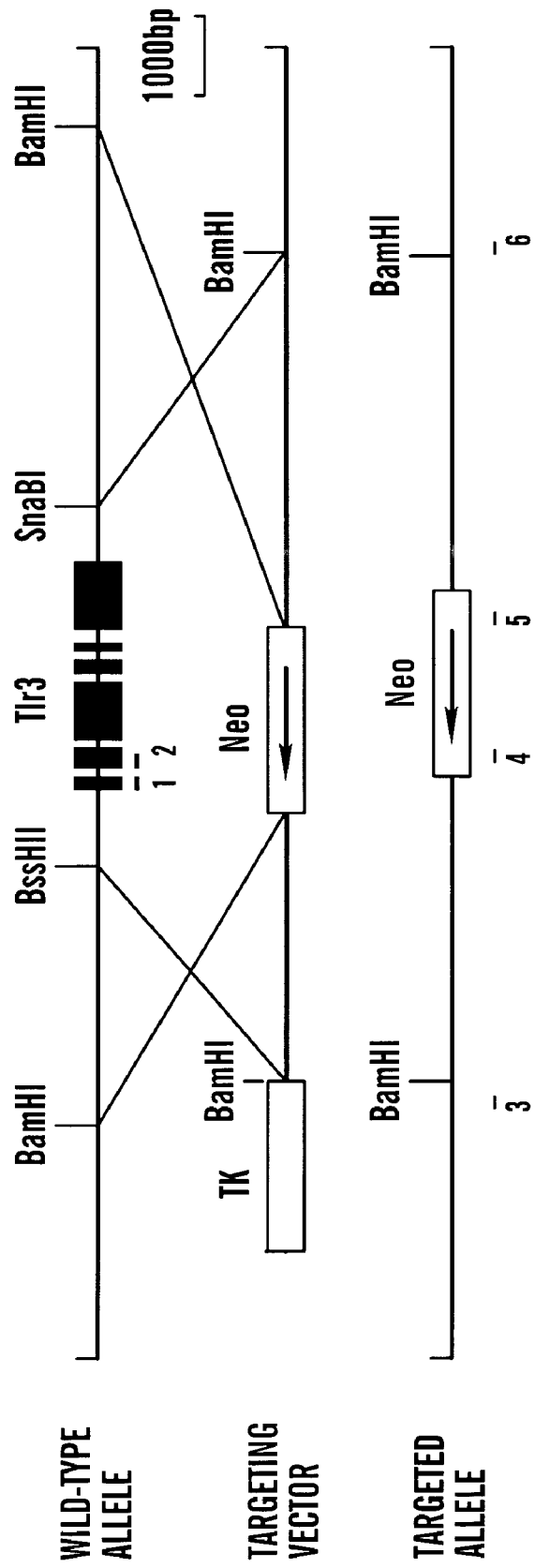
FIG. 10. Generation of T1R3 knock-out mice. Top: A map of the murine T1R3 locus showing the six exons (filled boxes) and intervening and flanking sequences. The polymerase chain reaction (PCR) primers that were used to detect the wild-type (WT) T1R3 allele are indicated by the numbered short lines below the map. Middle: A map of the targeting vector showing PGKneo (Neo) and PGKTK (TK) genes (open boxes) and the long and short arms of the targeting vector. Neo was flanked with LoxP sites for removal of neo by Cre recombinase. The arrow indicates the direction of transcription of neo. The targeting vector was designed to remove the entire T1R3 coding region. Bottom: A diagram of the T1R3 targeted allele. The primers that were used to screen the G418-resistant ES colonies are indicated by numbered short lines below the map.

Knock-out mice lacking the entire T1R3 coding region were produced by homologous recombination in C57BL6 (B6) embryonic stem (ES) cells, followed by injection of the targeted stem cells into blastocysts (see FIG. 10).

A B6 mouse BAC library was screened with a PCR-amplified T1R3 DNA probe having the following nucleotide sequence (SEQ ID NO: 10):

```
      A CAGCAATTCA AGGCACAAGG GGACTACATA CTGGGCGGGC
TATTTCCCCT GGGCTCAACC GAGGAGGCCA CTCTCAACCA GAGAACACAA
CCCAACAGCA TCCCGTGCAA CAGGTATGGA GGCTAGTAGC TGGGGTGGGA
GTGAACCGAA GCTTGGCAGC TTTGGCTCCG TGGTACTACC AATCTGGGAA
GAGGTGGTGA TCAGTTTCCA TGTGGCCTCA GGTTCTCACC CCTTGGTTTG
TTCCTGGCCA TGGCTATGAA GATGGCTGTG GAGGAGATCA ACAATGGATC
TGCCTTGCTC CCTGGGCTGC GGCTGGGCTA TGACCTATTT GACACATGCT
CCGAGCCAGT GGTCACCATG AAATCCAGTC TCATGTTCCT GGCCAAGGTG
GGCAGTCAAA GCATTGCTGC CTACTGCAAC TACACACAGT ACCAACCCCG
TGTGCTGGCT GTCATCGGCC CCCACTCATC AGAGCTTGCC CT
```

A commercial service (IncyteGenomics) performed the screen. Three BAC clones containing T1R3 were obtained and verified by PCR. A 16-kb Bam HI DNA fragment containing the T1R3 gene and flanking sequence was subcloned from a BAC clone into pBlueScript and used to make the targeting construct. The short arm of the targeting construct was 3.3 kb BamHI-BssHII fragment ending 1 kb upstream from the T1R3 ATG; the long arm was a 4.7 kb SnaBI-BamHI fragment beginning ~400 bp upstream from the T1R3 putative polyadenylation signal. These fragments were cloned into a plasmid containing PGKneo flanked by LoxP sites and PGKTK (see FIG. 10). The targeting molecule was linearized by digestion with Not I and electroporated into B6 ES cells (Lemckert, F. A. et al., *Nucleic Acids. Res.*, 25, 917 (1997)) according to standard procedures (Hogan, B. et al., Eds., *Manipulating the mouse embryo: a laboratory manual* (Cold Spring Harbor Laboratory, Cold Spring Harbor, 1994)). ES cell colonies that survived the positive/negative selection with G418 and ganciclovir were genotyped by PCR amplification of upstream T1R3 sequences and neo using primers 3 and 4 (indicated in FIG. 10), and the Expand long PCR kit (Roche Biochemicals) according to the manufacturer's instructions. The nucleotide sequence of primers 3 and 4 are provided below:

```
Primer 3 (MQ197) (SEQ ID NO: 11):
GCCAACCCACAGCCTCTGCTTTAATTTTGGGGATAC

Primer 4 (MQ162) (SEQ ID NO: 12):
GCCAAGTTCTAATTCCATCAGAAGCTGACTCTAGC
```

Homologous recombination was confirmed in positive colonies by a second long PCR amplification using primer 5 specific for the 3' end of PGKneo and primer 6 specific for a region downstream of T1R3 that is not included in the targeting vector (primers 5 and 6 are as indicated in FIG. 10). The nucleotide sequences of primers 5 and 6 are provided below:

```
Primer 5 (MQ196) (SEQ ID NO: 13):
GGCATCCTCCTTCAGCAGCATCACAGACTCC

Primer 6 (MQ164) (SEQ ID NO: 14):
GACCTGCAGGGGCCCTCGACTATAACTTCG
```

The regions corresponding to the homologous recombination sites were sequenced. No deletions or rearrangements were found.

ES cells containing a targeted T1R3 allele were microinjected into Balb/C blastocysts. Chimeras derived from these blastocysts were bred with C57BL6/J mice, and T1R3 +/− offspring were obtained. These T1R3 +/− offspring were intercrossed to generate T1R3 +/+, +/− and −/− progeny. The progeny were genotyped by PCR amplification of mouse tail DNA. PCR amplification of T1R3 exons 1 and 2 using primers 1 and 2 indicated successful disruption of the T1R3 gene in +/− and −/− progeny. The nucleotide sequences of primers 1 and 2 are provided below:

```
Primer 1 (B15F1) (SEQ ID NO: 15):
ACAGCAATTCAAGGCACAAGG

Primer 2 (B15R3) (SEQ ID NO: 16):
GAGGGCAAGCTCTGATGAGTG
```

PCR amplification of an upstream T1R3 sequence and neo using primers 3 and 4 indicated successful targeting.

Behavioral responses of T1R3 +/+ and T1R3 +/− mice were indistinguishable; therefore the T1R3 +/+ and T1R3 +/− datasets were pooled and referred to as wild-type B6 mice. T1R3 +/− mice were bred with T1R3 +/− mice and T1R3 −/− mice to generate mice for behavior and nerve recording studies. Both male and female T1R3 +/+, +/− and −/− progeny were used for these studies. The T1R3 knock-out mice were healthy and fertile with no obvious anatomical or behavioral abnormalities.

Immunohistochemistry of frozen sections of taste-bud-containing circumvallate papillae from wild-type and T1R3 knock-out mice was performed using known methods (He, W. et al., *Chem. Senses*, 27: 719 (2002)). The frozen sections were stained with T1R3-specific antibodies. The primary antibody was a rabbit polyclonal antiserum raised against a synthetic peptide corresponding to mouse T1R3 residues 239-254; the secondary antibody was a Cy3-conjugated goat anti-rabbit IgG. T1R3 knock-out mice were devoid of T1R3 protein as demonstrated by indirect immunofluorescence.

Using digoxigenin (DIG)-labeled T1R1 and T1R2 riboprobes, in situ hybridization was carried out on frozen sections of taste-bud-containing circumvallate papillae from wild-type and T1R3 knock-out mice according to known methods (Schaeren-Wiemers, N. and Gerfin-Moser, A., *Histochemistry*, 100:431 (1993)). Detection was with an alkaline phosphatase-conjugated anti-DIG antibody in the presence of nitroblue tetrazolium (NBT) and 5-bromo-4-chloro-3-indolyl phosphate (BCIP). The gross anatomy of the taste tissue and number of taste buds appeared normal in the T1R3 knock-out mice. Knocking out the T1R3 gene did not alter expression of T1R1 or T1R2.

Example 3

Characterization of T1R3 Knock-Out and Wild-Type Mice Using Behavioral Tests

Behavioral tests were conducted to examine the responses of T1R3 knock-out mice to tastants representing five taste qualities (sweet, bitter, salty, sour and umami). Mice of both sexes aged between 2 and 12 months were used. Age- and gender-matched mice were used in the three genotype groups, and littermates were used in the knock-out and B6 wild-type control groups. The two-bottle preference test consisted of giving the mice two bottles, one containing deionized water and the other a tastant solution, for 48 hours. The bottle positions were swapped after 24 hours to eliminate position effects. The ratio of tastant to total liquid consumed was measured and compared between groups using known methods (see, e.g., Wong, G. T. et al., *Nature*, 381: 796 (1996).

The tastants were presented at two-fold or three-fold ascending concentrations. The mice were allowed a 7-day recovery period with deionized water between tastants. The order of tastants for Group 1 was sucrose, quinine, SC45647, MSG, acesulfame K, sucralose and glucose. The order of tastants for Group 2 was NaCl, HCl and maltose. All tastants were of the highest purity available. MSG solutions also contained 10 micromolar amiloride to block the salty taste of the Na+. Tastant concentrations are listed below in order of presentation:

| | |
|---|---|
| Sucrose: | 5 mM, 10 mM, 20 mM, 40 mM, 80 mM, 160 mM, 320 mM, 640 mM |
| Quinine: | 0.003 mM, 0.01 mM, 0.03 mM, 0.1 mM, 0.3 mM |
| SC45647: | 0.0025 mM, 0.005 mM, 0.01 mM, 0.02 mM, 0.04 mM, 0.08 mM, 0.16 mM, 0.32 mM, 0.64 mM, 1.2 mM, 2.4 mM, 4.8 mM, 9.6 mM |
| MSG: | 1 mM, 3 mM, 10 mM, 30 mM, 100 mM, 300 mM, 600 mM, 1000 mM |
| Acesulfame K: | 0.001 mM, 0.01 mM, 0.1 mM, 0.3 mM, 1 mM, 3 mM, 10 mM, 30 mM, 100 mM, 300 mM |
| Sucralose: | 0.01 mM, 0.03 mM, 0.1 mM, 0.3 mM, 1 mM, 3 mM, 10 mM, 30 mM |
| Glucose: | 5 mM, 15 mM, 50 mM, 150 mM, 500 mM |
| NaCl: | 18 mM, 37 mM, 75 mM, 150 mM, 300 mM, 600 mM |
| HCl: | 0.01 mM, 0.1 mM, 1 mM, 10 mM, 100 mM |
| Maltose: | 1 mM, 3 mM, 10 mM, 30 mM, 100 mM, 300 mM, 1000 mM. |

Figure 11:
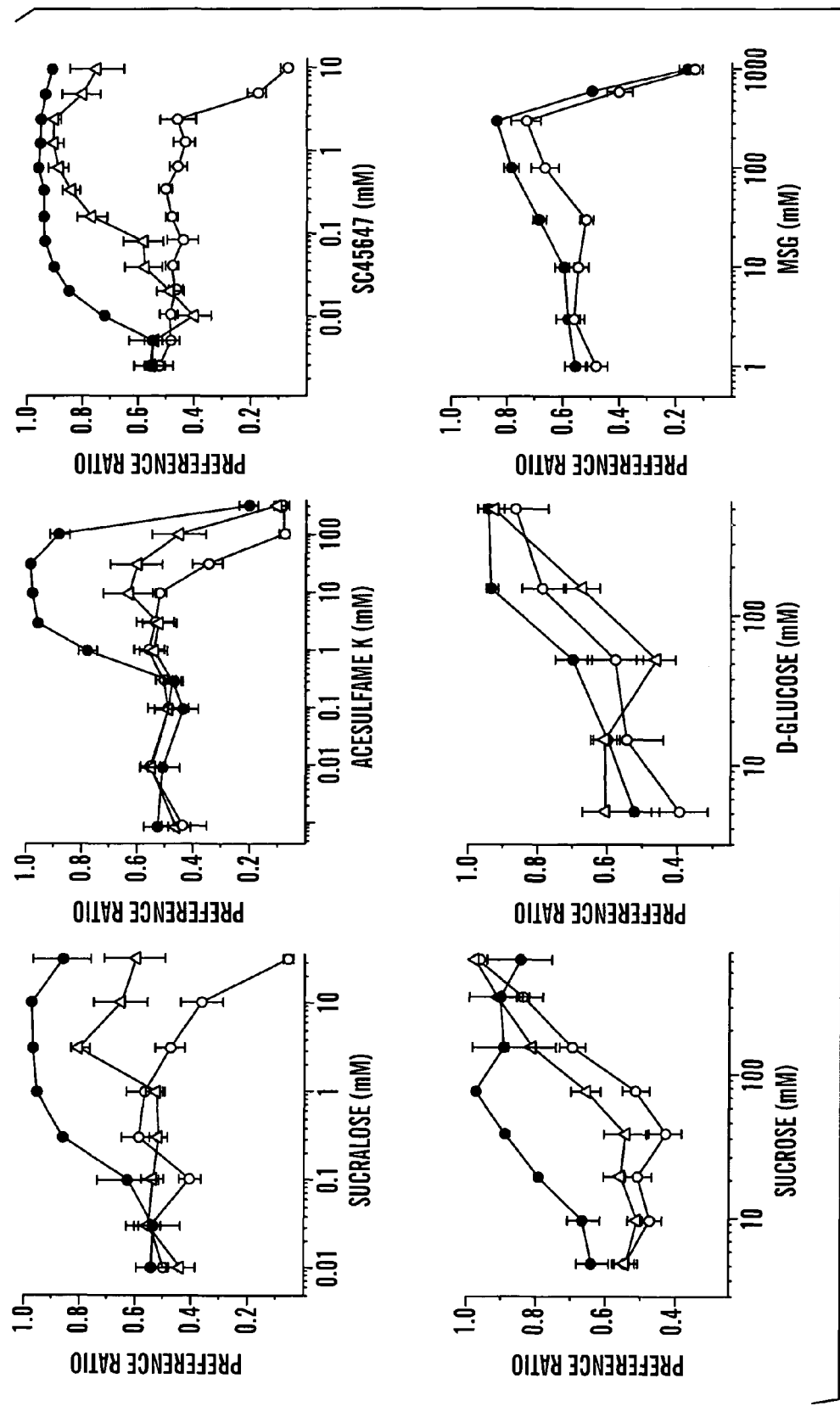
FIG. 11. Mean preference ratios from 48-hour two-bottle preference tests (tastant versus water) comparing T1R3 −/− mice (T1R3 knock-out, open circles), T1R3 +/+ and T1R3 +/− littermate mice (C57BL6 (B6) wild-type, filled circles) and 129T2/SvemsJ mice (129 wild-type, triangles). The mice were given two bottles, one containing water and the other a tastant solution. The ratio of tastant to total liquid consumed after 48 hours was measured and compared between groups. T1R3 knock-out mice displayed markedly diminished behavioral responses to all three artificial sweeteners and sucrose, and moderately diminished behavioral responses to MSG (see Table 1 in Example 3 for F and P values). For responses to glucose, the difference between T1R3 knock-out mice and B6 wild-type mice was borderline (P=0.07). For each group, n=10. Error bars are the standard error of the mean.

In two-bottle preference tests the T1R3 knock-out mice displayed indifference to sucrose and three artificial sweeteners (sucralose, acesulfame K and SC45647) at concentrations that elicited maximal preference in B6 wild-type littermate controls (see FIG. 11). This behavioral data shows that T1R3 is the primary or only taste receptor determining preference for the artificial sweeteners. At concentrations 5- to 10-fold those needed to elicit a strong preference in B6 wild-type mice, the T1R3 knock-out mice preferred sucrose, but avoided all three artificial sweeteners. This suggests that other artificial-sweetener-responsive receptors (such as T2Rs) exist and mediate the well-known bitter aftertaste of these sweeteners (see, e.g., Horne, J. et al., *Chem. Senses*, 27: 31-38 (2002); Schiffman, S. S. et al., *Brain Res. Bull.*, 36: 505-513 (1995)). The response of the T1R3 knock-out mice to glucose was slightly reduced as compared with that of the B6 wild-type control (see FIG. 11), but was not significant at the $P<0.05$ level ($P=0.074$, see Table 1). Thus, there may be additional transduction mechanisms and/or taste receptors responsive to sugars and leading to the preference for sugars.

Figure 15:
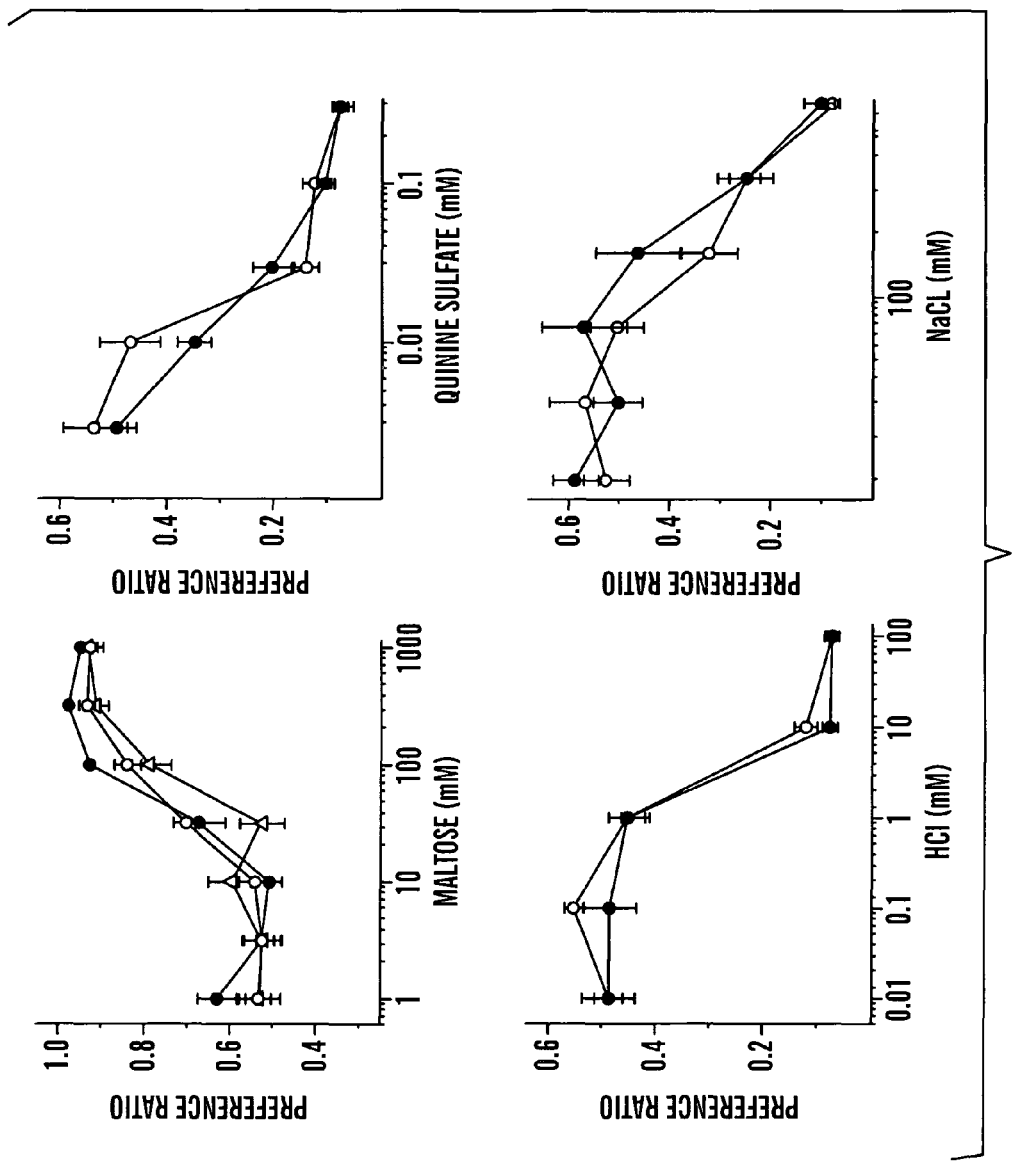
FIG. 15. Mean preference ratios from 48-hour two-bottle preference tests (tastant versus water) comparing T1R3 −/− mice (T1R3 knock-out, open circles), T1R3 +/+ and T1R3 +/− littermate mice (C57BL6 (B6) wild-type, filled circles) and 129T2/SvemsJ mice (129 wild-type, triangles). The mice were given two bottles, one containing water and the other a tastant solution. The ratio of tastant to total liquid consumed after 48 hours was measured and compared between groups. For maltose, n=10 for each group. For quinine sulfate, n=9 for each group. For NaCl and HCl, n=9 for the T1R3 knock-out group and n=8 for the B6 wild-type group. Error bars are the standard error of the mean.

There was no difference in the responses of T1R3 knock-out and B6 wild-type mice to maltose (see FIG. 15). Compared with B6 wild-type mice, the preference of T1R3 knock-out mice for monosodium glutamate (MSG) concentrations between 30 and 300 mM was reduced, but not abolished (see FIG. 11). This indicates that T1R3 plays an important role in umami taste responses, but that it is not the only umami taste receptor. T1R3 knock-out and B6 wild-type mice showed similar responses to quinine sulfate, HCl and NaCl (see FIG. 15), indicating that detection of bitter, sour and salty compounds, respectively, does not involve T1R3.

B6 mice are classified as "tasters" because of their strong preference for sucrose, saccharin and other sweet compounds (Pelz, W. E. et al., *Physiol. Behav.*, 10: 263-265 (1973); Capretta, P. J., *Psychonomic Science*, 21: 133 (1970)). In contrast, 129T2/SvemsJ (129) "nontaster" mice require higher concentrations of sweet compounds to elicit preference (Bachmanov, A. A. et al., *Mamm. Genome*, 8: 545-548 (1997)). To determine if T1R3 in 129 mice is completely non-functional (null) or partially functional (a hypomorph), the behavioral responses to sweet compounds of B6 (taster), 129 (nontaster), and T1R3 knock-out (null) mice were compared. Preference responses to all three artificial sweeteners (sucralose, acesulfame K and SC45647) were strongest in B6 mice, weakest in T1R3 knock-out mice, and intermediate in 129 mice; the mean response of T1R3 knock-out mice to sucrose was weaker than that of 129 mice (FIG. 11). These results suggest that T1R3 is not a null allele in 129 mice, but has reduced functionality for these sweet compounds. The 129 mice did not differ from T1R3 knock-out mice in their responses to glucose and maltose ($P=0.889$ and $0.316$, respectively; see Table 1, FIGS. 11 and 15).

A summary of the statistical analysis of the behavioral and electrophysiological data is provided in Table 1 below.

TABLE 1

| | Two-bottle preference | | | CT Nerve | | GL nerve | |
|---|---|---|---|---|---|---|---|
| Tastant | F | P (KO vs. B6) | P (KO vs. 129) | F | P | F | P |
| Sucrose | 21.144 | <0.001 | 0.109 | 37.359 | <0.001 | 4.894 | 0.057[a] |
| Glucose | 2.947 | 0.074 | 0.889 | 3.080 | 0.117 | ND | ND |
| Maltose | 3.361 | 0.500 | 0.316 | 9.678 | 0.014 | ND | ND |
| Sucralose | 52.316 | <0.001 | 0.003 | 17.360 | 0.003 | ND | ND |
| AceK | 38.434 | <0.001 | 0.055[b] | 26.341 | 0.001 | 14.692 | 0.006 |
| SC45647 | 430.076 | <0.001 | <0.001 | 19.705 | 0.004 | 9.79 | 0.02 |
| MSG | 9.607 | 0.006 | ND | 4.815 | 0.056[c] | 0.216 | 0.654 |
| NaCl | 0.564 | 0.464 | ND | 0.558 | 0.476 | 0.006 | 0.940 |
| Quinine | 0.933 | 0.349 | ND | 1.696 | 0.234 | 0.417 | 0.542 |
| HCl | 1.207 | 0.289 | ND | 0.440 | 0.525 | 0.227 | 0.650 |

[a] $p = 0.036$ for 300 mM, $p = 0.003$ for 500 mM and 1 M
[b] $p = 0.017$ for 30 mM, $p < 0.001$ for 100 mM
[c] $p = 0.027$ for 1000 mM The general linear model for repeated measurements analysis was used to compare the responses of T1R3 knock-out, B6 wild-type and 129 wild-type mice, with tastant concentration as dependant variables and genotype as fixed factor. For each compound, the responses from all concentrations were analyzed together, the response from each concentration being treated as a single value for the multiple measurement analysis. For behavioral tests, the F value is given for comparison of all genotypes. When a significant difference was found, the Tukey's test was used to determine which means differed. P values from the Tukey's test are given for T1R3 knock-out vs. B6 and for T1R3 knock-out vs. 129. When this analysis gave a borderline p value ($0.05<p<0.06$) each concentration was analyzed individually using the general linear model univariate analysis. For CT and GL nerve responses to glucose, maltose and sucralose the general linear model univariate analysis was used because only one concentration was tested for each of these tastants. ND, not done.

Example 4

Characterization of T1R3 Knock-Out and Wild-Type Mice Using Nerve Recordings

To examine the contributions of the gustatory nerves to the behavioral responses, we recorded from the chorda tympani (CT) branch of the facial nerve and the glossopharyngeal (GL) nerve of T1R3 knock-out and B6 wild-type mice. Recordings of electrical impulses from the chorda tympani (CT) and the glossopharyngeal (GL) nerves were performed according to known methods (Kawai, K. et al., *Proc. Nat'l. Acad. Sci. USA*, 97: 11044 (2000)). Male and female mice were used. Tastants were applied at a regular flow rate to the tongue for 30 seconds (CT) or 60 seconds (GL). Tastant concentrations are listed below:

| | |
|---|---|
| Acesulfame K: | 3 mM, 10 mM, 30 mM, 100 mM, 300 mM |
| SC45647: | 0.1 mM, 0.3 mM, 1 mM, 3 mM, 8 mM |
| Sucrose: | 10 mM, 30 mM, 100 mM, 300 mM, 500 mM, 1000 mM |
| Quinine: | 0.01 mM, 0.1 mM, 1 mM, 2 mM |
| HCl: | 0.01 mM, 0.1 mM, 1 mM, 10 mM |
| NaCl: | 10 mM, 30 mM, 100 mM, 300 mM, 1000 mM |
| MSG: | 10 mM, 30 mM, 100 mM, 300 mM, 1000 mM. |

For whole nerve recording, neural activity was amplified, fed into an integrator (time constant=1 second) and displayed on a strip chart recorder. At 5, 10, 15, 20 and 25 seconds (for the CT) and 5, 10, 20, 30 and 40 seconds (for the GL) after stimulus onset the integrated response magnitudes to each stimulus were measured in the chart records as magnitudes of pen deflection (mm) from baseline (before stimulation) and averaged. These averages were normalized to the response to $NH_4Cl$ and analyzed with the General Linear Model Multiple Measures of SPSS with tastant concentrations provided to subjects as "variables" and genotype differences between subjects as "factor". The single concentrations (see FIG. 14) used for the sugars, sorbitol and saccharin were chosen to be in the midrange of CT responses of C57BL6 mice based on previous studies (Ninomiya, Y. and Imoto, T., *Am J. Physiol.*, 268: R1019 (1995); Ninomiya, Y. et al., *Am J. Physiol.*, 269: R930 (1995); Inoue, M. et al., *Chem. Senses*, 26: 915 (2001)). The single concentration of SC45647 chosen (8 mM) was to give a response magnitude comparable to that of saccharin and the sugars (SC45647). Sucralose and D-tryptophan, weak activators of the CT, used the highest possible concentrations or the highest concentrations previously reported with C57BL6 mice (Ninomiya, Y. and Imoto, T., *Am J. Physiol.*, 268: R1019 (1995); Ninomiya, Y. et al., *Am J. Physiol.*, 269: R930 (1995)).

Figure 12:
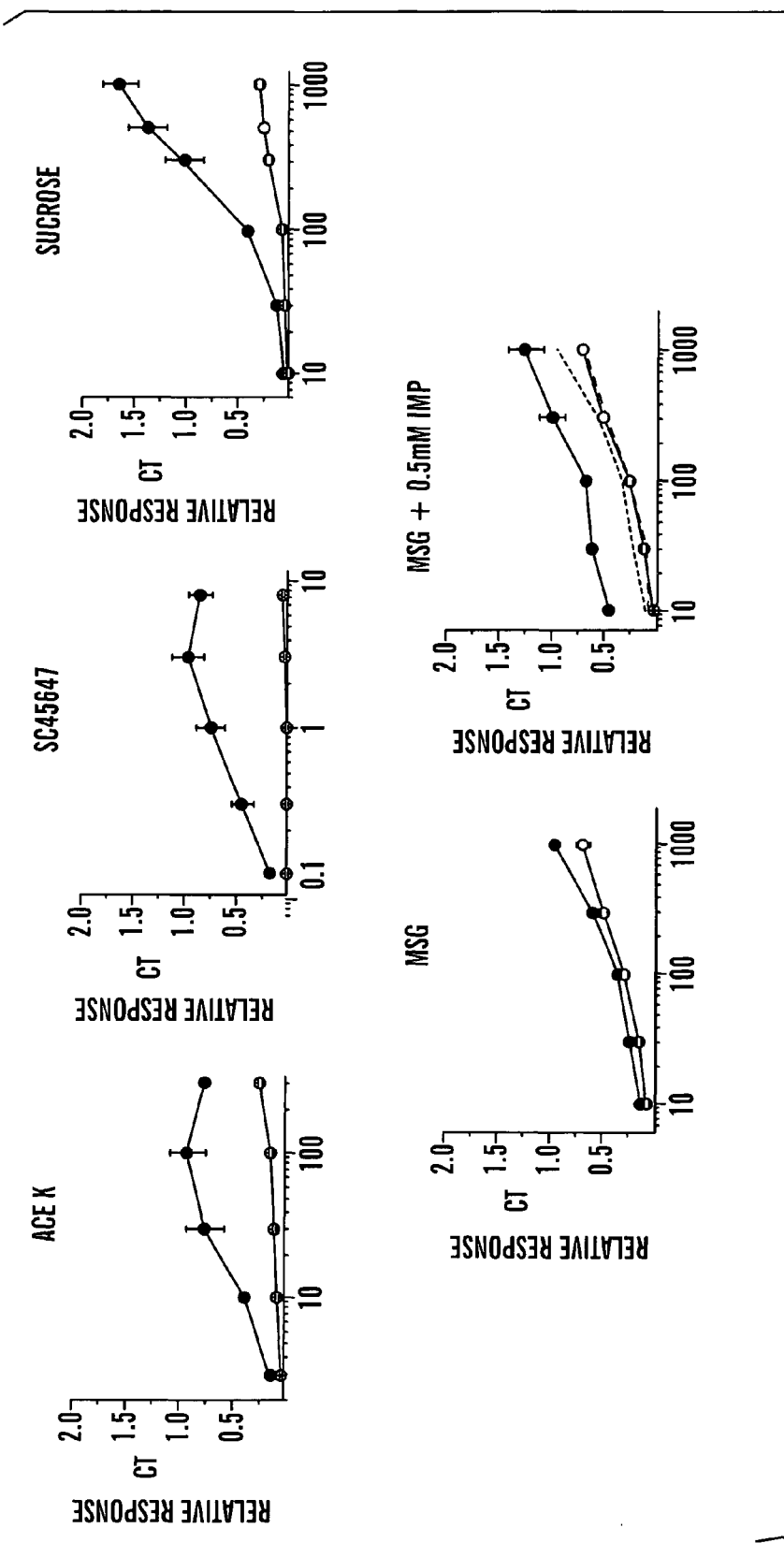
FIG. 12. Whole-nerve recordings from taste nerves of B6 wild-type and T1R3 knock-out mice stimulated by lingual application of taste stimuli. Integrated chorda tympani (CT) responses of wild-type mice (filled circles) and T1R3 knock-out mice (open circles) in response to lingual application of a concentration series of tastants, normalized to the response to 100 mM $NH_4Cl$ ($NH_4Cl$ response=1.0). Compared with the responses of B6 wild-type mice, CT responses of T1R3 knock-out mice were markedly diminished to acesulfame K, SC45647, sucrose and MSG+IMP, and slightly diminished to MSG (see Table 1 in Example 3 for F and P values). In the MSG+IMP graph, the dotted curve shows the response of the B6 wild-type mice to MSG alone, and the dashed curve shows the response of T1R3 knock-out mice to MSG alone. All concentrations are in millimolar. Error bars are the standard error of the mean. For each group, n=5. For details and results of the statistical analysis, see Table 1 in Example 3.
Figure 14:
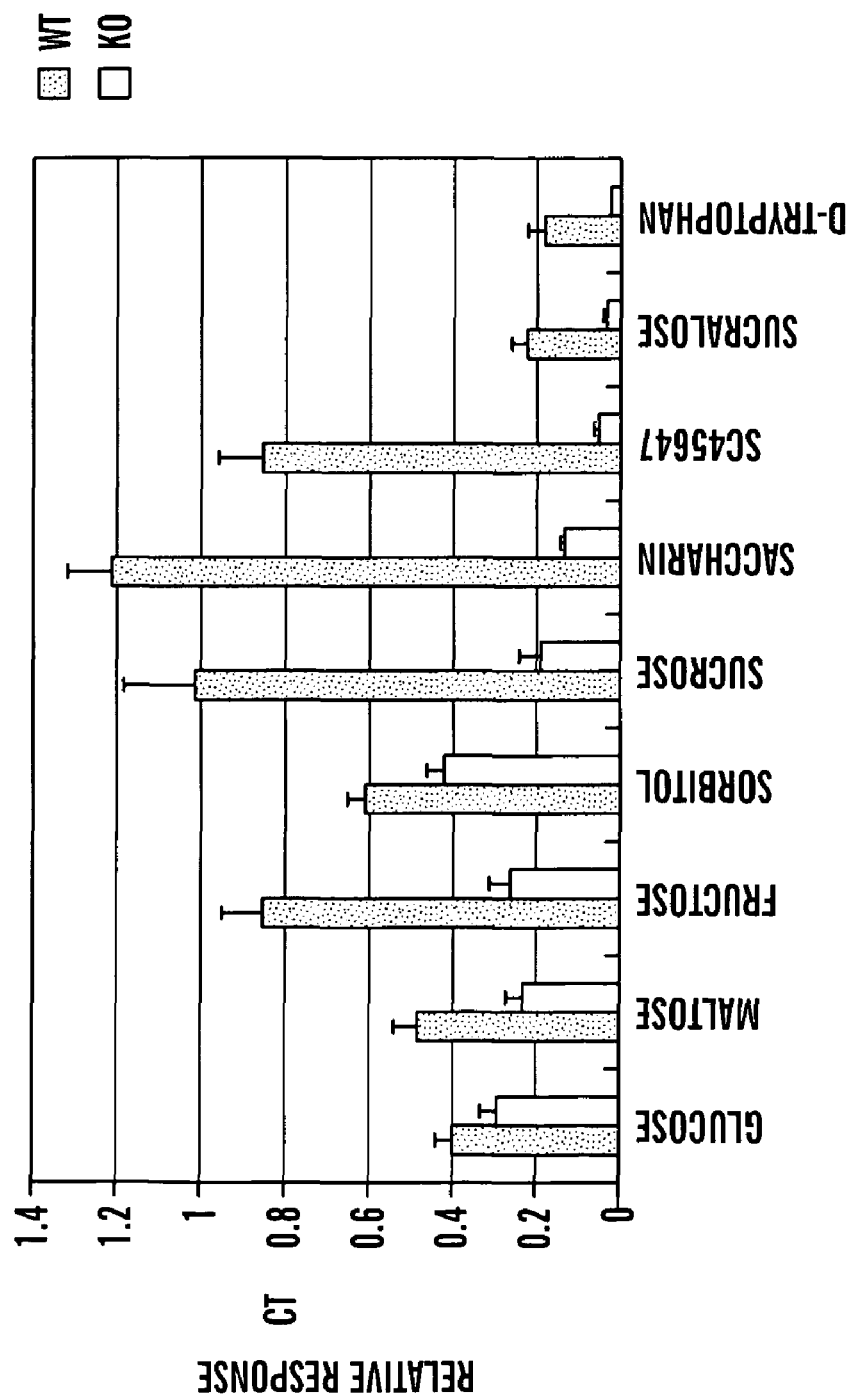
FIG. 14. Whole-nerve recordings from taste nerves of B6 wild-type and T1R3 knock-out mice stimulated by lingual application of taste stimuli. Integrated CT responses of wild-type mice (filled bars) and T1R3 knock-out mice (open bars) in response to lingual application of single concentrations of sweet tastants, normalized to the response to 100 mM $NH_4Cl$ ($NH_4Cl$ response=1.0). In addition to the T1R3 knock-out mice versus wild-type mice differences noted in FIG. 3A, significant differences were observed with maltose (see Table 1 in Example 3 for F and P values), fructose (F=39.8, P<0.001), sorbitol (F=9.9, P=0.014) and D-tryptophan (F=19.8, P=0.002). The following single concentrations were tested: 500 mM glucose, 500 mM maltose, 500 mM fructose, 1 M sorbitol, 300 mM sucrose, 20 mM saccharin, 8 mM SC45647, 25 mM sucralose and 30 mM D-tryptophan. Error bars are the standard error of the mean. For each group, n=5. For details and results of the statistical analysis, see Table 1 in Example 3.
Figure 18:
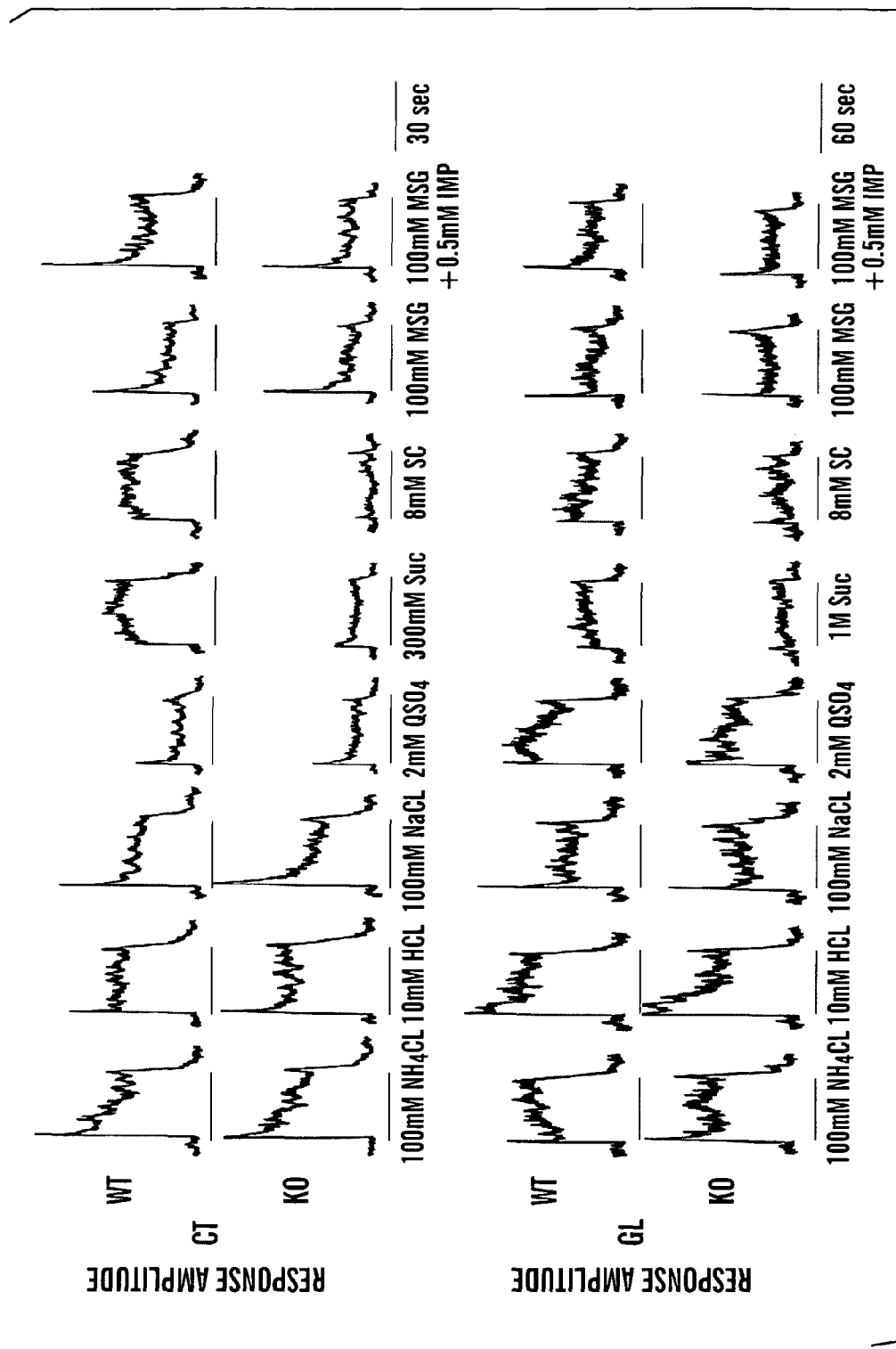
FIG. 18. Whole-nerve recordings from taste nerves of B6 wild-type and T1R3 knock-out mice stimulated by lingual application of taste stimuli. Integrated neural responses of the CT (upper traces) and GL (lower traces) from wild-type and T1R3 knock-out mice. The duration of tastant application (30 seconds for CT, 60 seconds for GL) is indicated. All concentrations are in millimolar. Error bars are the standard error of the mean. For each group and each nerve, n=5.

Whole nerve recordings from the CT nerve of T1R3 knock-out mice showed near-zero responses to all four artificial sweeteners tested (acesulfame K, SC45647, saccharin and sucralose) (see FIGS. 12, 14 and 18). Compared with the CT response of B6 wild-type mice, the CT responses of the T1R3 knock-out mice to sweet-tasting amino acids, sugar alcohols and sugars ranged from near-zero (D-tryptophan), to moderately or markedly diminished (sucrose, fructose, maltose and sorbitol), to not significantly diminished (glucose) (see FIG. 14). This CT response to all of the sugars tested, particularly glucose, was consistent with the behavioral data and suggests that there are additional transduction mechanisms and/or taste receptors that respond to sugars.

Compared with the CT response of B6 wild-type mice, the CT responses of T1R3 knock-out mice to MSG were diminished only at the highest concentration tested (See FIG. 12). This indicated that T1R3 probably plays some role in CT responses to MSG.

Figure 16:
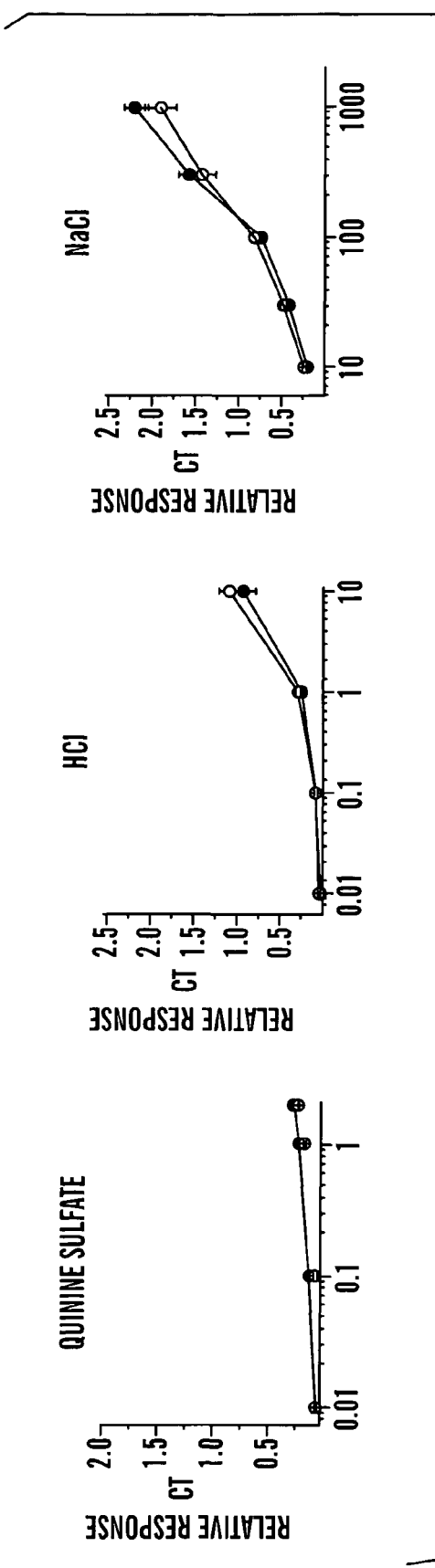
FIG. 16. Whole-nerve recordings from taste nerves of B6 wild-type and T1R3 knock-out mice stimulated by lingual application of taste stimuli. Integrated chorda tympani (CT) responses of wild-type mice (filled circles) and T1R3 knock-out mice (open circles) in response to lingual application of a concentration series of tastants, normalized to the response to 100 mM $NH_4Cl$ ($NH_4Cl$ response=1.0). All concentrations are in millimolar. Error bars are the standard error of the mean. For each group, n=5.
Figure 17:
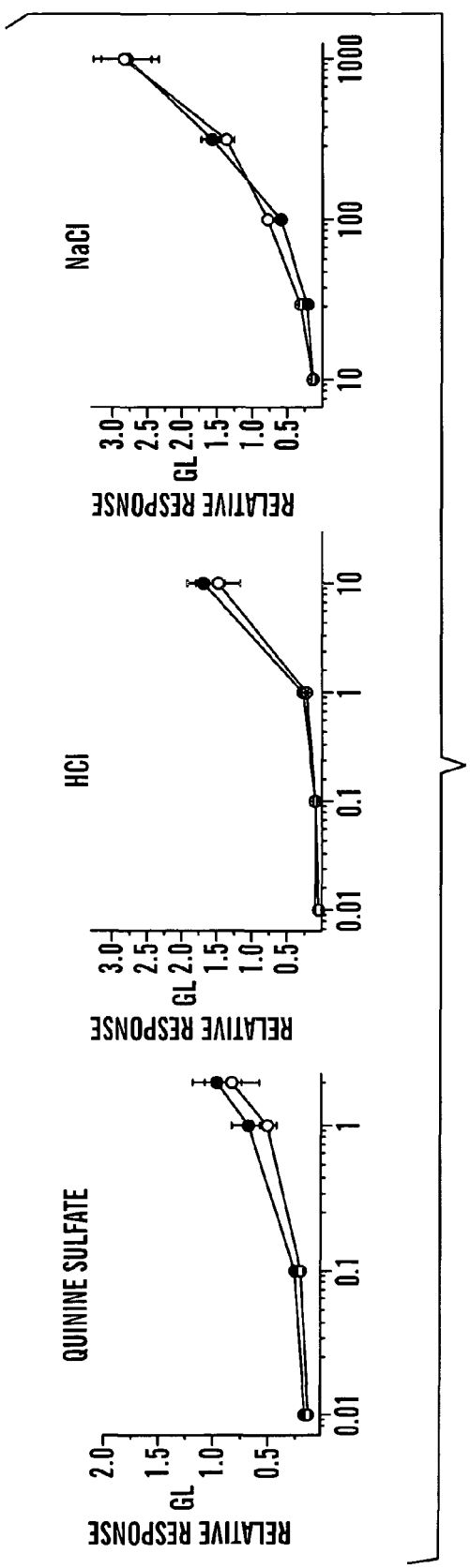
FIG. 17. Whole-nerve recordings from taste nerves of B6 wild-type and T1R3 knock-out mice stimulated by lingual application of taste stimuli. Integrated glossopharyngeal (GL) responses of wild-type mice (filled circles) and T1R3 knock-out mice (open circles) in response to lingual application of tastants, normalized to the response to 100 mM $NH_4Cl$ (NH₄Cl response=1.0). All concentrations are in millimolar. Error bars are the standard error of the mean. For each group, n=5.

Inosine monophosphate (IMP) is a known potentiator of umami responses, enhancing behavioral and CT nerve responses to MSG by approximately one order of magnitude (Ninomiya, Y. et al., *J. Nutr.*, 130: 950S-953S (2000)). Compared with the CT response of B6 wild-type mice, the T1R3 knock-out mice displayed markedly reduced CT responses to MSG+IMP (umami) (see FIG. 12). Indeed, the CT responses of T1R3 knock-out mice to MSG+IMP were indistinguishable from those to MSG alone, as if they had lost the potentiating effect of IMP. Thus, T1R3 is essential for the CT response to MSG+IMP. T1R3 knock-out and B6 control mice showed similar responses to quinine sulfate, HCl and NaCl (see FIGS. 16-18), consistent with the behavioral data.

Figure 13:
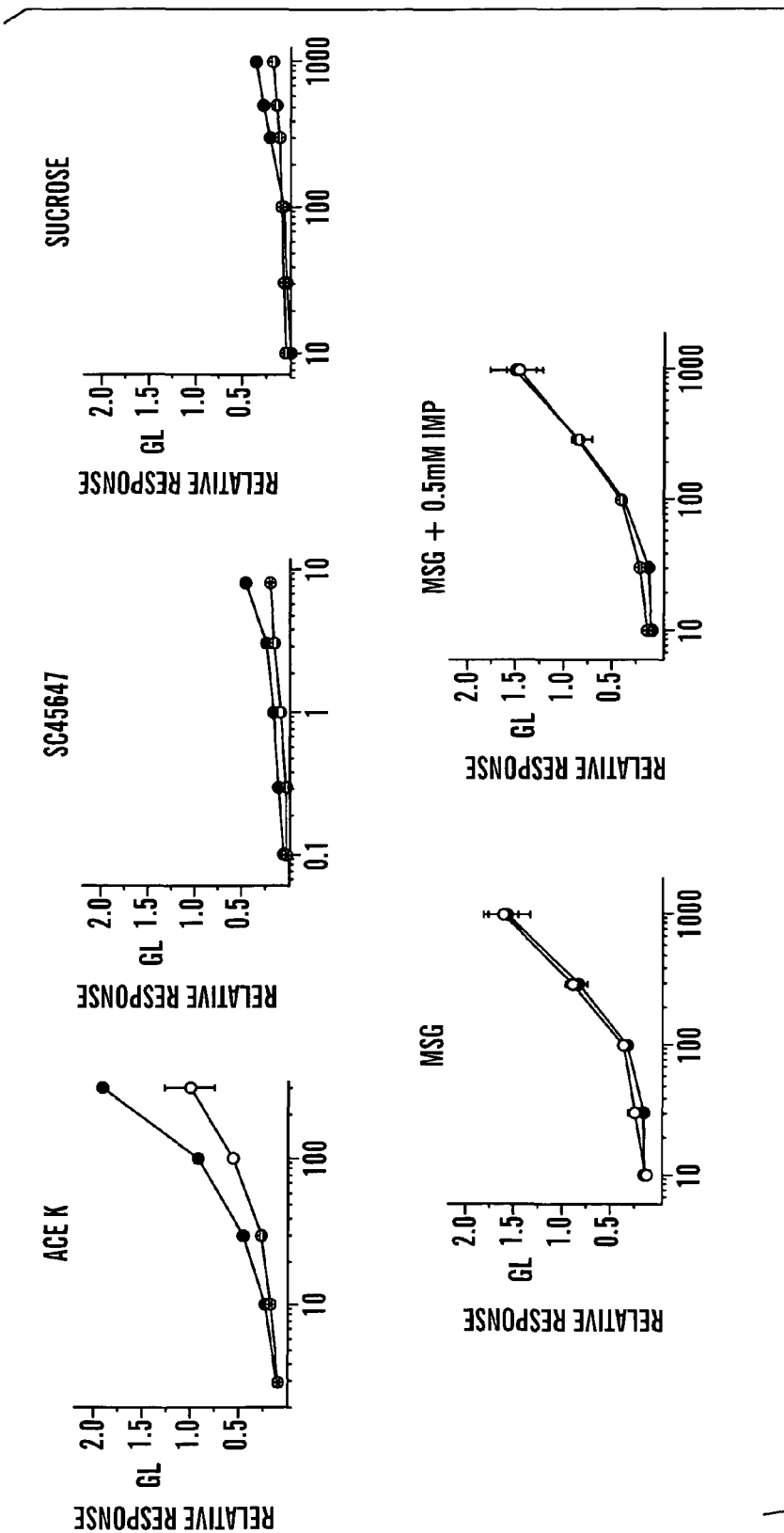
FIG. 13. Whole-nerve recordings from taste nerves of B6 wild-type and T1R3 knock-out mice stimulated by lingual application of taste stimuli. Integrated glossopharyngeal (GL) responses of wild-type mice (filled circles) and T1R3 knock-out mice (open circles) in response to lingual application of tastants, normalized to the response to 100 mM $NH_4Cl$ ($NH_4Cl$ response=1.0). In general, responses to sweet compounds were lower in the GL than in the CT. Significant differences were noted between T1R3 knock-out mice and B6 wild-type mice in responses to acesulfame K, SC45647, sucrose and MSG+IMP, but not in response to MSG alone (see Table 1 in Example 3 for F and P values). For MSG+IMP P<0.001 and F=40.848. All concentrations are in millimolar. Error bars are the standard error of the mean. For each group, n=5. For details and results of the statistical analysis, see Table 1 in Example 3.

T1R3 is expressed in both anterior and posterior tongue regions (Kitagawa, M. et al., *Biochem. Biophys. Res. Commun.*, 283: 236 (2001); Max, M. et al., *Nat. Genet.*, 28: 58 (2001); Montmayeur, J. P. et al., *Nat. Neurosci.*, 4: 492 (2001); Sainz, E. et al., *J. Neurochem.*, 77: 896 (2001); Nelson, G. et al., *Cell*, 106: 381 (2001); Bachmanov, A. A. et al., *Chem. Senses*, 26: 925 (2001)), so it was of interest to know what effect its absence from posterior taste buds might have on GL nerve responses. In rodents the GL nerve is relatively more responsive to bitter compounds, while the CT nerve is relatively more responsive to sweet compounds (Shingai, T. and Beidler, L. M., *Brain Res.*, 335: 245 (1985); Ninomiya, Y. et al., *Neurosci. Lett.*, 163: 197 (1993); Sako, N. et al., *Physiol. Behav.*, 71: 193 (2000)). As expected, the GL nerve responses of B6 wild-type mice to the sweet compounds SC45647 and sucrose were much lower than were their CT responses to these compounds (FIGS. 12, 13 and 18). Compared with the CT nerve responses, the GL nerve responses of B6 wild-type mice to acesulfame K were lower at concentrations below 100 mM, but higher at 300 mM. This may explain the aversion to higher concentrations of acesulfame K evident in the behavioral assays (see FIG. 11). Compared with B6 wild-type mice, the T1R3 knock-out mice showed reduced GL responses to the three sweet compounds tested (sucrose, SC45647 and acesulfame K); for sucrose and SC45647, this was only evident at the highest concentration tested, for acesulfame K this was evident from 30-300 mM (see FIGS. 13 and 18). In contrast to the CT results, no differences between B6 wild-type and T1R3 knock-out mice were noted in the GL responses to either MSG alone or MSG+IMP (see FIG. 13), suggesting that T1R3 does not underlie umami responses mediated by the GL nerve. GL responses to quinine sulfate, HCl and NaCl were unchanged in T1R3 knock-out mice as compared with B6 wild-type mice (see FIGS. 16-18), consistent with the behavioral and CT data.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Various references are cited herein, the disclosures of which are incorporated by reference in their entireties.

What is claimed is:

1. A transgenic mouse comprising an endogenous T1R3 gene in the mouse's germ and somatic cells that has been rendered nonfunctional by recombination with a heterologous nucleotide sequence, wherein the mouse (i) is homozygous for nonfunctional endogenous T1R3, (ii) is essentially free of any functional T1R3 protein, and (iii) exhibits an impaired response to a sweet tastant and an umami tastant.

2. The transgenic mouse of claim 1, wherein the mouse exhibits an altered nerve response to a tastant.

* * * * *

SEQUENCE LISTING

<160> NUMBER OF SEQ ID NOS: 16

<210> SEQ ID NO 1
<211> LENGTH: 2729
<212> TYPE: DNA
<213> ORGANISM: Human

<400> SEQUENCE: 1

```
ggacaccact ggggccccag ggtgtggcaa gtgaggatgg caagggtttt gctaaacaaa        60
tcctctgccc gctccccgcc ccgggctcac tccatgtgag gccccagtcg gggcagccac       120
ctgccgtgcc tgttggaagt tgcctctgcc atgctgggcc ctgctgtcct gggcctcagc       180
ctctgggctc tcctgcaccc tgggacgggg gccccattgt gcctgtcaca gcaacttagg       240
atgaaggggg actacgtgct ggggggggctg ttccccctgg gcgaggccga ggaggctggc       300
ctccgcagcc ggacacggcc cagcagccct gtgtgcacca ggtaggttct cctcaaacgg       360
cctgctctgg gcactggcca tgaaaatggc cgtggaggag atcaacaaca agtcggatct       420
gctgcccggg ctgcgcctgg gctacgacct ctttgatacg tgctcggagc ctgtggtggc       480
catgaagccc agcctcatgt tcctggccaa ggcaggcagc cgcgacatcg ccgcctactg       540
caactacacg cagtaccagc cccgtgtgct ggctgtcatc gggcccact cgtcagagct       600 cgccatggtc accggcaagt tcttcagctt cttcctcatg ccccaggtag gtcagctacg       660
gtgctagcat ggagctgctg agcgcccggg agaccttccc ctccttcttc cgcaccgtgc       720
ccagcgaccg tgtgcagctg acggccgccg cggagctgct gcaggagttc ggctggaact       780
gggtggccgc cctgggcagc gacgacgagt acggccggca gggcctgagc atcttctcgg       840
ccctggccgc ggcacgcggc atctgcatcg cgcacgaggg cctggtgccg ctgccccgtg       900
ccgatgactc gcggctgggg aaggtgcagg acgtcctgca ccaggtgaac cagagcagcg       960
```

```
tgcaggtggt gctgctgttc gcctccgtgc acgccgccca cgccctcttc aactacagca   1020
tcagcagcag gctctcgccc aaggtgtggg tggccagcga ggcctggctg acctctgacc   1080
tggtcatggg gctgcccggc atggcccaga tgggcacggt gcttggcttc ctccagaggg   1140
gtgcccagct gcacgagttc ccccagtacg tgaagacgca cctggccctg ccaccgacc    1200
cggccttctg ctctgccctg ggcgagaggg agcagggtct ggaggaggac gtggtgggcc   1260
agcgctgccc gcagtgtgac tgcatcacgc tgcagaacgt gagcgcaggg ctaaatcacc   1320
accagacgtt ctctgtctac gcagctgtgt atagcgtggc ccaggccctg cacaacactc   1380
ttcagtgcaa cgcctcaggc tgccccgcgc aggaccccgt gaagccctgg caggtagctc   1440
ctggagaaca tgtacaacct gaccttccac gtgggcgggc tgccgctgcg gttcgacagc   1500
agcggaaacg tggacatgga gtacgacctg aagctgtggg tgtggcaggg ctcagtgccc   1560
aggctccacg acgtgggcag gttcaacggc agcctcagga cagagcgcct gaagatccgc   1620
tggcacacgt ctgacaacca ggtagaagcc cgtgtcccgg tgctcgcggc agtgccagga   1680
gggccaggtg cgccgggtca aggggttcca ctcctgctgc tacgactgtg tggactgcga   1740
ggcgggcagc taccggcaaa acccaggtag acgacatcgc ctgcaccttt tgtggccagg   1800
atgagtggtc cccggagcga agcacacgct gcttccgccg caggtctcgg ttcctggcat   1860
ggggcgagcc ggctgtgctg ctgctgctcc tgctgctgag cctggcgctg ggccttgtgc   1920
tggctgcttt ggggctgttc gttcaccatc gggacagccc actggttcag gcctcggggg   1980
ggcccctggc ctgctttggc ctggtgtgcc tgggcctggt ctgcctcagc gtcctcctgt   2040
tccctggcca gcccagccct gcccgatgcc tgcccagca gcccttgtcc cacctcccgc    2100
tcacgggctg cctgagcaca ctcttcctgc aggcggccga gatcttcgtg gagtcagaac   2160
tgcctctgag ctgggcagac cggctgagtg gctgcctgcg ggggccctgg gcctggctgg   2220
tggtgctgct ggccatgctg gtggaggtcg cactgtgcac ctggtacctg gtggccttcc   2280
cgccggaggt ggtgacggac tggcacatgc tgcccacgga ggcgctggtg cactgccgca   2340
cacgctcctg ggtcagcttc ggcctagcgc acgccaccaa tgccacgctg gcctttctct   2400
gcttcctggg cactttcctg gtgcggagcc agccgggccg ctacaaccgt gcccgtggcc   2460
tcacctttgc catgctggcc tacttcatca cctgggtctc cttgtgccc  ctcctggcca   2520
atgtgcaggt ggtcctcagg cccgccgtgc agatgggcgc cctcctgctc tgtgtcctgg   2580
gcatcctggc tgccttccac ctgcccaggt gttacctgct catgcggcag ccagggctca   2640
acacccccga gttcttcctg ggaggggcc ctggggatgc ccaaggccag aatgacggga    2700
acacaggaaa tcaggggaaa catgagtga                                     2729
```

<210> SEQ ID NO 2
<211> LENGTH: 852
<212> TYPE: PRT
<213> ORGANISM: Human

<400> SEQUENCE: 2

Met Leu Gly Pro Ala Val Leu Gly Leu Ser Leu Trp Ala Leu Leu His
 1               5                  10                  15

Pro Gly Thr Gly Ala Pro Leu Cys Leu Ser Gln Gln Leu Arg Met Lys
            20                  25                  30

Gly Asp Tyr Val Leu Gly Gly Leu Phe Pro Leu Gly Glu Ala Glu Glu
        35                  40                  45

Ala Gly Leu Arg Ser Arg Thr Arg Pro Ser Ser Pro Val Cys Thr Arg
    50                  55                  60

```
Phe Ser Ser Asn Gly Leu Leu Trp Ala Leu Ala Met Lys Met Ala Val
 65                  70                  75                  80

Glu Glu Ile Asn Asn Lys Ser Asp Leu Leu Pro Gly Leu Arg Leu Gly
                 85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Ser Gln Glu Phe Gly Trp Asn Trp
        195                 200                 205

Val Ala Ala Leu Gly Ser Asp Asp Glu Tyr Gly Arg Gln Gly Leu Ser
210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
                245                 250                 255

Gln Asp Val Leu His Gln Val Asn Gln Ser Ser Val Gln Val Val Leu
            260                 265                 270

Leu Phe Ala Ser Val His Ala Ala His Ala Leu Phe Asn Tyr Ser Ile
        275                 280                 285

Ser Ser Arg Leu Ser Pro Lys Val Trp Val Ala Ser Glu Ala Trp Leu
290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
        435                 440                 445

Asn Val Asp Met Glu Tyr Asp Leu Lys Leu Trp Val Trp Gln Gly Ser
450                 455                 460

Val Pro Arg Leu His Asp Val Gly Arg Phe Asn Gly Ser Leu Arg Thr
465                 470                 475                 480
```

-continued

```
Glu Arg Leu Lys Ile Arg Trp His Thr Ser Asp Asn Gln Lys Pro Val
            485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
            515                 520                 525

Tyr Arg Gln Asn Pro Asp Asp Ile Ala Cys Thr Phe Cys Gly Gln Asp
            530                 535                 540

Glu Trp Ser Pro Glu Arg Ser Thr Arg Cys Phe Arg Arg Ser Arg
545                 550                 555                 560

Phe Leu Ala Trp Gly Glu Pro Ala Val Leu Leu Leu Leu Leu Leu Leu
            565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
            595                 600                 605

Phe Gly Leu Val Cys Leu Gly Leu Val Cys Leu Ser Val Leu Leu Phe
            610                 615                 620

Pro Gly Gln Pro Ser Pro Ala Arg Cys Leu Ala Gln Gln Pro Leu Ser
625                 630                 635                 640

His Leu Pro Leu Thr Gly Cys Leu Ser Thr Leu Phe Leu Gln Ala Ala
            645                 650                 655

Glu Ile Phe Val Glu Ser Glu Leu Pro Leu Ser Trp Ala Asp Arg Leu
            660                 665                 670

Ser Gly Cys Leu Arg Gly Pro Trp Ala Trp Leu Val Val Leu Leu Ala
            675                 680                 685

Met Leu Val Glu Val Ala Leu Cys Thr Trp Tyr Leu Val Ala Phe Pro
            690                 695                 700

Pro Glu Val Val Thr Asp Trp His Met Leu Pro Thr Glu Ala Leu Val
705                 710                 715                 720

His Cys Arg Thr Arg Ser Trp Val Ser Phe Gly Leu Ala His Ala Thr
            725                 730                 735

Asn Ala Thr Leu Ala Phe Leu Cys Phe Leu Gly Thr Phe Leu Val Arg
            740                 745                 750

Ser Gln Pro Gly Arg Tyr Asn Arg Ala Arg Gly Leu Thr Phe Ala Met
            755                 760                 765

Leu Ala Tyr Phe Ile Thr Trp Val Ser Phe Val Pro Leu Leu Ala Asn
            770                 775                 780

Val Gln Val Val Leu Arg Pro Ala Val Gln Met Gly Ala Leu Leu Leu
785                 790                 795                 800

Cys Val Leu Gly Ile Leu Ala Ala Phe His Leu Pro Arg Cys Tyr Leu
            805                 810                 815

Leu Met Arg Gln Pro Gly Leu Asn Thr Pro Glu Phe Phe Leu Gly Gly
            820                 825                 830

Gly Pro Gly Asp Ala Gln Gly Gln Asn Asp Gly Asn Thr Gly Asn Gln
            835                 840                 845

Gly Lys His Glu
    850

<210> SEQ ID NO 3
<211> LENGTH: 546
<212> TYPE: PRT
<213> ORGANISM: Mouse

<400> SEQUENCE: 3
```

```
Met Pro Ala Leu Ala Ile Met Gly Leu Ser Leu Ala Ala Phe Leu Glu
  1               5                  10                  15

Leu Gly Met Gly Ala Ser Leu Cys Leu Ser Gln Gln Phe Lys Ala Gln
             20                  25                  30

Gly Asp Tyr Ile Leu Gly Gly Leu Phe Pro Leu Gly Ser Thr Glu Glu
         35                  40                  45

Ala Thr Leu Asn Gln Arg Thr Gln Pro Asn Ser Ile Pro Cys Asn Arg
     50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
            115                 120                 125

Cys Asn Tyr Thr Gln Tyr Gln Pro Arg Val Leu Ala Val Ile Gly Pro
130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Tyr Gly Arg Glu Gly Leu Ser
210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285

His His Gly Leu Ser Pro Lys Val Trp Val Ala Ser Glu Ser Trp Leu
290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
        355                 360                 365

Cys Pro Arg Cys Asp Asp Ile Met Leu Gln Asn Leu Ser Ser Gly Leu
370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415
```

```
Cys Asn Val Ser His Cys His Val Ser Glu His Val Leu Pro Trp Gln
            420                 425                 430

Leu Leu Glu Asn Met Tyr Asn Met Ser Phe His Ala Arg Asp Leu Thr
            435                 440                 445

Leu Gln Phe Asp Ala Glu Gly Asn Val Asp Met Glu Tyr Asp Leu Lys
            450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
            515                 520                 525

Cys Lys Ala Gly Ser Tyr Arg Lys His Pro Asp Asp Phe Thr Cys Thr
            530                 535                 540

Pro Cys
545

<210> SEQ ID NO 4
<211> LENGTH: 538
<212> TYPE: PRT
<213> ORGANISM: Rat

<400> SEQUENCE: 4

Met Leu Phe Trp Ala Ala His Leu Leu Leu Ser Leu Gln Leu Val Tyr
1               5                   10                  15

Cys Trp Ala Phe Ser Cys Gln Arg Thr Glu Ser Ser Pro Gly Phe Ser
            20                  25                  30

Leu Pro Gly Asp Phe Leu Leu Ala Gly Leu Phe Ser Leu His Gly Asp
            35                  40                  45

Cys Leu Gln Val Arg His Arg Pro Leu Val Thr Ser Cys Asp Arg Pro
        50                  55                  60

Asp Ser Phe Asn Gly His Gly Tyr His Leu Phe Gln Ala Met Arg Phe
65              70                  75                  80

Thr Val Glu Glu Ile Asn Asn Ser Ser Ala Leu Leu Pro Asn Ile Thr
                85                  90                  95

Leu Gly Tyr Glu Leu Tyr Asp Val Cys Ser Glu Ser Ala Asn Val Tyr
            100                 105                 110

Ala Thr Leu Arg Val Leu Ala Leu Gln Gly Pro Arg His Ile Glu Ile
            115                 120                 125

Gln Lys Asp Leu Arg Asn His Ser Ser Lys Val Val Ala Phe Ile Gly
        130                 135                 140

Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
                165                 170                 175

Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
            195                 200                 205

Trp Ile Ser Leu Ile Gly Ser Tyr Gly Asp Tyr Gly Gln Leu Gly Val
        210                 215                 220

Gln Ala Leu Glu Glu Leu Ala Val Pro Arg Gly Ile Cys Val Ala Phe
225                 230                 235                 240
```

-continued

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
            260                 265                 270

Phe Ser Asn Arg His Leu Ala Arg Val Phe Phe Arg Ser Val Val Leu
        275                 280                 285

Ala Asn Leu Thr Gly Lys Val Trp Val Ala Ser Glu Asp Trp Ala Ile
    290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
            340                 345                 350

Glu Gly Ser Trp Ser Thr Cys Asn Gln Leu Cys Arg Glu Cys His Thr
        355                 360                 365

Phe Thr Thr Arg Asn Met Pro Thr Leu Gly Ala Phe Ser Met Ser Ala
    370                 375                 380

Ala Tyr Arg Val Tyr Glu Ala Val Tyr Ala Val Ala His Gly Leu His
385                 390                 395                 400

Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
            420                 425                 430

Glu Asn Thr Val Ala Phe Asp Asp Asn Gly Asp Thr Leu Gly Tyr Tyr
        435                 440                 445

Asp Ile Ile Ala Trp Asp Trp Asn Gly Pro Glu Trp Thr Phe Glu Ile
    450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Val Gly Ser His
            500                 505                 510

His Cys Cys Phe Glu Cys Val Pro Cys Glu Ala Gly Thr Phe Leu Asn
        515                 520                 525

Met Ser Glu Leu His Ile Cys Gln Pro Cys
    530                 535

<210> SEQ ID NO 5
<211> LENGTH: 542
<212> TYPE: PRT
<213> ORGANISM: Rat

<400> SEQUENCE: 5

Met Gly Pro Gln Ala Arg Thr Leu Cys Leu Leu Ser Leu Leu Leu His
1               5                   10                  15

Val Leu Pro Lys Pro Gly Lys Leu Val Glu Asn Ser Asp Phe His Leu
            20                  25                  30

Ala Gly Asp Tyr Leu Leu Gly Gly Leu Phe Thr Leu His Ala Asn Val
        35                  40                  45

Lys Ser Ile Ser His Leu Ser Tyr Leu Gln Val Pro Lys Cys Asn Glu
    50                  55                  60

Phe Thr Met Lys Val Leu Gly Tyr Asn Leu Met Gln Ala Met Arg Phe

```
            65                  70                  75                  80
Ala Val Glu Glu Ile Asn Asn Cys Ser Ser Leu Leu Pro Gly Val Leu
                     85                  90                  95

Leu Gly Tyr Glu Met Val Asp Val Cys Tyr Leu Ser Asn Asn Ile His
                    100                 105                 110

Pro Gly Leu Tyr Phe Leu Ala Gln Asp Asp Leu Leu Pro Ile Leu
                115                 120                 125

Lys Asp Tyr Ser Gln Tyr Met Pro His Val Val Ala Val Ile Gly Pro
    130                 135                 140

Asp Asn Ser Glu Ser Ala Ile Thr Val Ser Asn Ile Leu Ser His Phe
145                 150                 155                 160

Leu Ile Pro Gln Ile Thr Tyr Ser Ala Ile Ser Asp Lys Leu Arg Asp
                165                 170                 175

Lys Arg His Phe Pro Ser Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Tyr Gly Arg Glu Asn Ser His
    210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Thr Ser
            260                 265                 270

Ala Arg Val Val Val Phe Ser Pro Glu Leu Ser Leu Tyr Ser Phe
    275                 280                 285

Phe His Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
            340                 345                 350

Val Pro Asn Thr Thr Asn Leu Arg Thr Thr Cys Asn Gln Asp Cys Asp
        355                 360                 365

Ala Cys Leu Asn Thr Thr Lys Ser Phe Asn Asn Ile Leu Ile Leu Ser
    370                 375                 380

Gly Glu Arg Val Val Tyr Ser Val Tyr Ser Ala Val Tyr Ala Val Ala
385                 390                 395                 400

His Ala Leu His Arg Leu Leu Gly Cys Asn Arg Val Arg Cys Thr Lys
                405                 410                 415

Gln Lys Val Tyr Pro Trp Gln Leu Leu Arg Glu Ile Trp His Val Asn
            420                 425                 430

Phe Thr Leu Leu Gly Asn Arg Leu Phe Phe Asp Gln Gln Gly Asp Met
        435                 440                 445

Pro Met Leu Leu Asp Ile Ile Gln Trp Gln Trp Asp Leu Ser Gln Asn
    450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
                485                 490                 495
```

```
Ser Met Cys Ser Lys Ser Cys Gln Pro Gly Gln Met Lys Lys Ser Val
            500                 505                 510

Gly Leu His Pro Cys Cys Phe Glu Cys Leu Asp Cys Met Pro Gly Thr
        515                 520                 525

Tyr Leu Asn Arg Ser Ala Asp Glu Phe Asn Cys Leu Ser Cys
    530                 535                 540

<210> SEQ ID NO 6
<211> LENGTH: 585
<212> TYPE: PRT
<213> ORGANISM: Murine

<400> SEQUENCE: 6

Met Ala Trp Phe Gly Tyr Cys Leu Ala Leu Leu Ala Leu Thr Trp His
  1               5                  10                  15

Ser Ser Ala Tyr Gly Pro Asp Gln Arg Ala Gln Lys Lys Gly Asp Ile
             20                  25                  30

Ile Leu Gly Gly Leu Phe Pro Ile His Phe Gly Val Ser Ala Lys Asp
         35                  40                  45

Gln Asp Leu Lys Ser Arg Pro Glu Ser Val Glu Cys Ile Arg Tyr Asn
     50                  55                  60

Phe Arg Gly Phe Arg Trp Leu Gln Ala Met Ile Phe Ala Ile Glu Glu
 65                  70                  75                  80

Ile Asn Ser Ser Pro Ala Leu Leu Pro Asn Met Thr Leu Gly Tyr Arg
                 85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln Gln Val Val
                245                 250                 255

Glu Val Ile Gln Asn Ser Thr Ala Lys Val Ile Val Val Phe Ser Ser
            260                 265                 270

Gly Pro Asp Leu Glu Pro Leu Ile Lys Glu Ile Val Arg Arg Asn Ile
        275                 280                 285

Thr Gly Arg Ile Trp Leu Ala Ser Glu Ala Trp Ala Ser Ser Ser Leu
    290                 295                 300

Ile Ala Met Pro Glu Tyr Phe His Val Val Gly Gly Thr Ile Gly Phe
305                 310                 315                 320

Gly Leu Lys Ala Gly Gln Ile Pro Gly Phe Arg Glu Phe Leu Gln Lys
```

```
                325                 330                 335
Val His Pro Arg Lys Ser Val His Asn Gly Phe Ala Lys Glu Phe Trp
            340                 345                 350

Glu Glu Thr Phe Asn Cys His Leu Gln Asp Gly Ala Lys Gly Pro Leu
        355                 360                 365

Pro Val Asp Thr Phe Val Arg Ser His Glu Glu Gly Gly Asn Arg Leu
    370                 375                 380

Leu Asn Ser Ser Thr Ala Phe Arg Pro Leu Cys Thr Gly Asp Glu Asn
385                 390                 395                 400

Ile Asn Ser Val Glu Thr Pro Tyr Met Asp Tyr Glu His Leu Arg Ile
                405                 410                 415

Ser Tyr Asn Val Tyr Leu Ala Val Tyr Ser Ile Ala His Ala Leu Gln
            420                 425                 430

Asp Ile Tyr Thr Cys Leu Pro Gly Arg Gly Leu Phe Thr Asn Gly Ser
        435                 440                 445

Cys Ala Asp Ile Lys Lys Val Glu Ala Trp Gln Val Leu Lys His Leu
    450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Gly Lys Ile
        515                 520                 525

Leu Trp Ser Gly Phe Ser Arg Glu Val Pro Phe Ser Asn Cys Ser Arg
    530                 535                 540

Asp Cys Gln Ala Gly Thr Arg Lys Gly Ile Ile Glu Gly Glu Pro Thr
545                 550                 555                 560

Cys Cys Phe Glu Cys Ala Glu Cys Pro Asp Gly Glu Tyr Ser Gly Glu
                565                 570                 575

Thr Asp Ala Ser Ala Cys Asp Lys Cys
            580                 585

<210> SEQ ID NO 7
<211> LENGTH: 558
<212> TYPE: PRT
<213> ORGANISM: Murine

<400> SEQUENCE: 7

Phe Phe Pro Met Ile Phe Leu Glu Met Ser Ile Leu Pro Arg Met Pro
1               5                   10                  15

Asp Arg Lys Val Leu Leu Ala Gly Ala Ser Ser Gln Arg Ser Val Ala
            20                  25                  30

Arg Met Asp Gly Asp Val Ile Ile Gly Ala Leu Phe Ser Val His His
        35                  40                  45

Gln Pro Pro Ala Glu Lys Val Pro Glu Arg Lys Cys Gly Glu Ile Arg
    50                  55                  60

Glu Gln Tyr Gly Ile Gln Arg Val Glu Ala Met Phe His Thr Leu Asp
65                  70                  75                  80

Lys Ile Asn Ala Asp Pro Val Leu Leu Pro Asn Ile Thr Leu Gly Ser
                85                  90                  95

Glu Ile Arg Asp Ser Cys Trp His Ser Ser Val Ala Leu Glu Gln Ser
            100                 105                 110
```

-continued

Ile Glu Phe Ile Arg Asp Ser Leu Ile Ser Ile Arg Asp Glu Lys Asp
            115                 120                 125

Gly Leu Asn Arg Cys Leu Pro Asp Gly Gln Thr Leu Pro Pro Gly Arg
        130                 135                 140

Thr Lys Lys Pro Ile Ala Gly Val Ile Gly Pro Gly Ser Ser Ser Val
145                 150                 155                 160

Ala Ile Gln Val Gln Asn Leu Leu Gln Leu Phe Asp Ile Pro Gln Ile
                165                 170                 175

Ala Tyr Ser Ala Thr Ser Ile Asp Leu Ser Asp Lys Thr Leu Tyr Lys
            180                 185                 190

Tyr Phe Leu Arg Val Val Pro Ser Asp Thr Leu Gln Ala Arg Ala Met
        195                 200                 205

Leu Asp Ile Val Lys Arg Tyr Asn Trp Thr Tyr Val Ser Ala Val His
210                 215                 220

Thr Glu Gly Asn Tyr Gly Glu Ser Gly Met Asp Ala Phe Lys Glu Leu
225                 230                 235                 240

Ala Ala Gln Glu Gly Leu Cys Ile Ala His Ser Asp Lys Ile Tyr Ser
                245                 250                 255

Asn Ala Gly Glu Lys Ser Phe Asp Arg Leu Leu Arg Lys Leu Arg Glu
            260                 265                 270

Arg Leu Pro Lys Ala Arg Val Val Cys Phe Cys Glu Gly Met Thr
        275                 280                 285

Val Arg Gly Leu Leu Ser Ala Met Arg Arg Leu Gly Val Val Gly Glu
        290                 295                 300

Phe Ser Leu Ile Gly Ser Asp Gly Trp Ala Asp Arg Asp Glu Val Ile
305                 310                 315                 320

Glu Gly Tyr Glu Val Glu Ala Asn Gly Gly Ile Thr Ile Lys Leu Gln
                325                 330                 335

Ser Pro Glu Val Arg Ser Phe Asp Asp Tyr Phe Leu Lys Leu Arg Leu
            340                 345                 350

Asp Thr Asn Thr Arg Asn Pro Trp Phe Pro Glu Phe Trp Gln His Arg
        355                 360                 365

Phe Gln Cys Arg Leu Pro Gly His Leu Leu Glu Asn Pro Asn Phe Lys
        370                 375                 380

Lys Val Cys Thr Gly Asn Glu Ser Leu Glu Glu Asn Tyr Val Gln Asp
385                 390                 395                 400

Ser Lys Met Gly Phe Val Ile Asn Ala Ile Tyr Ala Met Ala His Gly
                405                 410                 415

Leu Gln Asn Met His His Ala Leu Cys Pro Gly His Val Gly Leu Cys
            420                 425                 430

Asp Ala Met Lys Pro Ile Asp Gly Arg Lys Leu Leu Asp Phe Leu Ile
        435                 440                 445

Lys Ser Ser Phe Val Gly Val Ser Gly Glu Glu Val Trp Phe Asp Glu
450                 455                 460

Lys Gly Asp Ala Pro Gly Arg Tyr Asp Ile Met Asn Leu Gln Tyr Thr
465                 470                 475                 480

Glu Ala Asn Arg Tyr Asp Tyr Val His Val Gly Thr Trp His Glu Gly
                485                 490                 495

Val Leu Asn Ile Asp Asp Tyr Lys Ile Gln Met Asn Lys Ser Gly Met
            500                 505                 510

Val Arg Ser Val Cys Ser Glu Pro Cys Leu Lys Gly Gln Ile Lys Val
        515                 520                 525

Ile Arg Lys Gly Glu Val Ser Cys Cys Trp Ile Cys Thr Ala Cys Lys

-continued

```
          530                 535                 540
Glu Asn Glu Phe Val Gln Asp Glu Phe Thr Cys Arg Ala Cys
545                 550                 555

<210> SEQ ID NO 8
<211> LENGTH: 4090
<212> TYPE: DNA
<213> ORGANISM: Murine

<400> SEQUENCE: 8
ttgttagtgc tggagacttc tacctaccat gccagctttg ctatcatgg gtctcagcct      60
ggctgctttc ctggagcttg ggatgggggc tctcttgtgt ctgtcacagc aattcaaggc    120
acaaggggac tacatactgg gcgggctatt tcccctgggc tcaaccgagg aggccactct    180
caaccagaga acacaaccca acagcatccc gtgcaacagg tatggaggct agtagctggg    240
gtgggagtga accgaagctt ggcagctttg ctccgtggt actaccaatc tgggaagagg     300
tggtgatcag tttccatgtg gcctcaggtt ctcacccctt ggtttgttcc tggccatggc    360
tatgaagatg gctgtggagg agatcaacaa tggatctgcc ttgctccctg gctgcggct     420
gggctatgac ctatttgaca catgctccga gccagtggtc accatgaaat ccagtctcat    480
gttcctggcc aaggtgggca gtcaaagcat tgctgcctac tgcaactaca cacagtacca    540
acccgtgtg ctggctgtca tcggcccca ctcatcagag cttgccctca ttacaggcaa     600
gttcttcagc ttcttcctca tgccacaggt gagcccactt cctttgtgtt ctcaaccgat    660
tgcacccatt gagctctcat atcagaaagt gcttcttgat caccacaggt cagctatagt    720
gccagcatgg atcggctaag tgaccgggaa acgtttccat ccttcttccg cacagtgccc    780
agtgaccggg tgcagctgca ggcagttgtg actctgttgc agaacttcag ctggaactgg    840
gtggccgcct tagggagtga tgatgactat ggccgggaag gtctgagcat cttttctagt    900
ctggccaatg cacgaggtat ctgcatcgca catgagggcc tggtgccaca acatgacact    960
agtggccaac agttgggcaa ggtgctggat gtactacgcc aagtgaacca agtaaagta   1020
caagtggtgg tgctgtttgc ctctgcccgt gctgtctact cccttttag ttacagcatc     1080
catcatggcc tctcacccaa ggtatgggtg ccagtgagt cttggctgac atctgacctg     1140
gtcatgacac ttcccaatat tgcccgtgtg ggcactgtgc ttgggttttt gcagcggggt    1200
gccctactgc ctgaattttc ccattatgtg gagactcacc ttgccctggc cgctgaccca    1260
gcattctgtg cctcactgaa tgcggagttg gatctggagg aacatgtgat ggggcaacgc    1320
tgtccacggt gtgacgacat catgctgcag aacctatcat ctgggctgtt gcagaaccta    1380
tcagctgggc aattgcacca ccaaatattt gcaacctatg cagctgtgta cagtgtggct    1440
caagccctc acaacaccct acagtgcaat gtctcacatt gccacgtatc agaacatgtt    1500
ctaccctggc aggtaagggt agggttttt gctgggtttt gctgctcct gcaggaacac      1560
tgaaccaggc agagccaaat cttgttgtga ctggagaggc cttaccctga ctccactcca    1620
cagctcctgg agaacatgta caatatgagt ttccatgctc gagacttgac actacagttt    1680
gatgctgaag ggaatgtaga catggaatat gacctgaaga tgtgggtgtg gcagagccct    1740
acacctgtat tacatactgt gggcaccttc aacggcaccc ttcagctgca gcagtctaaa    1800
atgtactggc caggcaacca ggtaaggaca agacaggcaa aaaggatggt gggtagaagc    1860
ttgtcggtct tgggccagtg ctagccaagg ggaggcctaa cccaaggctc catgtacagg    1920
tgccagtctc ccagtgttcc cgccagtgca aagatggcca ggttcgccga gtaaagggct    1980
```

```
ttcattcctg ctgctatgac tgcgtggact gcaaggcggg cagctaccgg aagcatccag    2040
gtgaaccgtc ttccctagac agtctgcaca gccgggctag ggggcagaag cattcaagtc    2100
tggcaagcgc cctcccgcgg ggctaatgtg agacagtta ctgtggggc tggctgggga     2160 ggtcggtctc ccatcagcag accccacatt acttttcttc cttccatcac tacagatgac    2220
ttcacctgta ctccatgtaa ccaggaccag tggtccccag agaaaagcac agcctgctta    2280
cctcgcaggc ccaagtttct ggcttggggg agccagttg tgctgtcact cctcctgctg     2340 cttttgcctgg tgctgggtct agcactggct gctctggggc tctctgtcca ccactgggac   2400
agccctcttg tccaggcctc aggtggctca cagttctgct ttggcctgat ctgcctaggc    2460
ctcttctgcc tcagtgtcct tctgttccca gggcggccaa gctctgccag ctgccttgca    2520
caacaaccaa tggctcacct ccctctcaca ggctgcctga gcacactctt cctgcaagca    2580
gctgagacct ttgtggagtc tgagctgcca ctgagctggg caaactggct atgcagctac    2640
cttcggggac tctgggcctg gctagtgta ctgttggcca cttttgtgga ggcagcacta    2700
tgtgcctggt atttgatcgc tttcccacca gaggtggtga cagactggtc agtgctgccc    2760
acagaggtac tggagcactg ccacgtgcgt tcctgggtca gctgggcttt ggtgcacatc    2820
accaatgcaa tgttagcttt cctctgcttt ctgggcactt tcctggtaca gagccagcct    2880
ggccgctaca accgtgcccg tgtctcacc ttcgccatgc tagcttattt catcacctgg     2940
gtctcttttg tgcccctcct ggccaatgtg caggtggcct accagccagc tgtgcagatg    3000
ggtgctatcc tagtctgtgc cctgggcatc ctggtcacct tccacctgcc caagtgctat    3060
gtgcttcttt ggctgccaaa gctcaacacc caggagttct tcctgggaag gaatgccaag    3120
aaagcagcag atgagaacag tggcggtggt gaggcagctc agggacacaa tgaatgacca    3180
ctgacccgtg accttcctt tagggaacct agccctacca gaaatctcct aagccaacaa    3240 gcccgaata gtacctcagc ctgagacgtg agacacttaa ctatagactt ggactccact    3300
gaccttagcc tcacagtgac cccttcccca aaccccaag gcctgcagtg cacaagatgg    3360 acctatgag cccacctatc ctttcaaagc aagattatcc ttgatcctat tatgcccacc    3420
taaggcctgc ccaggtgacc cacaaaaggt tctttgggac ttcatagcca tactttgaat    3480
tcagaaattc cccaggcaga ccatgggaga ccagaaggta ctgcttgcct gaacatgccc    3540
agccctgagc cctcactcag caccctgtcc aggcgtccca ggaatagaag gctgggcatg    3600
tatgtgtgtg tgtgtgtgtg tgtgtgtgtg tgtgtgtgtg tgtgtatgta cgtatgtatg    3660
tatgtatcag gacagaacaa gaaagacatc aggcagagga cactcaggag gtaggcaaca    3720
tccagccttc tccatcccta gctgagccct agcctgtagg agagaaccag gtcgccgcca    3780
gcaccttgga cagatcacac acagggtgcg ggtcagcacc acggcagcg ccagccacgc     3840 gggacccctg gaatcagctt ctagtaccaa ggacagaaaa gttgccgcaa ggccccttac    3900
tggccagcac cagggacaga gccacatgcc taagcggcaa gggacaagag catcgtccat    3960
ctgcaggcag gatcagaccc gggtcagttc tggactggcc cccacacctg aatcccggag    4020
cagctcagct ggagaaaaga gaaacaagcc acacatcagt cccataaaat taaacgcttt    4080
ttttagtgtt                                                          4090
```

<210> SEQ ID NO 9
<211> LENGTH: 3153
<212> TYPE: DNA
<213> ORGANISM: Mouse
<300> PUBLICATION INFORMATION:
<308> DATABASE ACCESSION NUMBER: GenBank Accession No. AF368024

<309> DATABASE ENTRY DATE: 2001-05-23
<300> PUBLICATION INFORMATION:

<400> SEQUENCE: 9

| | | | | | |
|---|---|---|---|---|---|
| ccatgccagc | tttggctatc | atgggtctca | gcctggctgc | tttcctggag | cttgggatgg | 60 |
| gggcctcttt | gtgtctgtca | cagcaattca | aggcacaagg | ggactacata | ctgggcgggc | 120 |
| tatttcccct | gggctcaacc | gaggaggcca | ctctcaacca | gagaacacaa | cccaacagca | 180 |
| tcccgtgcaa | caggtatgga | ggctagtagc | tggggtggga | gtgaaccgaa | gcttggcagc | 240 |
| tttggctccg | tggtactacc | aatctgggaa | gaggtggtga | tcagtttcca | tgtggcctca | 300 |
| ggttctcacc | ccttggtttg | ttcctggcca | tggctatgaa | gatggctgtg | gaggagatca | 360 |
| acaatggatc | tgccttgctc | cctgggctgc | ggctgggcta | tgacctattt | gacacatgct | 420 |
| ccgagccagt | ggtcaccatg | aaatccagtc | tcatgttcct | ggccaaggtg | ggcagtcaaa | 480 |
| gcattgctgc | ctactgcaac | tacacacagt | accaaccccg | tgtgctggct | gtcatcggcc | 540 |
| cccactcatc | agagcttgcc | ctcattacag | gcaagttctt | cagcttcttc | ctcatgccac | 600 |
| aggtgagccc | acttcctttg | tgttctcaac | cgattgcacc | cattgagctc | tcatatcaga | 660 |
| aagtgcttct | tgatcaccac | aggtcagcta | tagtgccagc | atggatcggc | taagtgaccg | 720 |
| ggaaacgttt | ccatccttct | tccgcacagt | gcccagtgac | cgggtgcagc | tgcaggcagt | 780 |
| tgtgactctg | ttgcagaact | tcagctgaaa | ctgggtggcc | gccttaggga | gtgatgatga | 840 |
| ctatggccgg | gaaggtctga | gcatcttttc | tagtctggcc | aatgcacgag | gtatctgcat | 900 |
| cgcacatgag | ggcctggtgc | cacaacatga | cactagtggc | caacagttgg | gcaaggtgct | 960 |
| ggatgtacta | cgccaagtga | accaaagtaa | agtacaagtg | gtggtgctgt | ttgcctctgc | 1020 |
| ccgtgctgtc | tactcccttt | ttagttacag | catccatcat | ggcctctcac | ccaaggtatg | 1080 |
| ggtggccagt | gagtcttggc | tgacatctga | cctggtcatg | acacttccca | atattgcccg | 1140 |
| tgtgggcact | gtgcttgggt | ttttgcagcg | gggtgcccta | ctgcctgaat | tttcccatta | 1200 |
| tgtggagact | caccttgccc | tggccgctga | cccagcattc | tgtgcctcac | tgaatgcgga | 1260 |
| gttggatctg | gaggaacatg | tgatgggca | acgctgtcca | cggtgtgacg | acatcatgct | 1320 |
| gcagaaccta | tcatctgggc | tgttgcagaa | cctatcagct | gggcaattgc | accaccaaat | 1380 |
| atttgcaacc | tatgcagctg | tgtacagtgt | ggctcaagcc | cttcacaaca | ccctacagtg | 1440 |
| caatgtctca | cattgccacg | tatcagaaca | tgttctaccc | tggcaggtaa | gggtagggtt | 1500 |
| ttttgctggg | ttttgcctgc | tcctgcagga | acactgaacc | aggcagagcc | aaatcttgtt | 1560 |
| gtgactggag | aggccttacc | ctgactccac | tccacagctc | ctggagaaca | tgtacaatat | 1620 |
| gagtttccat | gctcgagact | tgacactaca | gtttgatgct | gaagggaatg | tagacatgga | 1680 |
| atatgacctg | aagatgtggg | tgtggcagag | ccctacacct | gtattacata | ctgtgggcac | 1740 |
| cttcaacggc | acccttcagc | tgcagcagtc | taaaatgtac | tggccaggca | accaggtaag | 1800 |
| gacaagacag | gcaaaaagga | tggtgggtag | aagcttgtcg | gtcttgggcc | agtgctagcc | 1860 |
| aaggggaggc | ctaacccaag | gctccatgta | caggtgccag | tctcccagtg | ttcccgccag | 1920 |
| tgcaaagatg | gccaggttcg | ccgagtaaag | ggctttcatt | cctgctgcta | tgactgcgtg | 1980 |
| gactgcaagg | cgggcagcta | ccggaagcat | ccaggtgaac | cgtcttccct | agacagtctg | 2040 |
| cacagccggg | ctaggggca | gaagcattca | agtctggcaa | gcgccctccc | gcggggctaa | 2100 |
| tgtggagaca | gttactgtgg | gggctggctg | ggaggtcgg | tctcccatca | gcagaccacca | 2160 |
| cattactttt | cttccttcca | tcactacaga | tgacttcacc | tgtactccat | gtaaccagga | 2220 |

```
ccagtggtcc ccagagaaaa gcacagcctg cttacctcgc aggcccaagt ttctggcttg    2280 ggggagcca gttgtgctgt cactcctcct gctgctttgc ctggtgctgg gtctagcact    2340
ggctgctctg gggctctctg tccaccactg ggacagccct cttgtccagg cctcaggtgg    2400
ctcacagttc tgctttggcc tgatctgcct aggcctcttc tgcctcagtg tccttctgtt    2460
cccaggacgg ccaagctctg ccagctgcct tgcacaacaa ccaatggctc acctccctct    2520
cacaggctgc ctgagcacac tcttcctgca agcagctgag acctttgtgg agtctgagct    2580
gccactgagc tgggcaaact ggctatgcag ctaccttcgg ggactctggg cctggctagt    2640
ggtactgttg gccacttttg tggaggcagc actatgtgcc tggtatttga tcgctttccc    2700
accagaggtg gtgacagact ggtcagtgct gcccacagag gtactggagc actgccacgt    2760
gcgttcctgg gtcagcctgg gcttggtgca catcaccaat gcaatgttag ctttcctctg    2820
ctttctgggc actttcctgg tacagagcca gcctggccgc tacaaccgtg cccgtggtct    2880
caccttcgcc atgctagctt atttcatcac ctgggtctct tttgtgcccc tcctggccaa    2940
tgtgcaggtg gcctaccagc cagctgtgca gatgggtgct atcctagtct gtgccctggg    3000
catcctggtc accttccacc tgcccaagtg ctatgtgctt ctttggctgc caaagctcaa    3060
cacccaggag ttcttcctgg aaggaatgc caagaaagca gcagatgaga acagtggcgg    3120
tggtgaggca gctcaggaac acaatgaatg acc                                 3153
```

<210> SEQ ID NO 10
<211> LENGTH: 483
<212> TYPE: DNA
<213> ORGANISM: Artificial Sequence
<220> FEATURE:
<223> OTHER INFORMATION: Description of Artificial Sequence:
      oligonucleotide probe

<400> SEQUENCE: 10

```
acagcaattc aaggcacaag gggactacat actgggcggg ctatttcccc tgggctcaac     60
cgaggaggcc actctcaacc agagaacaca acccaacagc atcccgtgca acaggtatgg    120
aggctagtag ctggggtggg agtgaaccga agcttggcag cttttggctcc gtggtactac    180 caatctggga agaggtggtg atcagtttcc atgtggcctc aggttctcac cccttggttt    240
gttcctggcc atggctatga agatggctgt ggaggagatc aacaatggat ctgccttgct    300
ccctgggctg cggctgggct atgacctatt tgacacatgc tccgagccag tggtcaccat    360
gaaatccagt ctcatgttcc tggccaaggt gggcagtcaa agcattgctg cctactgcaa    420
ctacacacag taccaacccc gtgtgctggc tgtcatcggc ccccactcat cagagcttgc    480
cct                                                                  483
```

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 11

```
gccaacccac agcctctgct ttaattttgg gggatac                              37
```

<210> SEQ ID NO 12
<211> LENGTH: 35
<212> TYPE: DNA
<213> ORGANISM: Artificial Sequence

```
<220> FEATURE:
<223> OTHER INFORMATION: Description of Artificial Sequence:
      oligonucleotide primer

<400> SEQUENCE: 12
gccaagttct aattccatca gaagctgact ctagc                              35

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
ggcatcctcc ttcagcagca tcacagactc c                                  31

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
gacctgcagg ggccctcgac tataacttcg                                    30

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
acagcaattc aaggcacaag g                                             21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16
gagggcaagc tctgatgagt g                                             21
```